US007189700B2

(12) United States Patent
Yang et al.

(10) Patent No.: US 7,189,700 B2
(45) Date of Patent: *Mar. 13, 2007

(54) ANTI-CHRONDROSARCOMA COMPOUNDS

(75) Inventors: Shu-Ping Yang, Alpharetta, GA (US);
Stephen Quirk, Alpharetta, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 375 days.

This patent is subject to a terminal disclaimer.

(21) Appl. No.: 10/601,059

(22) Filed: Jun. 20, 2003

(65) Prior Publication Data

US 2004/0259802 A1    Dec. 23, 2004

(51) Int. Cl.
*A61K 38/00* (2006.01)
*A61K 38/04* (2006.01)

(52) U.S. Cl. ............................ 514/17; 514/2; 514/12; 514/13; 530/326; 530/328

(58) Field of Classification Search ............... 514/2
See application file for complete search history.

(56) References Cited

U.S. PATENT DOCUMENTS

| | | | |
|---|---|---|---|
| 4,424,552 A | 1/1984 | Marcoux | 361/306 |
| 5,270,447 A | 12/1993 | Liotta et al. | 530/326 |
| 5,280,106 A | 1/1994 | Liotta et al. | 530/330 |
| 5,372,809 A | 12/1994 | Liotta et al. | 424/185.1 |
| 5,585,356 A | 12/1996 | Liotta et al. | 514/17 |
| 5,698,671 A | 12/1997 | Stetler-Stevenson et al. | 530/324 |
| 5,770,691 A | 6/1998 | Fields et al. | 530/328 |
| 5,811,252 A | 9/1998 | Verheijen | 435/23 |
| 5,869,277 A | 2/1999 | Stetler-Stevenson et al. | 435/28 |
| 6,043,087 A | 3/2000 | Bini et al. | 435/337 |
| 6,127,139 A | 10/2000 | Te Koppele et al. | 435/24 |
| 6,184,022 B1 | 2/2001 | Seiki et al. | |
| 6,191,225 B1 | 2/2001 | Barkac et al. | 525/208 |
| 6,204,043 B1 | 3/2001 | Shapiro | 435/226 |
| H1973 H | 7/2001 | Hu | |
| 6,274,703 B1 | 8/2001 | Goldberg | 530/324 |
| 6,399,371 B1 | 6/2002 | Falduto et al. | |
| 6,482,802 B1 | 11/2002 | Hu et al. | |
| 6,753,310 B1 | 6/2004 | Oku et al. | |
| 6,812,339 B1 | 11/2004 | Venter et al. | |
| 6,906,036 B2 | 6/2005 | Quirk et al. | |
| 2001/0016333 A1 | 8/2001 | Seiki et al. | 435/69.1 |
| 2001/0031478 A1 | 10/2001 | Bronstein et al. | 435/7.5 |
| 2002/0099004 A1 | 7/2002 | Lund et al. | |
| 2003/0012794 A1 | 1/2003 | Srivastava et al. | |
| 2003/0096757 A1 | 5/2003 | Quirk et al. | |
| 2003/0148959 A1 | 8/2003 | Quirk et al. | |
| 2003/0166567 A1 | 9/2003 | Quirk et al. | |
| 2003/0199440 A1 | 10/2003 | Dack et al. | |
| 2004/0010001 A1 | 1/2004 | Au et al. | |
| 2005/0239710 A1 | 10/2005 | Quirk et al. | |

FOREIGN PATENT DOCUMENTS

| | | |
|---|---|---|
| CN | 1549722 | 11/2004 |
| EP | 0917165 | 5/1999 |
| JP | 06213888 A | 5/1994 |
| JP | 06300757 A | 10/1994 |
| JP | 07159402 A | 6/1995 |
| JP | 07-303482 | 11/1995 |
| JP | 07-330795 | 12/1995 |
| JP | 08134098 A | 5/1996 |
| JP | 08136548 A | 5/1996 |
| JP | 08217800 A | 8/1996 |
| JP | 09023889 A2 | 1/1997 |
| JP | 09084589 A | 3/1997 |
| JP | 09087299 A | 3/1997 |
| JP | 09136841 A | 5/1997 |
| JP | 09206099 A | 8/1997 |
| JP | 09249700 | 9/1997 |
| JP | 10210982 A | 8/1998 |
| JP | 10287700 A | 10/1998 |
| JP | 10313896 A | 12/1998 |
| JP | 2000270874 A | 10/2000 |
| JP | 2001011093 A2 | 1/2001 |
| JP | 2001-072589 | 3/2001 |
| WO | WO-90/10228 | 9/1990 |
| WO | WO-90/10228 A1 | 9/1990 |
| WO | WO-94/10208 | 5/1994 |

(Continued)

OTHER PUBLICATIONS

Agren, Magnus S., "Matrix metalloproteinases (MMPs) are required for re-epitheliazation of cutaneous wounds", *Archives Dermatol. Res.*, 291, (1999), 583-590.

Attie, Kenneth M., "Genetic studies in idiopathic short stature", *Current Opinion in Pediatrics*, 12, (2000), 400-404.

Azzam, H. S., et al., "Association of MMP-2 activation potential with metastatic progression in human breast cancer cell lines independent of .MMP-2 production", *J. Natl. Cancer Inst.*, 85 (21), (1993),1758-1764.

Baker, E. A., et al., "Proteinases, their inhibitors, and cytokine profiles in acute wound fluid", *Wound Repair Regen.*, 8 (5), (2000), 392-398.

(Continued)

*Primary Examiner*—Cecilia J. Tsang
*Assistant Examiner*—Maury Audet
(74) *Attorney, Agent, or Firm*—Schwegman, Lundberg, Woessner, & Kluth, P.A.

(57) ABSTRACT

The invention provides inhibitors of chondrosarcoma cell growth that are useful as anti-cancer and anti-tumor agents. The inhibitors are peptides having sequences related to cleavage regions of the proenzyme forms of matrix metalloproteinases and that can inhibit the activity of matrix metalloproteinases. The peptide inhibitors of the invention can be formulated into therapeutic compositions, lotions, creams and wound dressings.

7 Claims, 17 Drawing Sheets

FOREIGN PATENT DOCUMENTS

| WO | WO-95/02045 A2 | 1/1995 |
| --- | --- | --- |
| WO | WO-95/15374 A1 | 6/1995 |
| WO | WO-96/18725 | 6/1997 |
| WO | WO-97/25437 | 7/1997 |
| WO | WO-98/04287 | 2/1998 |
| WO | WO-98/12309 | 3/1998 |
| WO | WO-98/31818 | 7/1998 |
| WO | WO-98/40475 | 9/1998 |
| WO | WO-98/42865 | 10/1998 |
| WO | WO-99/05261 | 2/1999 |
| WO | WO-99/31969 | 7/1999 |
| WO | WO-98/34641 A1 | 8/1999 |
| WO | WO-99/58126 A1 | 11/1999 |
| WO | WO-99/65519 | 12/1999 |
| WO | WO-00/20860 | 4/2000 |
| WO | WO-00/53219 A2 | 9/2000 |
| WO | WO-00/74634 A2 | 12/2000 |
| WO | WO-01/10437 | 2/2001 |
| WO | WO-01/13937 A1 | 3/2001 |
| WO | WO-0126671 A1 | 4/2001 |
| WO | WO-01/38558 A2 | 5/2001 |
| WO | WO-01/54723 A1 | 8/2001 |
| WO | WO-01/62206 | 8/2001 |
| WO | WO-01/62261 | 8/2001 |
| WO | WO-00/63227 | 10/2001 |
| WO | WO-03/018748 A2 | 3/2003 |

OTHER PUBLICATIONS

Becker, Joseph W., "Stromelysin-1: Three-dimensional structure of the inhibited catalytic domain and of the C-truncated proenzyme", *Protein Science*, 4, (1995), 1966-1976.

Berend, Keith R., et al., "Association between ratio of matrix metalloproteinase-1 to tissue inhibitor of metalloproteinase-1 and local recurrence, metastasis, and survival in human chondrosarcoma", *Journal of Bone & Joint Surgery—American* vol. 80(1), (1999), 893-895.

Bhide, V. M., et al., "Use of a fluorogenic septapeptide matrix metalloproteinase assay to assess responses to periodontal treatment", *J. Periodontol.*, 71(5), (2000), 690-700.

Bickett, D. M., et al., "A high throughput fluorogenic substrate for interstitial collagenase (MMP-1) and gelatinase (MMP-9)", *Anal. Biochem.*, 212 (1), (1993), 58-64.

Bickett, D. M., et al., "A high throughput fluorogenic substrate for stromelysin (MMP-3)", *Ann. N Y Acad. Sci.*, 732, (1994), 351-355.

Blaschke, Rudiger J., et al., "SHOX: Growth, Leri-Weill and Turner Syndromes", *TEM*, 11, (2000), 227-230.

Bremer, C., et al., "In Vivo molecular toarget assessment or matrix metaloproteinase inhibition", *Nat. Med.*, 7 (6), (2001), 743-748.

Brown, P. D., et al., "Cellular activation of the 72 kDa type IV procollagenase/TIMP-2 complex", *Kidney Int.*, 43 (1), (1993), 163-170.

Brown, Rebeccah L., et al., "PDGF and TGF-a Act Synergistically to Improve Wound Healing in the Genetically Diabetic Mouse", *Journal of Surgical Research*, 56, (1994), 562-570.

Browner, Michelle F., "Matrilysin-Inhibitor Complexes: Common Themes among Metalloproteases", *Biochemistry*, 34, (1995), 6602-6610.

Cabrele, Chiara, et al., "Y-receptor affinity modulation by the design of pancreatic . . . ", *Peptides*, 22, (2001), 365-378.

Calabrese, Edward J., "Cell Migration / Chemotaxis: Biphasic Dose Responses", *Critical Reviews in Toxicology*, 31 (4&5), (2001), 615-624.

Calvin, Melissa, "Cutaneous Wound Repair", *Wounds: A Compendium of Clinical Research and Practice*, 10 (1), (1998), 12-32.

Chen, L. C., et al., "Disruption of the cysteine-75 and zinc ion coordinatin is not sufficient to activate the precursor of human matrix metalloproteinase 3 (stromelysin 1)", *Biochemistry*, 32 (39), (1993), 10289-10295.

Chi, Yeon Sook, et al., "Effects of the Chestnut Inner Shell Extract on the Expression of Adhesin Molecules, Fibronectin and Vitronectin, of Skin Fibroblasts in Culture", *Archives of Pharmacal Research*, 25 (4), (2002), 469-474.

Chin, Jason W., et al., "Concerted Evolution of Structureand Function in a Miniature Protein", *J. Am. Chem. Soc.*, (2001), 2929-2930.

Chin, Jason W., et al., "Methodology for Optimizing Functional Miniature Proteins Based on Avian Pancreatic Polypeptide Using Phage Display", *Bioorganic & Medicinal Chemistry Letters*, 1, (2001), 1501-1505.

Clark, Richard A., "Wound Repair", *The Molecular and Cellular Bilogy of Wound Repair—2nd ed.*, Plenum Press, NY,(1995), 3-50.

Colandrea, Teresa Di, "Epidermal Expression of Collagenase Delays Wound-Healing in Transgenic Mice", *The Journal of Investigative Dermatology*, (1998), 1029-1033.

Duivenvoorden, Wilhelmina C., "Use of Tetracycline as an Inhiitor of Matrix Metalloproteinase Activity Secreted by Human Bone-Metastasizing Cancer Cells", *Invasion Metastasis*, 17, (1997), 312-322.

Duncan, M. E., et al., "Human matrix metalloproteinase-9: activation by limited trypsin", *Eur. J. Biochem.*, 258 (1), (1998), 37-43.

Farmer, W. H., et al., "A continuous fluorescent assay for measuring protease activity using natural protein substrate", *Anal. Biochem.*, 197 (2), (1991), 347-352.

Fernandez-Catalan, Carlos, "Crystal structure of the complex formed by the membrane type 1-matrix metalloproteinase with the tissue inhibitor of metalloproteinases-2, the soluble progelatinase A receptor", *The EMBO Journal*, 17 (17), (1998), 5238-5248.

Freije, J. J., et al., "Molecular cloning and expression of collagenase-3, a novel human matrix metalloproteinase produced by breast carcinomas", *J. Biol. Chem.*, 269 (24), (1994), 16766-16773.

Freire, E., et al., "Calorimentrically Determined Dynamics Of Complex Unfolding Transitions in Proteins", *Annual Review of Biophysics and Biophysical Chemistry*, 19, (1990), 159-188.

Garbett, E. A., et al., "Proteolysis in human breast and colorectal cancer", *Br. J. Cancer*, 81 (2), (1999), 287-293.

Gomis-Ruth, Franz-Xaver, "Mechanism of inhibition of the human matrix metalloproteinase stromelysin-1 by TIMP-1", *Letters to Nature*, 389, (1997), 77-81.

Grams, Frank, "X-ray structures of human neutrophil collagenase complexed with peptide hydrozamate and peptide thiol inhibitors", *European Journal of Biochemistry*, 228, (1995), 830-841.

Guex, Nicols, "Swiss-MODEL and the Swiss-Pdb Viewer: An environment for comparative protein modeling", *Electrophesis*, 18, (1997), 2714-2723.

Higgins, Desond G., "Clustal V: improved software for multiple sequence alignment", *Computer applications in the biosciences*, 8 (2), (1992), 189-191.

Hilpert, Kai, et al., "Characterizing and Optimizing Protease/Peptide Inhabitor Interactions . . . ", *J. Biochem.*, 128, (2000), 1051-1057.

Hollis, Thomas, et al., "Structure of the gene 2.5 protein, a single-stranded DNA binding . . . ", *Department of Biological Chemistry and Molecular Pharmacology*, (2001), 9557-9562.

Howard, Eric W., "Preferential Inhibition of 72- and 92-kDa Gelatinases by Tissue Inhibitor of Metalloproteinases-2", *The Journal of Biological Chemistry*, 266 (20), (1991), 13070-13075.

Huang, Wen, "Folding and characterization of the amino-terminal domain of human tissue inhibitor of metalloproteinases-1 (TIMP-1) expressed at high yield in *E. coli*", *FEBS Letters*, 384, (1996), 155-161.

Itoh, M., et al., "Flow injeciton analysis for measurement of activity of matrix metalloproteinase-7 (MMP-7)", *J. Pharm. Biomed. Anal.*, 15 (9-10), (1997), 1417-1426.

Karlsson, Robert, et al., "Experimental Design for Kinetic Analysis of Protein-Protein Interactions with surface plasmon resonance biosensors", *Journal of Immunological Methods*, 200, (1997), 121-133.

Kerkela, E., et al., "Human macrophage metalloelastase (MMP-12) expression is induced in chondrocytes during fetal development and malignant transformation", *Bone.* 29(5), (2001), 487-493.

Knauper, V., et al., "Biochemical charictorization of human collegenase-3", *J. Biol. Chem.*, 271 (3), (1996), 1544-1550.

Knox, J. D., et al., "Matrilysin expression in human prostate carcinoma.", *Mol. Carcinog.*, 15 (1), (1996), 57-63.

Lakowicz, Joseph R., "Energy Transfer", *Principles of Fluorescence Spectroscopy*, Chapter 10,(1983), 303-339.

Lee, P. P., et al., "Functional role of matrix metalloproteinases (MMPs) in mammary epithelial cell development", *J. Cell Physiol.*, 188 (1), (2001), 75-88.

Levit, Shimon, et al., "Ribonucleas S-Peptide", *The Jurnal of Biological Chemistry*, 251 (5), (1976), 1333-1339.

Levy, Daniel E., "Matrix Metalloproteinase Inhibitors: A Structure-Activity Study", *Journal of Medicinal Chemistry*, 41, (1998), 199-223.

Li, J., et al., "Structure of full-length porcine synovial collagenase reveals a C-termainal domain containing a calcium-linked, four-bladed b-propeller", *Structure*, 3 (6), (1995), 541-549.

Libson, Andrew M., "Crystal structure of the haemopexin-like C-terminal domain of gelatinase A", *Nature Structural Biology*, 2 (11), (1995), 938-942.

Lofas, Stefan, "Dextran modified gold for surfaces for surface plasmon resonance sensors: immunoreactivity of immobilized antibodies and antibody-surface interaction studies", *Colloids and Surfaces B: Biointerfaces*, 1, (1993), 83-89.

Melchiori, A., et al., "Inhibition of tumor cell invasion by a highly conserved peptide . . . ", *Cancer Res.*, 58 (8), (1992), 2353-2356.

Morton, Thomas A., "Intetpreting Complex Binding Kinetics from Optical Biosensors: A Comparison of Analysis by Linearization, the Integrated Rate Equation, and Numerical Integration", *Analytical Biochemistry*, 227, (1995), 176-185.

Moses, M. A., "Temporal Study of the Activity of Matrix Metalloproteinases and Their Endogenous Inhibitors During Wound Healing", *Journal of Cellular Biochemistry*, 60, (1996), 379-386.

Nagase, H., et al., "Design and characterization of fluorogenic substrate selectively hydrolyzed by stromelysin 1 (matrix metalloproteinase-3)", *J. Biol. Chem.*, 269 (33), (1994), 20952-20957.

O'Connell, James P., et al., "Analysis of the role of the COOH-terminal domain in the activation, proteolytic activity, and tissue inhibitor of metalloproteinase interactions of gelatinase B", *J. Biol. Chem.*, 269 (21), (1994), 14967-14973.

O'Meara, S. M., et al., "Systematic review of antimicrobal agents used for chronic wounds", *British Journal of Surgery*, 88 (1), (2001),4-21.

O'Shannessy, Daniel J., "Determination of Rate and Equilibrium Binding Constants for Macromolecular Interactions Using Surface Plasmon Resonance: Use of Nonlinear Squares Analysis Methods", *Analytical Biochemistry*, 212, (1993), 457-468.

Odake, Shinjiro, "Inhibition of matrix metalloproteinase by peptidyl hydroxamic acids", *Biochemical and Biophysical Research Communications*, 199 (3), (1994), 1442-1446.

Ohtsuka, Y., et al., "MIP-2 secreted by epithelial cells increases meutophil and lymphocyte recruitment in the mouse instestine", *Gut*, 49 (4), (2001), 526-533.

Okada, Y., et al., "Matrix metalloproteinase 9 (92-kDa gelatinase/ type IV collagenase) from HT 1080 human fibrosarcoma cells . . . ", *J. Biol. Chem.*, 267 (30), (1992), 21712-21719.

Olson, Matthew W., "Kinetic Analysis of the Binding of Human Matrix Metalloproteinase-2 and -9 to Tissue Inhibitor of Metalloproteinase (TIMP)-1 and TIMP-2", *The Journal of Biological Chemistry*, 272 (47), (1997), 29975-29983.

Postlethwaite, Arnold E., et al., "Fibrolast Chemoattractants", *Methods in Enzymology*, 163, (1988), 694-707.

Raza, Saadia L., et al., "Matrix metalloproteinases: Pro and anti-angiogenetic activities", *Chemical Abstracts 14-Mammalian Pathological Biochemistry*, 135 (4), (2001), 483.

Reinemer, Peter, "Structural implications for the role of the N terminus in the 'superactivation' of collagenases", *FEBS Letters*, 338, (1994), 227-233.

Renil, Manat, et al., "Flourescent quenched peptide libraries as tool for identification . . . ", *Chemical Abstracts 7-Enzymes*, 129 (26), (1998), 218.

Saarialho-Kere, U.K. , "Patterns of matrix metaloproteinase and TMP expression in chronic ulcers", *Archives of Dermatological Research*, 290, (1998), S47-S54.

Sakamoto, Akio, et al., "Expression of membrane type 1 matrix metalloproteinase, matrix metalloproteinase 2 and tissue inhibitor of metalloproteinase 2 in human cartilaginous tumors with special emphasis on mesenchymal and dedifferentiated chondrosarcoma", *Journal of Cancer Research & Clinical Oncology*, 125(10), (1999), 541-548.

Sang, Q. A., et al., "Activation of Human Progelatinase A by Collagenase and matrilysin . . . ", *J. Protein Chem.*, 15 (3), (1996), 243-253.

Sayle, Roger A., "Rasmol: biomolecular graphics for all", *Trends in Biochemical Sciences*, 20, (1995), 333-379.

Segel, Irwin H., "Kinetics of Unireactant Enzymes", *Enzyme Kinetics*, Chapter 2, (1975), 18-99.

Shapiro, S. D., et al., "Activation of the 92-kDa gelatinase by stromelysin and 4-aminophenylmercuric acetate . . . ", *J. Biol. Chem.*, 270 (11), (1995), 6531-6536.

Soderstrom, M., et al., "Expression of matrix metalloproteinases and tissue inhibitors of metalloproteinases in human chondrosarcomas", *APMIS*, 109(4), (2001), 305-315.

Stack, M. Sharon, et al., "Fluorescence quenching studies of matrix metalloproteinases (MMPs): evidence for structural rearrangement of the proMMP-2/TIMP-2 complex upon mercurial activation", *Arch. Biochem. Biophys.*, 333 (1), (1996), 163-169.

Staiano-Coico, Lisa, et al., "Wound Fluids: A Reflection of the State of Healing", Ostomy Wound Management, 46, (2000), 85S-93S.

Stetler-Stevenson, W. G., et al., "Inhibition of human type IV collagenase by a highly conserved peptide sequence derived from its prosegment", *Am. J. Med. Sci.*, 302 (3), (1991), 163-170.

Stetler-Stevenson, W. G., et al., "The activation of human type IV collagenase proenzyme . . . ", *J. Biol. Chem.*, 264 (3), (1989), 1353-1356.

Su, Jui-Lan, "Monoclonal Antibodies against Human Collagenase and Stromelysin", *Hybridoma*, 14 (4), (1995), 383-390.

Taylor, Kenneth B., "The Mechanism of Inhabitation of Collagenase by TIMP-1", *The Journal of Biological Chemistry*, 271 (39), (1996), 23938-23945.

Te, Koppele, et al., "Method for assaying proteolytic enzymes using flourescence . . . ", *Chemical Abstracts 7-Enzymes*, 127 (11), (1997), 241.

Tuuttila, Ari, "Three-dimensional Structure of Human Tissue Inhibitor of Metalloproteinases-2 at 2.1 A Resolution", *Journal of Molecular Biology*, 284, (1998), 1133-1140.

Vaalamo, Maarit, "Distinct populations of stromal cells express collagenase-3 (MMP-13) and collagenase-1 (MMP-1) in chronic ulcers but not in normally healing wounds", *The Jounal of Investigative Dermatology*, 109 (1), (1997), 96-101.

Vaalamo, Maarit, "Patterns of matrix metalloproteinase and TIMP-1 expressions in chronic and normally healing human cutaneous wounds", *British Journal of Dermatology*, 135, (1996), 52-59.

Verheijen, J. H., et al., "Modified proenzymes as artificial substances for proteolytic . . . ", *Biochem J.*, 323, (1997), 603-609.

Weckroth, Miina, "Matrix Metalloproteinases, Gelatinase and C ollagenase, in Chronic Leg Ulcers", *The Journal of Investigative Dermatology*, 106 (5), (1996), 1119-1123.

Will, H., et al., "The soluble catalytic domain of membrane type 1 matrix metalloproteinase cleaves the propeptide of progelatinase A and initiates autoproteolytic activation. Regulation by TIMP-2 and TIMP-3", *J. Biol. Chem.*, 271 (29), (1996), 17119-17123.

Wojtowicz-Praga, Slawomir M., "Matrix Metalloproteinase Inhibitors", *Investigative New Drugs*, 15, (1997), 61-75.

Wysocki, Annette B., et al., "Wound Fluid From Chronic Leg Ulcers Contains Elevated Levels Of Metalloproteinases MMP-2 and MMP-9", *The Journal of Investigative Dermatology*, 101 (1), (1993), 64-68.

Wysocki, Annette B., "Wound fluids and the pathogenesis of chronic wounds", *Journal of WOCN*, 23 (6), (1996), 283-290.

"Protein Sequence Information, Registry No. 116579-75-0, Accession No. 134: 142800", *Database CAplus, ACS on STN* (Chemical Abstracts Service) (2004), 1 pg.

Coppola, G., et al., "Effect of Intraperitoneally, Intravenously and Intralesionally Administered Monoclonal Anti-β-FGF Antibodies on Rat Chondrosarcoma Tumour Vascularization and Growth", *Anticancer Research*, 17(3C), (1997),2033-2040.

Dailey, L., et al., "A Network of Transcriptional and Signaling Events is Activatd by FGF to Induce Chondrocyte Growth Arrest and Differentiation", *The Journal of Cell Biology*, 161(6), (2003), 1053-1066.

Fujisawa, N., et al., "Inhibitory Effects of Transforming Growth Factor—β1 Pretreatment on Experimental Pulmonary Metastasis of MCS-1 Chinese Hamster Messenchymal Chondrosarcoma Cells", *Tohoku J. Exp. Med.*, 187, (1999),203-213.

Gigant-Huselstein, C., et al., "*In vitro* Study of Intracellular IL-1β Production and β1 Integrins Expression in Stimulated Chondrocytes—Effect of Rhein", *Biorheology*, 39(1, 2), (2002),277-285.

Kearns, A. E., "Initiation of Chondroitin Sulfate Biosynthesis: A Kinetic Analysis of $UDP_D$-Xylose: Core Protein $\beta_D$-Xylosyltransferase", *Biochemistry*, 30(30), (1991), 7477-7483.

Liacini, A., et al., "Induction of Matrix Metalloproteinase-13 Gene Expression by TNF-α is Mediated by MAP Kinases, AP-1, and NF-κB Transcription Factors in Articular Chondrocytes", *Experimental Cell Research*, 288(1), (2003),208-217.

Raucci, A., et al., "Activation of the ERK½ and p38 Mitogen-Activated Protein Kinase Pathways Mediates Fibroblast Growth Factor-Induced Growth Arrest of Chondrocytes", *The Journal of Biological Chemistry*, 279(3), (2004), 1747-1756.

Rodriguez-Manzaneque, J. C., et al., "ADAMTS1 Cleaves Aggrecan at Multiple Sites and is Differentially Inhibited by Metalloproteinase Inhibitors", *Biochemical and Biophysical Research Communications*, 293(1), (2002),501-508.

Sahni, M., et al., "FGF Signaling Inhibits Chondrocyte Proliferation and Regulates Bone Development Through the STAT-1 Pathway", *Genes & Development*, 13(11), (1999),1361-1366.

Seong, S.-C., et al., "Insulin-Line Growth Factor I Regulation of Swarm Rat Chondrosarcoma Chondrocytes in Culture", *Experimental Cell Research*, 211, (1994),238-244.

Wu, C., et al., "Furin-Mediated Processing of Pro-C-Type Natriuretic Peptide", *The Journal of Biological Chemistry*, 278(28), (2003),25847-25852.

```
mmp2  : MQKFFGLPQTGDLDQNTIETMRKPRCGNPDVANYNFFPRKPKWD---------
mmp13 : MQSFFGLEVTGKLDDNTLDVMKKPRCGVPDVGEYNVFPRTLKWSKMNLTY----
mmp7  : MQKFFGLPETGKLSPRVMEIMQKPRCGVPDVAEFSLMPNSPKWHSRTVTYRIVSYT
mmp3  : MQKFLGLEVTGKLDSDTLEVMRKPRCGVPDVGHFRTFPGIPKWRKTHLTYRIVN-
mmp10 : MQKFLGLEVTGKLDTDTLEVMRKPRCGVPDVGHFSSFPGMPKWRKTHLTYRIVNY-
mmp12 : MQHFLGLKVTGQLDTSTLEMMHAPRCGVPDVHHFREMPGGPVWRKHYITYRINN-
mmp9  : LQKQLSLPETGELDSATLKAMRTPRCGVPDLGRFQTFEGDLKWHHHN-------
mmp1  : MQEFFGLKVTGKPDAETLKVMKQPRCGVPDVAQFVLTEGNPRWEQTHLTYRIEN-
mmp8  : MQRFFGLNVTGKPNEETLDMMKKPRCGVPDSGGFMLTPGNPKWERTNLTYRIRNY-
        :* :.:** :** :: :  *      *******: :.   . ::  :****.:

Fig. 1A mmp2  : MQKFFGLPQTGDLDQNTIETMRKPRCGNPDVANYNFFPRKPKWD---------
mmp13 : MQSFFGLEVTGKLDDNTLDVMKKPRCGVPDVGEYNVFPRTLKWSKMNLTY----
mmp7  : MQKFFGLPETGKLSPRVMEIMQKPRCGVPDVAEFSLMPNSPKWHSRTVTYRIVSYT
mmp3  : MQKFLGLEVTGKLDSDTLEVMRKPRCGVPDVGHFRTFPGIPKWRKTHLTYRIVN-
mmp10 : MQKFLGLEVTGKLDTDTLEVMRKPRCGVPDVGHFSSFPGMPKWRKTHLTYRIVNY-
mmp12 : MQHFLGLKVTGQLDTSTLEMMHAPRCGVPDVHHFREMPGGPVWRKHYITYRINN-
mmp9  : LQKQLSLPETGELDSATLKAMRTPRCGVPDLGRFQTFEGDLKWHHHN-------
mmp1  : MQEFFGLKVTGKPDAETLKVMKQPRCGVPDVAQFVLTEGNPRWEQTHLTYRIEN-
mmp8  : MQRFFGLNVTGKPNEETLDMMKKPRCGVPDSGGFMLTPGNPKWERTNLTYRIRNY-
```

Fig. 1B

ANTI-CHRONDROSARCOMA COMPOUNDS

CROSS REFERENCE TO RELATED APPLICATIONS

This application is related to the following co-pending applications, which are all assigned to a common assignee:
U.S. application Ser. No. 10/335,207, filed Dec. 30, 2002,
U.S. application Ser. No. 10/219,329, filed Aug. 15, 2002,
PCT Application No. PCT/US02/26319 filed Aug. 15, 2002,
U.S. application Ser. No. 10/153,185, filed May 21, 2002,
U.S. application Ser. No. 10/032,376, filed Dec. 21, 2001,
U.S. Provisional Patent Application Ser. No. 60/312,726, filed Aug. 16, 2001, the contents of which applications are hereby incorporated by reference in their entirety.

FIELD OF THE INVENTION

The invention relates to formulations containing inhibitors of matrix metalloproteinases that are useful for treating chrondrosarcomas that may give rise to bone malignancies. The inhibitors are peptides having sequences related to the cleavage site of the proenzyme forms of matrix metalloproteinases.

BACKGROUND OF THE INVENTION

The matrix metalloproteinases (MMPs) include a family of structurally similar zinc-dependent enzymes that degrade all of the major components of the extracellular matrix. MMPs include the collagenases, gelatinases A and B, the stromelysins, matrilysin, metalloelastase, and the membrane-type matrix metalloproteinases. Over-expression and activation of MMPs have been linked to development of several diseases, such as arthritis, cancer, and multiple sclerosis. Although MMPs classically have been implicated in basement membrane destruction associated with late-stage tumor cell invasion and metastasis, one MMP member, matrilysin, has recently been shown to be expressed in early stage human colorectal tumors. (C. L. Wilson et al., Proc. Natl. Acad. Sci. USA 94:1402–1407 (February 1997)). Expression of MMPs in human chrondrosarcoma cells has been reported. Soderstrom et al. (2001) APMIS 109:305–15; Kerkela et al. (2001) Bone 29:487–93; Sakamoto et al. (1999) J. Cancer Res. Clin. Oncol. 125:541–48.

Chondrosarcoma usually occurs in late adulthood or old age, and is the second most common form of bone malignancy. Conventional chondrosarcoma tumors are graded from stage I through stage III, with stage III being the most advanced. In addition to conventional chondrosarcoma, there are other types of chondrosarcoma with distinguishing characteristics: myxoid, mesenchymal, clear cell, and dedifferentiated (spindle cell) chondrosarcoma.

Consequently, a need exists for agents that can inhibit the growth and spread of chrondrosarcoma cells.

SUMMARY OF THE INVENTION

The invention provides anti-chrondrosarcoma compositions and methods that decrease growth of chondrosarcoma cells. Such methods and compositions are useful for a variety of therapeutic purposes. For example, the compositions and methods of the invention can be used to treat cancer, including chrondrosarcomas and bone cancers. The peptides of the invention inhibit metalloproteinases as well as diminishing the growth of chrondrosarcoma cells. Various parenterally and non-parenterally administered compositions are contemplated, as well as methods of using the peptides to inhibit tumor growth and development.

The present invention is therefore directed to peptide inhibitors of matrix metalloproteinases for inhibiting chondrosarcoma cell growth. These peptide inhibitors have amino acid sequences identical or related to the linking region spanning the two globular domains of matrix metalloproteinases. Several types of matrix metalloproteinases and their sequences are known, including matrix metalloproteinase-1, matrix metalloproteinase-2, matrix metalloproteinase-3, matrix metalloproteinase-4, matrix metalloproteinase-5, matrix metalloproteinase-6, matrix metalloproteinase-7, matrix metalloproteinase-8, and matrix metalloproteinase-9, matrix metalloproteinase-10, matrix metalloproteinase-11, matrix metalloproteinase-12, and matrix metalloproteinase-13. The invention contemplates inhibitors having amino acid sequences from the linking region of any of the matrix metalloproteinases. For example, peptide inhibitors of the invention can have amino acid sequences drawn from any region from about amino acid 70 to about amino acid 120 of the matrix metalloproteinase-2 sequence (SEQ ID NO:14), and analogous regions of all other matrix metalloproteinases.

The invention provides peptides of any one of formulae (I), (II), (III):

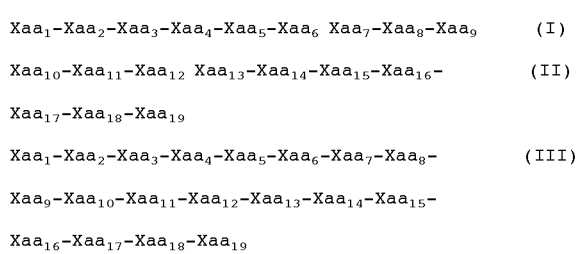

Wherein:
Xaa$_1$, Xaa$_4$, and Xaa$_6$ are separately each apolar amino acids;
Xaa$_2$ is a basic amino acid;
Xaa$_3$ is a cysteine-like amino acid;
Xaa$_5$ is a polar or aliphatic amino acid;
Xaa$_7$ is an acidic amino acid,
Xaa$_8$ is an aliphatic or polar amino acid;
Xaa$_9$ is an aliphatic, apolar or basic amino acid;
Xaa$_{10}$ is a polar, acidic, basic or apolar amino acid;
Xaa$_{11}$ is a polar or aromatic amino acid;
Xaa$_{12}$ is a polar, basic, aliphatic or apolar amino acid;
Xaa$_{13}$ is an aromatic, aliphatic, polar or acidic amino acid;
Xaa$_{14}$ is an aromatic, apolar or polar amino acid;
Xaa$_{15}$ is an apolar or acidic amino acid;
Xaa$_{16}$ is a basic, a polar or an apolar amino acid;
Xaa$_{17}$ is a basic, a polar, an aliphatic, an apolar or an acidic amino acid;
Xaa$_{18}$ is an apolar or an aliphatic amino acid;
Xaa$_{19}$ is a basic or an aliphatic amino acid; and wherein the peptide is capable of inhibiting the activity of matrix metalloproteinase-1, matrix metalloproteinase-2, matrix metalloproteinase-3, matrix metalloproteinase-4, matrix metalloproteinase-5, matrix metalloproteinase-6, matrix metalloproteinase-7, matrix metalloproteinase-8, or matrix metalloproteinase-9, matrix metalloproteinase-10, matrix metalloproteinase-11, matrix metalloproteinase-12, and matrix metalloproteinase-13. In some embodiments, the peptide can inhibit the activity of matrix metalloproteinase-2, matrix metalloproteinase-3, matrix metalloproteinase-7, matrix metalloproteinase-8, or matrix metalloproteinase-9.

An apolar amino acid can be, for example, methionine, glycine or proline. A basic amino acid, for example, can be histidine, lysine, arginine, 2,3-diaminopropionic acid, ornithine, homoarginine, ?-aminophenylalanine, or 2,4-diaminobutyric acid. Cysteine-like amino acids of the invention include, for example, cysteine, homocysteine, penicillamine, or β-methyl cysteine.

Aliphatic amino acids include, for example, alanine, valine, leucine, isoleucine, t-butylalanine, t-butylalanine, N-methylisoleucine, norleucine, N-methylvaline, cyclohexylalanine, β-alanine, N-methylglycine, or a-aminoisobutyric acid. Acidic amino acids include, for example, aspartic acid or glutamic acid. Polar amino acids include, for example, asparagine, glutamine, serine, threonine, tyrosine, citrulline, N-acetyl lysine, methionine sulfoxide, or homoserine, or an apolar amino acid such as methionine, glycine or proline. Aromatic amino acids of the invention can be, for example, phenylalanine, tyrosine, tryptophan, phenylglycine, naphthylalanine, β-2-thienylalanine, 1,2,3,4-tetrahydro-isoquinoline-3-carboxylic acid, 4-chlorophenylalanine, 2-fluorophenylalanine, 3-fluorophenylalanine, 4-fluorophenylalanine, pyridylalanine, or 3-benzothienyl alanine.

The invention also provides peptides of formula (IV) (SEQ ID NO:18):

$Xaa_a-Xaa_b-Xaa_c-Xaa_d-Xaa_e-Xaa_f-Xaa_g-Xaa_h-Xaa_i-$ (IV)

$Xaa_j-Xaa_k-Xaa_L-Xaa_m-Xaa_n-Xaa_o-Xaa_p-Xaa_1-Xaa_2-$ $Xaa_3-Xaa_4-Xaa_5-Xaa_6-Xaa_7-Xaa_8-Xaa_9-Xaa_{10}-$ $Xaa_{11}-Xaa_{12}-Xaa_{13}-Xaa_{14}-Xaa_{15}-Xaa_{16}-Xaa_{17}-$ $Xaa_{18}-Xaa_{19}$ wherein:

| | |
|---|---|
| $Xaa_a$ is proline; | $Xaa_1$ is proline; |
| $Xaa_b$ is glutamine or glutamic acid; | $Xaa_2$ is arginine; |
| $Xaa_c$ is threonine; | $Xaa_3$ is cysteine; |
| $Xaa_d$ is glycine; | $Xaa_4$ is glycine; |
| $Xaa_e$ is aspartic acid or glutamic acid; | $Xaa_5$ is valine or asparagine; |
| $Xaa_f$ is leucine; | $Xaa_6$ is proline; |
| $Xaa_g$ is aspartic acid; | $Xaa_7$ is aspartic acid; |
| $Xaa_h$ is glutamine or serine; | $Xaa_8$ is valine or leucine; |
| $Xaa_i$ is asparagine or alanine; | $Xaa_9$ is alanine or glycine; |
| $Xaa_j$ is threonine; | $Xaa_{10}$ is asparagine or arginine; |
| $Xaa_k$ is isoleucine or leucine; | $Xaa_{11}$ is tyrosine or phenylalanine; |
| $Xaa_L$ is glutamic acid or lysine; | $Xaa_{12}$ is asparagine or glutamine; |
| $Xaa_m$ is threonine or alanine; | $Xaa_{13}$ is phenylalanine or threonine; |
| $Xaa_n$ is methionine; | $Xaa_{14}$ is phenylalanine; |
| $Xaa_o$ is arginine; | $Xaa_{15}$ is proline or glutamic acid; |
| $Xaa_p$ is lysine or threonine; | $Xaa_{16}$ is arginine or glycine; |
| $Xaa_{17}$ is lysine or aspartic acid; | $Xaa_{18}$ is proline or leucine; |
| $Xaa_{19}$ is lysine; and | | wherein the peptide is capable of inhibiting the activity of a metalloproteinase. For example, the matrix metalloproteinase can be matrix metalloproteinase-1, matrix metalloproteinase-2, matrix metalloproteinase-3, matrix metalloproteinase-4, matrix metalloproteinase-5, matrix metalloproteinase-6, matrix metalloproteinase-7, matrix metalloproteinase-8, and matrix metalloproteinase-9, matrix metalloproteinase-10, matrix metalloproteinase-11, matrix metalloproteinase-12, or matrix metalloproteinase-13. Desirable peptides inhibit matrix metalloproteinase-2 or matrix metalloproteinase-9.

Regions from which peptide inhibitors of the invention can be derived, for example, from amino acid sequences ranging from about position 70 to about position 120 of SEQ ID NO:14, and analogous regions of other matrix metalloproteinases. In some embodiments the peptide inhibitors of the invention have amino acid sequences ranging from about position 77 to about position 110 of SEQ ID NO:14, and analogous regions or other matrix metalloproteinases. Examples of peptide inhibitors that can be used in the invention include those that contain amino acid sequences SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, or SEQ ID NO:13.

Peptides of the invention have varying affinities for the different matrix metalloproteinases. For example, in one embodiment, the peptide inhibitors can inhibit matrix metalloproteinase-2 with a ki of about 1.0 μM to about 500.0 μM. In another embodiment, the peptide inhibitors can inhibit matrix metalloproteinase-2 with a ki of about 1.0 μM to about 400.0 μM. In yet another embodiment, the peptide inhibitors can inhibit matrix metalloproteinase-2 with a ki of about 1.0 μM to about 50.0 μM.

The invention further provides compositions that can decrease growth of chrondrosarcoma cells that include an effective amount of peptide of the invention and a pharmaceutically acceptable carrier. Such compositions are useful for treating a variety of bone cancers, chrondrosarcomas and other diseases.

The invention further provides a method for decreasing growth of chrondrosarcoma cells that comprises contacting a chrondrosarcoma cell with an effective amount of a peptide of formula I, II, III or IV:

(SEQ ID NO:21)
$Xaa_1-Xaa_2-Xaa_3-Xaa_4-Xaa_5-Xaa_6\ Xaa_7-Xaa_8-Xaa_9$ (I)

$Xaa_{10}-Xaa_{11}-Xaa_{12}-Xaa_{13}-Xaa_{14}-Xaa_{15}-Xaa_{16}-$ (II)

$Xaa_{17}-Xaa_{18}-Xaa_{19}$ $Xaa_1-Xaa_2-Xaa_3-Xaa_4-Xaa_5-Xaa_6-Xaa_7-Xaa_8-$ (III)

$Xaa_9-Xaa_{10}-Xaa_{11}-Xaa_{12}-Xaa_{13}-Xaa_{14}-Xaa_{15}-$ $Xaa_{16}-Xaa_{17}-Xaa_{18}-Xaa_{19}$ $Xaa_a-Xaa_b-Xaa_c-Xaa_d-Xaa_e-Xaa_f-Xaa_g-Xaa_h-$ (IV)

$Xaa_i-Xaa_j-Xaa_k-Xaa_L-Xaa_m-Xaa_n-Xaa_o-Xaa_p-$ $Xaa_1-Xaa_2-Xaa_3-Xaa_4-Xaa_5-Xaa_6-Xaa_7-Xaa_8-$ $Xaa_9-Xaa_{10}-Xaa_{11}-Xaa_{12}-Xaa_{13}-Xaa_{14}-Xaa_{15}-$ $Xaa_{16}-Xaa_{17}-Xaa_{18}-Xaa_{19}$ wherein:

$Xaa_1$, $Xaa_4$, and $Xaa_6$ are separately each apolar amino acids;

$Xaa_2$ is a basic amino acid;

$Xaa_3$ is a cysteine-like amino acid;

$Xaa_5$ is a polar or aliphatic amino acid;

$Xaa_7$ is an acidic amino acid, $Xaa_8$ is an aliphatic or polar amino acid;

$Xaa_9$ is an aliphatic, apolar or basic amino acid; and

Xaa$_{10}$ is a polar, acidic, basic or apolar amino acid;
Xaa$_{11}$ is a polar or aromatic amino acid;
Xaa$_{12}$ is a polar, basic, aliphatic or apolar amino acid;
Xaa$_{13}$ is an aromatic, aliphatic, polar or acidic amino acid;
Xaa$_{14}$ is an aromatic, apolar or polar amino acid;
Xaa$_{15}$ is an apolar or acidic amino acid;
Xaa$_{16}$ is a basic, a polar or an apolar amino acid;
Xaa$_{17}$ is a basic, a polar, an aliphatic, an apolar or an acidic amino acid;
Xaa$_{18}$ is an apolar or an aliphatic amino acid;
Xaa$_{19}$ is a basic or an aliphatic amino acid;
Xaa$_a$ is proline;
Xaa$_b$ is glutamine or glutamic acid;
Xaa$_c$ is threonine;
Xaa$_d$ is glycine;
Xaa$_e$ is aspartic acid or glutamic acid;
Xaa$_f$ is leucine;
Xaa$_g$ is aspartic acid;
Xaa$_h$ is glutamine or serine;
Xaa$_i$ is asparagine or alanine;
Xaa$_j$ is threonine;
Xaa$_k$ is isoleucine or leucine;
Xaa$_L$ is glutamic acid or lysine;
Xaa$_m$ is threonine or alanine;
Xaa$_n$ is methionine;
Xaa$_o$ is arginine; and
Xaa$_p$ is lysine or threonine;

wherein the peptide is capable of inhibiting the activity of a matrix metalloproteinase.

An apolar amino acid in the peptides of the invention can be, for example, methionine, glycine or proline. The basic amino acid can be, for example, histidine, lysine, arginine, 2,3-diaminopropionic acid, ornithine, homoarginine, ?-aminophenylalanine, and 2,4-diaminobutyric acid. The cysteine-like amino acid can be, for example, cysteine, homocysteine, penicillamine, or β-methyl cysteine. The aliphatic amino acid can be, for example, alanine, valine, leucine, isoleucine, t-butylalanine, t-butylalanine, N-methylisoleucine, norleucine, N-methylvaline, cyclohexylalanine, β-alanine, N-methylglycine, or a-aminoisobutyric acid. The acidic amino acid can be, for example, aspartic acid or glutamic acid. A polar amino acid can be asparagine, glutamine, serine, threonine, tyrosine, citrulline, N-acetyl lysine, methionine sulfoxide, or homoserine, or an apolar amino acid such as methionine, glycine or proline. An aromatic amino acid is phenylalanine, tyrosine, tryptophan, phenylglycine, naphthylalanine, β-2-thienylalanine, 1,2,3,4-tetrahydro-isoquinoline-3-carboxylic acid, 4-chlorophenylalanine, 2-fluorophenylalanine, 3-fluorophenylalanine, 4-fluorophenylalanine, pyridylalanine, or 3-benzothienyl alanine.

In another embodiment the invention provides a method for inhibiting the growth and/or development of a tumor (e.g. a chrondrosarcoma) that comprises administering a therapeutically effective amount of a peptide of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, or SEQ ID NO:13.

DESCRIPTION OF THE FIGURES

FIG. 1 provides a CLUSTAL X (version 1.8) multiple sequence alignment of the cleavage spanning regions of select MMP proenzymes (SEQ ID NOs:2–10. FIG. 1A provides an alignment that highlights conserved residues where an '*' indicates complete identity among the sequences, a ':' indicates 7/9 conserved positions, and a '.' indicates greater than 80% identical positions with mostly conserved substitutions. FIG. 1B indicates the positions of heterogeneity in bold.

FIG. 14 provides an isothermal titration calorimetry analysis of the interaction of the 19-mer (SEQ ID NO:11) inhibitor peptide with MMP-2.

DETAILED DESCRIPTION OF THE INVENTION

Figure 2:
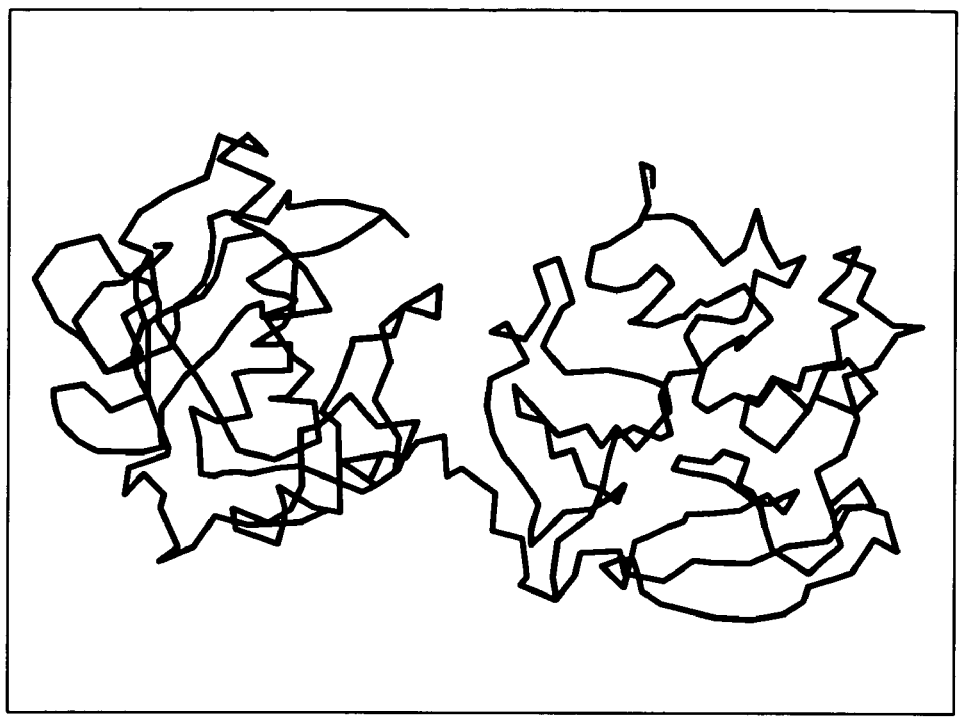
FIG. 2 provides the structure of proMMP-1 (Protein databank file 1FBL.ENT). The area of SEQ ID NOS:2–10 shown in Table 1 spans the short region between the two large domains. During activation this region is cleaved.

The present invention provides inhibitors of matrix metalloproteinases that are useful for decreasing growth and progression of cancers such as chondrosarcomas.

Matrix metalloproteinases are produced in vivo as inactive proenzymes. Proteolytic cleavage of the proenzyme results in activation and formation of the mature matrix metalloproteinase. The peptide sequence that is cleaved off is a proenzyme leader sequence of approximately 100 to 110 amino acids in length that is found at the extreme amino terminus of the protein. According to the invention, these proenzyme leader peptides can block the matrix metalloproteinases active site and inhibit the activity of the matrix metalloproteinase. Administration of matrix metalloproteinase proenzyme leader peptides reduces the rate of extracellular matrix destruction and provides a faster rate of wound healing.

Most inhibition strategies involve preventing enzymatic activity of matrix metalloproteinases with organic small molecules. These compounds are often toxic to the body and are not naturally occurring molecules. Use of natural peptides to inhibit activated matrix metalloproteinases provides a high degree of proteinase control without toxic side effects. Unlike small molecule inhibition strategies, the peptides of the invention can be used to inhibit activation of individual or all matrix metalloproteinase classes simultaneously. The peptides can be freely administered to a mammal, injected into a tumor or cancer site, or introduced onto an appropriate tissue, for example, into the bone.

The invention provides a high degree of control over the level of proteinase activity for treating and preventing the spread of cancer. For example, as some amount of proteinase activity may be required for some basic physiological processes such as wound healing (Agren et al., 1999), one of skill in the art may choose to only partially inhibit proteinase activity. By modulating the type and amount of inhibitor peptide applied, the degree of matrix metalloproteinase inhibition can be controlled.

Peptide Inhibitors

According to the present invention, peptides having sequences related to a matrix metalloproteinase proenzyme leader in the region of the cleavage site will inhibit the activity of many types of matrix metalloproteinases. The cleavage position is at about amino acid position 110 of the proenzyme amino acid sequence. Peptide inhibitors of the invention have sequences related to any region within proenzyme amino acid position 70 to about amino acid position 120. Such peptides will inhibit the activity of many types of matrix metalloproteinases. The present peptides can also prevent the activation of proenzyme matrix metalloproteinases, as well as inhibit the enzymatic activity of mature matrix metalloproteinases. Peptides containing sequences that are more conserved in a variety of matrix metalloproteinases, for example, sequences toward the N-terminal side of the cleavage region, can be used to provide inhibitors that are generally effective against a variety of matrix metalloproteinases. However, peptides containing sequences that are less conserved, for example, sequences toward the C-terminal side of the cleavage region, can be used to provide inhibitors that are specific for individual matrix metalloproteinases.

Hence, peptides with sequences from any proenzyme leader region of a matrix metalloproteinase are contemplated by the invention as inhibitors of matrix metalloproteinases, as well as variant peptides that have one or more amino acids substituted for the amino acids that are naturally present in the matrix metalloproteinase. Mixtures of peptides with different sequences are also contemplated.

In general, the peptides, peptide variants, peptide derivatives, and mixtures of peptides are formulated and used in a manner that optimizes prevention of tumor formation, optimizes tumor reduction, optimizes wound healing, or optimizes the regeneration of healthy, non-cancerous tissues. Hence, the composition and formulations of the present peptides can be varied so that lesser or greater levels of inhibition are achieved so long as tumor development is inhibited and healing is promoted.

The size of a peptide inhibitor can vary. In general, a peptide of only about five amino acids can be too small to provide optimal inhibition. However, peptides of more than about eight to nine amino acids are sufficiently long to provide inhibition. Therefore, while the overall length is not critical, peptides longer than about eight amino acids are desirable. Desirable peptides can also be longer than about nine amino acids, longer than about ten amino acids or even longer than about fifteen amino acids.

There is no particular upper limit on peptide size. However, it is generally cheaper to make shorter peptides than longer peptides. Hence, the peptide inhibitors of the invention are generally shorter than about one hundred amino acids. Desirable peptide inhibitors can also be shorter than about fifty amino acids, shorter than about thirty amino acids, or shorter than about twenty five amino acids. In some embodiments, the peptides are shorter than about twenty three amino acids. An example of a peptide of the invention is a peptide having SEQ ID NO:11, with nineteen amino acids.

The sequences of several representative matrix metalloproteinases from about proenzyme amino acid position 70 to about amino acid position 120 are provided in Table 1.

TABLE 1

Sequences of Matrix Metalloproteinase Cleavage Regions

| MMP | Sequence | SEQ ID |
|---|---|---|
| mmp2 | MQKFFGLPQTGDLDQNTIETMRKPRCGNPDVA NYNFFPRKPKWD | NO:2 |

TABLE 1-continued

Sequences of Matrix Metalloproteinase Cleavage Regions

| MMP | Sequence | SEQ ID |
|---|---|---|
| mmp13 | MQSFFGLEVTGKLDDNTLDVMKKPRCGVPDV GEYNVFPRTLKWSKMNLTY | NO:3 |
| mmp7 | MQKFFGLPETGKLSPRVMEIMQKPRCGVPDVA EFSLMPNSPKWHSRTVTYRIVSYT | NO:4 |
| mmp3 | MQKFLGLEVTGKLDSDTLEVMRKPRCGVPDV GHFRTFPGIPKWRKTHLTYRIVN | NO:5 |
| mmp10 | MQKFLGLEVTGKLDTDTLEVMRKPRCGVPDV GHFSSFPGMPKWRKTHLTYRIVNY | NO:6 |
| mmp12 | MQHFLGLKVTGQLDTSTLEMMHAPRCGVPDV HHFREMPGGPVWRKHYITYRINN | NO:7 |
| mmp9 | LQKQLSLPETGELDSATLKAMRTPRCGVPDLG RFQTFEGDLKWHHHN | NO:8 |
| mmp1 | MQEFFGLKVTGKPDAETLKVMKQPRCGVPDV AQFVLTEGNPRWEQTHLTYRIEN | NO:9 |
| mmp8 | MQRFFGLNVTGKPNEETLDMMKKPRCGVPDS GGFMLTPGNPKWERTNLTYRIRNY | NO:10 |

Each of the peptides listed in Table 1, as well as peptides with SEQ ID NO:1, 11, 12 and 13, are contemplated as peptide inhibitors of the invention. Moreover, peptide variants and derivatives of the peptides having any of SEQ ID NO: 1–13 are also useful as peptide inhibitors. Such peptide variants and derivatives can have one or more amino acid substitutions, deletions, insertions or other modifications so long as the peptide variant or derivative can inhibit a matrix metalloproteinase.

Amino acid residues of the isolated peptides can be genetically encoded L-amino acids, naturally occurring non-genetically encoded L-amino acids, synthetic L-amino acids or D-enantiomers of any of the above. The amino acid notations used herein for the twenty genetically encoded L-amino acids and common non-encoded amino acids are conventional and are as shown in Table 2.

TABLE 2

| Amino Acid | One-Letter Symbol | Common Abbreviation |
|---|---|---|
| Alanine | A | Ala |
| Arginine | R | Arg |
| Asparagine | N | Asn |
| Aspartic acid | D | Asp |
| Cysteine | C | Cys |
| Glutamine | Q | Gln |
| Glutamic acid | E | Glu |
| Glycine | G | Gly |
| Histidine | H | His |
| Isoleucine | I | Ile |
| Leucine | L | Leu |
| Lysine | K | Lys |
| Methionine | M | Met |

TABLE 2-continued

| Amino Acid | One-Letter Symbol | Common Abbreviation |
|---|---|---|
| Phenylalanine | F | Phe |
| Proline | P | Pro |
| Serine | S | Ser |
| Threonine | T | Thr |
| Tryptophan | W | Trp |
| Tyrosine | Y | Tyr |
| Valine | V | Val |
| β-Alanine | | bAla |
| 2,3-Diaminopropionic acid | | Dpr |
| a-Aminoisobutyric acid | | Aib |
| N-Methylglycine (sarcosine) | | MeGly |
| Ornithine | | Orn |
| Citrulline | | Cit |
| t-Butylalanine | | t-BuA |
| t-Butylglycine | | t-BuG |
| N-methylisoleucine | | MeIle |
| Phenylglycine | | Phg |
| Cyclohexylalanine | | Cha |
| Norleucine | | Nle |
| Naphthylalanine | | Nal |
| Pyridylalanine | | |
| 3-Benzothienyl alanine | | |
| 4-Chlorophenylalanine | | Phe(4-Cl) |
| 2-Fluorophenylalanine | | Phe(2-F) |
| 3-Fluorophenylalanine | | Phe(3-F) |
| 4-Fluorophenylalanine | | Phe(4-F) |
| Penicillamine | | Pen |
| 1,2,3,4-Tetrahydro-isoquinoline-3-carboxylic acid | | Tic |
| β-2-thienylalanine | | Thi |
| Methionine sulfoxide | | MSO |
| Homoarginine | | hArg |
| N-acetyl lysine | | AcLys |
| 2,4-Diamino butyric acid | | Dbu |
| ?-Aminophenylalanine | | Phe(pNH$_2$) |
| N-methylvaline | | MeVal |
| Homocysteine | | hCys |
| Homoserine | | hSer |
| e-Amino hexanoic acid | | Aha |
| d-Amino valeric acid | | Ava |
| 2,3-Diaminobutyric acid | | Dab |

Peptides that are encompassed within the scope of the invention can have one or more amino acids substituted with an amino acid of similar chemical and/or physical properties, so long as these variant or derivative peptides retain the ability to inhibit the activity of a matrix metalloproteinase.

Amino acids that are substitutable for each other generally reside within similar classes or subclasses. As known to one of skill in the art, amino acids can be placed into three main classes: hydrophilic amino acids, hydrophobic amino acids and cysteine-like amino acids, depending primarily on the characteristics of the amino acid side chain. These main classes may be further divided into subclasses. Hydrophilic amino acids include amino acids having acidic, basic or polar side chains and hydrophobic amino acids include amino acids having aromatic or apolar side chains. Apolar amino acids may be further subdivided to include, among others, aliphatic amino acids. The definitions of the classes of amino acids as used herein are as follows:

"Hydrophobic Amino Acid" refers to an amino acid having a side chain that is uncharged at physiological pH and that is repelled by aqueous solution. Examples of genetically encoded hydrophobic amino acids include Ile, Leu and Val. Examples of non-genetically encoded hydrophobic amino acids include t-BuA.

"Aromatic Amino Acid" refers to a hydrophobic amino acid having a side chain containing at least one ring having a conjugated p-electron system (aromatic group). The aromatic group may be further substituted with substituent groups such as alkyl, alkenyl, alkynyl, hydroxyl, sulfonyl, nitro and amino groups, as well as others. Examples of genetically encoded aromatic amino acids include phenylalanine, tyrosine and tryptophan. Commonly encountered non-genetically encoded aromatic amino acids include phenylglycine, 2-naphthylalanine, β-2-thienylalanine, 1,2,3,4-tetrahydroisoquinoline-3-carboxylic acid, 4-chlorophenylalanine, 2-fluorophenylalanine, 3-fluorophenylalanine and 4-fluorophenylalanine.

"Apolar Amino Acid" refers to a hydrophobic amino acid having a side chain that is generally uncharged at physiological pH and that is not polar. Examples of genetically encoded apolar amino acids include glycine, proline and methionine. Examples of non-encoded apolar amino acids include Cha.

"Aliphatic Amino Acid" refers to an apolar amino acid having a saturated or unsaturated straight chain, branched or cyclic hydrocarbon side chain. Examples of genetically encoded aliphatic amino acids include Ala, Leu, Val and Ile. Examples of non-encoded aliphatic amino acids include Nle.

"Hydrophilic Amino Acid" refers to an amino acid having a side chain that is attracted by aqueous solution. Examples of genetically encoded hydrophilic amino acids include Ser and Lys. Examples of non-encoded hydrophilic amino acids include Cit and hCys.

"Acidic Amino Acid" refers to a hydrophilic amino acid having a side chain pK value of less than 7. Acidic amino acids typically have negatively charged side chains at physiological pH due to loss of a hydrogen ion. Examples of genetically encoded acidic amino acids include aspartic acid (aspartate) and glutamic acid (glutamate).

"Basic Amino Acid" refers to a hydrophilic amino acid having a side chain pK value of greater than 7. Basic amino acids typically have positively charged side chains at physiological pH due to association with hydronium ion. Examples of genetically encoded basic amino acids include arginine, lysine and histidine. Examples of non-genetically encoded basic amino acids include the non-cyclic amino acids ornithine, 2,3-diaminopropionic acid, 2,4-diaminobutyric acid and homoarginine.

"Polar Amino Acid" refers to a hydrophilic amino acid having a side chain that is uncharged at physiological pH, but which has a bond in which the pair of electrons shared in common by two atoms is held more closely by one of the atoms. Examples of genetically encoded polar amino acids include asparagine and glutamine. Examples of non-genetically encoded polar amino acids include citrulline, N-acetyl lysine and methionine sulfoxide.

"Cysteine-Like Amino Acid" refers to an amino acid having a side chain capable of forming a covalent linkage with a side chain of another amino acid residue, such as a disulfide linkage. Typically, cysteine-like amino acids generally have a side chain containing at least one thiol (SH) group. Examples of genetically encoded cysteine-like amino acids include cysteine. Examples of non-genetically encoded cysteine-like amino acids include homocysteine and penicillamine.

As will be appreciated by those having skill in the art, the above classifications are not absolute. Several amino acids exhibit more than one characteristic property, and can therefore be included in more than one category. For example, tyrosine has both an aromatic ring and a polar hydroxyl group. Thus, tyrosine has dual properties and can be included in both the aromatic and polar categories. Similarly, in addition to being able to form disulfide linkages, cysteine also has apolar character. Thus, while not strictly classified as a hydrophobic or apolar amino acid, in many instances cysteine can be used to confer hydrophobicity to a peptide.

Certain commonly encountered amino acids that are not genetically encoded and that can be present, or substituted for an amino acid, in the peptides and peptide analogues of the invention include, but are not limited to, β-alanine (b-Ala) and other omega-amino acids such as 3-aminopropionic acid (Dap), 2,3-diaminopropionic acid (Dpr), 4-aminobutyric acid and so forth; a-aminoisobutyric acid (Aib); e-aminohexanoic acid (Aha); d-aminovaleric acid (Ava); methylglycine (MeGly); ornithine (Orn); citrulline (Cit); t-butylalanine (t-BuA); t-butylglycine (t-BuG); N-methylisoleucine (MeIle); phenylglycine (Phg); cyclohexylalanine (Cha); norleucine (Nle); 2-naphthylalanine (2-Nal); 4-chlorophenylalanine (Phe(4-Cl)); 2-fluorophenylalanine (Phe(2-F)); 3-fluorophenylalanine (Phe(3-F)); 4-fluorophenylalanine (Phe(4-F)); penicillamine (Pen); 1,2,3,4-tetrahydroisoquinoline-3-carboxylic acid (Tic); β-2-thienylalanine (Thi); methionine sulfoxide (MSO); homoarginine (hArg); N-acetyl lysine (AcLys); 2,3-diaminobutyric acid (Dab); 2,3-diaminobutyric acid (Dbu); p-aminophenylalanine (Phe(pNH$_2$)); N-methyl valine (MeVal); homocysteine (hCys) and homoserine (hSer). These amino acids also fall into the categories defined above.

The classifications of the above-described genetically encoded and non-encoded amino acids are summarized in Table 3, below. It is to be understood that Table 3 is for illustrative purposes only and does not purport to be an exhaustive list of amino acid residues that may comprise the peptides and peptide analogues described herein. Other amino acid residues that are useful for making the peptides and peptide analogues described herein can be found, e.g., in Fasman, 1989, CRC Practical Handbook of Biochemistry and Molecular Biology, CRC Press, Inc., and the references cited therein. Amino acids not specifically mentioned herein can be conveniently classified into the above-described categories on the basis of known behavior and/or their characteristic chemical and/or physical properties as compared with amino acids specifically identified.

TABLE 3

| Classification | Genetically Encoded | Genetically Non-Encoded |
|---|---|---|
| Hydrophobic | | |
| Aromatic | F, Y, W | Phg, Nal, Thi, Tic, Phe(4-Cl), Phe(2-F), Phe(3-F), Phe(4-F), Pyridyl Ala, Benzothienyl Ala |
| Apolar | M, G, P | |
| Aliphatic | A, V, L, I | t-BuA, t-BuG, MeIle, Nle, MeVal, Cha, bAla, MeGly, Aib |
| Hydrophilic | | |
| Acidic | D, E | |
| Basic | H, K, R | Dpr, Orn, hArg, Phe(p-NH$_2$), DBU, A$_2$ BU |
| Polar | Q, N, S, T, Y | Cit, AcLys, MSO, hSer |
| Cysteine-Like | C | Pen, hCys, β-methyl Cys |

Peptides of the invention can have any amino acid substituted by any similarly classified amino acid to create a variant or derivative peptide, so long as the peptide variant retains an ability to inhibit the activity of a matrix metalloproteinase.

In one embodiment, the peptide inhibitors of the invention include any one of peptide formulae I, II or III.

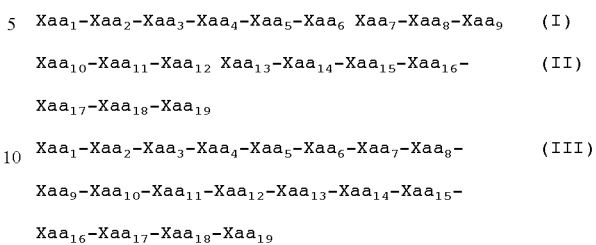

wherein

Xaa$_1$, Xaa$_4$, and Xaa$_6$ are separately each apolar amino acids, for example, methionine, glycine or proline;

Xaa$_2$ is a basic amino acid, for example, histidine, lysine, arginine, 2,3-diaminopropionic acid, ornithine, homoarginine, ?-aminophenylalanine, and 2,4-diaminobutyric acid;

Xaa$_3$ is a cysteine-like amino acid, for example, cysteine, homocysteine, penicillamine, or β-methyl cysteine;

Xaa$_5$ is a polar or aliphatic amino acid, for example, a polar amino such as asparagine, glutamine, serine, threonine, tyrosine, citrulline, N-acetyl lysine, methionine sulfoxide, or homoserine, or an aliphatic amino acid such as alanine, valine, leucine, isoleucine, t-butylalanine, t-butylalanine, N-methylisoleucine, norleucine, N-methylvaline, cyclohexylalanine, β-alanine, N-methylglycine, or a-aminoisobutyric acid;

Xaa$_7$ is an acidic amino acid, for example, aspartic acid or glutamic acid;

Xaa$_8$ is an aliphatic or polar amino acid, for example an aliphatic amino acid such as alanine, valine, leucine, isoleucine, t-butylalanine, t-butylalanine, methylisoleucine, norleucine, N-methylvaline, cyclohexylalanine, β-alanine, N-methylglycine, or a-aminoisobutyric acid, or a polar amino acid such as asparagine, glutamine, serine, threonine, tyrosine, citrulline, N-acetyl lysine, methionine sulfoxide, or homoserine;

Xaa$_9$ is an aliphatic, apolar or basic amino acid, for example, an aliphatic amino acid such as alanine, valine, leucine, isoleucine, t-butylalanine, t-butylalanine, N-methylisoleucine, norleucine, N-methylvaline, cyclohexylalanine, β-alanine, N-methylglycine, or a-aminoisobutyric acid, an apolar amino acid such as methionine, glycine or proline, or a basic amino acid such as histidine, lysine, arginine, 2,3-diaminopropionic acid, ornithine, homoarginine, ?-amino-phenylalanine, and 2,4-diaminobutyric acid;

Xaa$_{10}$ is a polar, acidic, basic or apolar amino acid, for example, a polar amino acid such as asparagine, glutamine, serine, threonine, tyrosine, citrulline, N-acetyl lysine, methionine sulfoxide, or homoserine, an acidic amino acid such as aspartic acid or glutamic acid, a basic amino acid such as histidine, lysine, arginine, 2,3-diaminopropionic acid, ornithine, homoarginine, ?-amino-phenylalanine, and 2,4-diaminobutyric acid, or an apolar amino acid such as methionine, glycine or proline;

Xaa$_{11}$ is a polar or aromatic amino acid, for example, a polar amino acid such as asparagine, glutamine, serine, threonine, tyrosine, citrulline, N-acetyl lysine, methionine sulfoxide, or homoserine, or an aromatic amino acid such as phenylalanine, tyrosine, tryptophan, phenylglycine, naphthylalanine, β-2-thienylalanine, 1,2,3,4-tetrahydro-isoquinoline-3-carboxylic acid, 4-chlorophenylalanine, 2-fluorophenylalanine, 3-fluorophenylalanine, 4-fluorophenylalanine, pyridylalanine, or 3-benzothienyl alanine;

$Xaa_{12}$ is a polar, basic, aliphatic or apolar amino acid, for example, a polar amino acid such asparagine, glutamine, serine, threonine, tyrosine, citrulline, N-acetyl lysine, methionine sulfoxide, or homoserine, or a basic amino acid such as histidine, lysine, arginine, 2,3-diaminopropionic acid, ornithine, homoarginine, ?-amino-phenylalanine, and 2,4-diaminobutyric acid, or an aliphatic amino acid such as alanine, valine, leucine, isoleucine, t-butylalanine, t-butylalanine, N-methylisoleucine, norleucine, N-methylvaline, cyclohexylalanine, β-alanine, N-methylglycine, or a-aminoisobutyric acid, or an apolar amino acid such as methionine, glycine or proline;

$Xaa_{13}$ is an aromatic, aliphatic, polar or acidic amino acid, for example, an aromatic amino acid such as phenylalanine, tyrosine, tryptophan, phenylglycine, naphthylalanine, β-2-thienylalanine, 1,2,3,4-tetrahydro-isoquinoline-3-carboxylic acid, 4-chlorophenylalanine, 2-fluorophenylalanine, 3-fluorophenylalanine, 4-fluorophenylalanine, pyridylalanine, or 3-benzothienyl alanine, or an aliphatic amino acid such as alanine, valine, leucine, isoleucine, t-butylalanine, t-butylalanine, N-methylisoleucine, norleucine, N-methylvaline, cyclohexylalanine, β-alanine, N-methylglycine, or a-aminoisobutyric acid, or a polar amino acid such as asparagine, glutamine, serine, threonine, tyrosine, citrulline, N-acetyl lysine, methionine sulfoxide, or homoserine, or an acidic amino acid such as aspartic acid or glutamic acid;

$Xaa_{14}$ is an aromatic, apolar or polar amino acid, for example, an aromatic amino acid such as phenylalanine, tyrosine, tryptophan, phenylglycine, naphthylalanine, β-2-thienylalanine, 1,2,3,4-tetrahydro-isoquinoline-3-carboxylic acid, 4-chlorophenylalanine, 2-fluorophenylalanine, 3-fluorophenylalanine, 4-fluorophenylalanine, pyridylalanine, or 3-benzothienyl alanine, or an apolar amino acid such as methionine, glycine or proline, or a polar amino acid such as asparagine, glutamine, serine, threonine, tyrosine, citrulline, N-acetyl lysine, methionine sulfoxide, or homoserine;

$Xaa_{15}$ is an apolar or acidic amino acid, for example, an apolar amino acid such as methionine, glycine or proline, or an acidic amino acid such as aspartic acid or glutamic acid;

$Xaa_{16}$ is a basic, a polar or an apolar amino acid, for example, a basic amino acid such as histidine, lysine, arginine, 2,3-diaminopropionic acid, ornithine, homoarginine, ?-amino-phenylalanine, and 2,4-diaminobutyric acid; or a polar amino acid such as asparagine, glutamine, serine, threonine, tyrosine, citrulline, N-acetyl lysine, methionine sulfoxide, or homoserine, or an apolar amino acid such as methionine, glycine or proline;

$Xaa_{17}$ is a basic, a polar, an aliphatic, an apolar or an acidic amino acid, for example, a basic amino acid such as histidine, lysine, arginine, 2,3-diaminopropionic acid, ornithine, homoarginine, ?-amino-phenylalanine, and 2,4-diaminobutyric acid, or a polar amino acid such as asparagine, glutamine, serine, threonine, tyrosine, citrulline, N-acetyl lysine, methionine sulfoxide, or homoserine, or an aliphatic amino acid such as alanine, valine, leucine, isoleucine, t-butylalanine, t-butylalanine, N-methylisoleucine, norleucine, N-methylvaline, cyclohexylalanine, β-alanine, N-methylglycine, or a-aminoisobutyric acid, or an apolar amino acid such as methionine, glycine or proline, or an acidic amino acid such as aspartic acid or glutamic acid;

$Xaa_{18}$ is an apolar or an aliphatic amino acid, for example, an apolar amino acid such as methionine, glycine or proline, or an aliphatic amino acid such as alanine, valine, leucine, isoleucine, t-butylalanine, t-butylalanine, N-methylisoleucine, norleucine, N-methylvaline, cyclohexylalanine, β-alanine, N-methylglycine, or a-aminoisobutyric acid; and $Xaa_{19}$ is a basic or an aliphatic amino acid, for example, a basic amino acid such as histidine, lysine, arginine, 2,3-diaminopropionic acid, ornithine, homoarginine, ?-amino-phenylalanine, and 2,4-diaminobutyric acid, or an aliphatic amino acid such as alanine, valine, leucine, isoleucine, t-butylalanine, t-butylalanine, N-methylisoleucine, norleucine, N-methylvaline, cyclohexylalanine, β-alanine, N-methylglycine, or a-aminoisobutyric acid.

In some embodiments:

$Xaa_1$ is proline,
$Xaa_2$ is arginine,
$Xaa_3$ is cysteine,
$Xaa_4$ is glycine,
$Xaa_5$ is valine or asparagine,
$Xaa_6$ is proline,
$Xaa_7$ is aspartic acid,
$Xaa_8$ is valine, leucine, or serine,
$Xaa_9$ is alanine, glycine or histidine,
$Xaa_{10}$ is asparagine, aspartic acid, histidine, arginine, glutamine or glycine,
$Xaa_{11}$ is tyrosine or phenylalanine,
$Xaa_{12}$ is asparagine, serine, arginine, glutamine, valine or methionine,
$Xaa_{13}$ is phenylalanine, valine, leucine, threonine, serine, or glutamic acid,
$Xaa_{14}$ is phenylalanine, methionine or threonine,
$Xaa_{15}$ is proline or glutamic acid,
$Xaa_{16}$ is arginine, asparagine or glycine,
$Xaa_{17}$ is lysine, threonine, serine, isoleucine, methionine, glycine, aspartic acid or asparagine,
$Xaa_{18}$ is proline or leucine, and
$Xaa_{19}$ is lysine, valine or arginine.

Desirable peptides of the invention also include the sequences defined by SEQ ID NO:1–13. One example of a desirable peptide is nineteen amino acid peptide having SEQ ID NO:11 (PRCGNPDVANYNFFPRKPK). This peptide (SEQ ID NO:11) spans the cleavage site of MMP-2. Two smaller peptides (PRCGNPDVA (SEQ ID NO:12) and NYNFFPRKPK (SEQ ID NO:13)), that represent approximate halves of the SEQ ID NO:11 peptide, are also desirable peptides. All three peptides inhibit MMP-9 activity and other matrix metalloproteinase enzymes to a varying degree.

A single peptide having a sequence identical to that of a matrix metalloproteinase cleavage region can be used to inhibit the activity of a single or a few matrix metalloproteinases. A formulation of such a single peptide will inhibit one or more, but generally not all, matrix metalloproteinase. Such partial inhibition of matrix metalloproteinase activity may facilitate healing. Alternatively, two or more peptides can be combined to target two or more matrix metalloproteinases that may provide more complete inhibition of matrix metalloproteinase activity.

One of skill in the art can design an appropriate peptide inhibitor or combination of peptide inhibitors to achieve the quality and quantity of inhibition desired using available teachings in combination with the teachings provided herein. "Quality" of inhibition refers to the type of matrix metalloproteinase inhibited. Different matrix metalloproteinases can have somewhat different substrates and sites of activity. "Quantity" of inhibition refers to the overall amount of inhibition from all matrix metalloproteinases. By modulating the type and quantity of peptide inhibitor used, the quality and quantity of inhibition can be modulated. One of skill in the art can readily make modifications to the peptides provided by the invention and observe the type and degree to which a given matrix metalloproteinase is inhibited.

For example, one of skill in the art can compare and align the peptide sequences shown in FIG. 1 and design a peptide inhibitor to achieve the quality and quantity of inhibition desired. In one embodiment, provided by way of example, the aligned amino acid sequences for three matrix metalloproteinases, mmp2, mmp9 and mmp1, are compared to identify regions of homology and regions of divergence in sequence.

| MMP | SEQUENCE | SEQ ID NO |
|---|---|---|
| mmp2: | MQKFFGLPQTGDLDQNTIETMRKPRCGNPDVANYNFFPRKPKWD | NO: 15 |
| mmp9: | LQKQLSLPETGELDSATLKAMRTPRCGVPDLGRFQTFEGDLKW | NO: 16 |
| mmp1: | MQEFFGLKVTGKPDAETLKVMKQPRCGVPD<u>VAQFVLT</u><u>EGN</u>P<u>R</u>W | NO: 17 |

In this sequence alignment, bold denotes amino acids found in MMP-1 that are not found in MMP-2 or MMP-9, and underlining shows amino acids found in MMP-1 and only in MMP-2 or MMP-9.

In one embodiment, it is desirable to inhibit MMPs-2 and 9, but to keep the level of MMP-1 relatively unregulated in order to inhibit tumor development or to heal chronic wounds. Based on the sequence alignment above one of skill in the art can design a peptide with amino acids that are found in MMP2 and MMP9 proenzyme sequences but not in the MMP1 proenzyme sequence, to produce a peptide that will inhibit MMP-2 and MMP-9, while leaving MMP-1 uninhibited. Such a peptide is provided by formula IV (SEQ ID NO:18).

$Xaa_a-Xaa_b-Xaa_c-Xaa_d-Xaa_e-Xaa_f-Xaa_g-Xaa_h-Xaa_i-$ (IV)

$Xaa_j-Xaa_k-Xaa_L-Xaa_m-Xaa_n-Xaa_o-Xaa_p-Xaa_1-Xaa_2-$ $Xaa_3-Xaa_4-Xaa_5-Xaa_6-Xaa_7-Xaa_8-Xaa_9-Xaa_{10}-$ $Xaa_{11}-Xaa_{12}-Xaa_{13}-Xaa_{14}-Xaa_{15}-Xaa_{16}-Xaa_{17}-$ $Xaa_{18}-Xaa_{19}$ wherein:

$Xaa_a$ is proline;
$Xaa_b$ is glutamine or glutamic acid;
$Xaa_c$ is threonine;
$Xaa_d$ is glycine;
$Xaa_e$ is aspartic acid or glutamic acid;
$Xaa_f$ is leucine;
$Xaa_g$ is aspartic acid;
$Xaa_h$ is glutamine or serine;
$Xaa_i$ is asparagine or alanine;
$Xaa_j$ is threonine;
$Xaa_k$ is isoleucine or leucine, desirably isoleucine;
$Xaa_L$ is glutamic acid or lysine, desirably glutamic acid;
$Xaa_m$ is threonine or alanine;
$Xaa_1$ is proline;
$Xaa_2$ is arginine;
$Xaa_3$ is cysteine;
$Xaa_4$ is glycine;
$Xaa_5$ is valine or asparagine, desirably asparagine;
$Xaa_6$ is proline;
$Xaa_7$ is aspartic acid;
$Xaa_8$ is valine or leucine, desirably leucine;
$Xaa_9$ is alanine or glycine, desirably glycine;
$Xaa_{10}$ is asparagine or arginine;
$Xaa_{11}$ is tyrosine or phenylalanine, desirably tyrosine;
$Xaa_{12}$ is asparagine or glutamine;
$Xaa_{13}$ is phenylalanine or threonine;
$Xaa_{14}$ is phenylalanine;
$Xaa_n$ is methionine;
$Xaa_o$ is arginine;
$Xaa_p$ is lysine or threonine;
$Xaa_{17}$ is lysine or aspartic acid;
$Xaa_{19}$ is lysine.
$Xaa_{15}$ is proline or glutamic acid, desirably proline;
$Xaa_{16}$ is arginine or glycine, desirably arginine;
$Xaa_{18}$ is proline or leucine, desirably leucine; and Peptide Modifications The invention also contemplates modifying the peptide inhibitors to stabilize them, to facilitate their uptake and absorption and to improve any other characteristic or property of the peptides that is known to one of skill in art. For example, the peptide inhibitors can be cyclized, charges on the peptide inhibitors can be neutralized, and the peptides can be linked to other chemical moieties.

Peptides can be cyclized by any method available to one of skill in the art. For example, the N-terminal and C-terminal ends can be condensed to form a peptide bond by known procedures. Functional groups present on the side chains of amino acids in the peptides can also be joined to cyclize the peptides of the invention. For example, functional groups that can form covalent bonds include —COOH and —OH; —COOH and —NH₂; and —COOH and —SH. Pairs of amino acids that can be used to cyclize a peptide include, Asp and Lys; Glu and Lys; Asp and Arg; Glu and Arg; Asp and Ser; Glu and Ser; Asp and Thr; Glu and Thr; Asp and Cys; and Glu and Cys. Other examples of amino acid residues that are capable of forming covalent linkages with one another include cysteine-like amino acids such Cys, hCys, β-methyl-Cys and Pen, which can form disulfide bridges with one another. Examples of cysteine-like amino acid residues include Cys and Pen. Other pairs of amino acids that can be used for cyclization of the peptide will be apparent to those skilled in the art.

The groups used to cyclize a peptide need not be amino acids. Examples of functional groups capable of forming a covalent linkage with the amino terminus of a peptide include carboxylic acids and esters. Examples of functional groups capable of forming a covalent linkage with the carboxyl terminus of a peptide include —OH, —SH, —NH₂ and —NHR where R is ($C_1$–$C_6$) alkyl, ($C_1$–$C_6$) alkenyl and ($C_1$–$C_6$) alkynyl.

The variety of reactions between two side chains with functional groups suitable for forming such interlinkages, as well as reaction conditions suitable for forming such interlinkages, will be apparent to those of skill in the art. Reaction conditions used to cyclize the peptides are generally sufficiently mild so as not to degrade or otherwise damage the peptide. Suitable groups for protecting the various functionalities as necessary are well known in the art (see, e.g., Greene & Wuts, 1991, 2nd ed., John Wiley & Sons, NY), as are various reaction schemes for preparing such protected molecules.

In one embodiment the charges at the N-terminal and C-terminal ends are effectively removed. This can be done by any method available to one of skill in the art, for example, by acetylating the N-terminus and amidating the C-terminus.

Methods for preparing cyclic peptides and modifying peptide in other ways are well-known in the art (see, e.g., Spatola, 1983, Vega Data 1(3) for a general review); Spatola, 1983, "Peptide Backbone Modifications" In: Chemistry and Biochemistry of Amino Acids Peptides and Proteins (Weinstein, ed.), Marcel Dekker, New York, p. 267 (general review); Morley, 1980, Trends Pharm. Sci. 1:463–468; Hudson et al., 1979, Int. J. Prot. Res. 14:177–185 (—CH$_2$NH—, —CH$_2$CH$_2$—); Spatola et al., 1986, Life Sci. 38:1243–1249 (—CH$_2$—S); Hann, 1982, J. Chem. Soc. Perkin Trans. I. 1:307–314 (—CH═CH—, cis and trans); Almquist et al., 1980, J. Med. Chem. 23:1392–1398 (—CO CH$_2$—); Jennings-White et al., Tetrahedron. Lett. 23:2533 (—CO CH$_2$—); European Patent Application EP 45665 (1982) CA:97:39405 (—CH(OH)CH$_2$—); Holladay et al., 1983, Tetrahedron Lett. 24:4401–4404 (—C(OH)CH$_2$—); and Hruby, 1982, Life Sci. 31:189–199 (—CH$_2$—S—).

Anti-Cancer Utility

According to the invention, the peptides provided herein are useful as anti-cancer agents. For example, the peptides of the invention can be used to diminish the growth of chondrosarcoma cells. Diseases involving inappropriate growth of chondrosarcoma cells include cancers, tumors, and the like. As used herein, the term "cancer or tumor" refers to any neoplastic disorder, including carcinomas, sarcomas and carcino-sarcomas. Cancers and tumors can be metastatic, non-metastatic, vascularized, non-vascularized, hard or soft. The compositions and methods of the invention can be used to treat or prevent conventional chondrosarcoma tumors, including those graded stage I through stage III, as well as other types of chondrosarcomas such as myxoid chondrosarcoma, mesenchymal chondrosarcoma, clear cell chondrosarcoma, dedifferentiated (spindle cell) chondrosarcomas, osteogenic sarcoma and the metastatic lesions secondary to these primary tumors. In general, any such neoplastic lesion may be treated according the present invention.

Peptides of the invention can therefore be used to inhibit tumor growth, development, metastasis and progression. Individual peptides, peptide variants, peptide derivatives and mixtures of peptides with different sequences can be combined in a formulation to prevent tumor growth, development, metastasis and/or progression. Optimal physiological functioning in conjunction with inhibiting tumor development may require some matrix metalloproteinase activity. Hence, the compositions and formulations of the present invention do not necessarily promote maximal inhibition of matrix metalloproteinases. Instead, the activity of the peptide inhibitor formulation is varied as needed to optimize physiological functioning while also inhibiting tumor growth and development. Lesser or greater levels of inhibition can be achieved by varying the type, content and amount of inhibitor peptides so that normal physiological functioning and tumor destruction are promoted.

To inhibit tumor development, promote tumor destruction, and support physiological processes, peptides of the invention are administered to a mammal in any manner chosen by one of skill in the art. For example, peptides can be formulated into a therapeutic composition containing a therapeutically effective amount of one or more peptides and a pharmaceutical carrier. Such a composition can be administered orally, parenterally or locally. Injectable solutions or suspensions of the present peptides can be made. Sustained release formulations can be utilized that can be administered orally or that can be implanted at the site of a cancer or tumor. Peptides can be administered in a drug delivery device that is implanted in a convenient location, for example, near a tumor or within an organ or bone that is believed to be cancerous or to be susceptible to cancer or tumor formation.

In another embodiment, peptides of the invention can be formulated into a therapeutic device or drug delivery device containing a therapeutically effective amount of one or more peptides impregnated into the device. The therapeutic or drug delivery device can permit release of the peptide inhibitor in an uncontrolled or a controlled manner. Hence, the therapeutic or drug delivery devices of the invention can provide slow or timed release of the peptide inhibitor into a tissue, for example, into bone tissue.

In one embodiment, a therapeutically effective amount of a peptide of the invention is an amount of peptide that inhibits a matrix metalloproteinase to a degree needed to inhibit sarcoma or tumor cell growth. In another embodiment, a therapeutically effective amount of a peptide of the invention is an amount of peptide that promotes healthy tissue development while inhibiting growth of chondrosarcoma cells.

For example, when present in a therapeutic or pharmaceutical composition, the amount of peptides of the invention can be in the range of about 0.001% to about 75% by weight of the composition. For example, the peptides can form about 0.5% to about 60% by weight of the composition. In an alternative example, the peptides form about 1.0% to about 50% by weight of the composition.

The therapeutically effective amount of peptide inhibitor necessarily varies with the route of administration. For example, a therapeutic amount between 30 to 112,000 μg per kg of body weight can be effective for intravenous administration. However, the amount of the peptide inhibitor required for tumor inhibition or destruction will vary not only with the route of administration, but also with the nature of the condition being treated and the age and condition of the patient, and will be ultimately at the discretion of the attendant physician or clinician.

The dosage and method of administration can vary depending upon the location of the tissue to be treated and/or upon the size of the tumor(s) or the severity of the cancer. Useful dosages of the peptides and peptide conjugates can be determined by correlating their in vitro activity, and in vivo activity in animal models described herein. The compound can conveniently be administered in unit dosage form; for example, containing about 0.001 μg to about 10 mg, conveniently about 0.01 μg to about 5 mg, more conveniently, about 0.10 μg to about 1 mg, and even more conveniently about 1.0 μg to 500 μg of peptide per unit dosage form. The desired dose may be presented in a single dose, as divided doses, or as a continuous infusion. The desired dose can also be administered at appropriate intervals, for example, as two, three, four or more sub-doses per day. One of skill in the art can readily prepare and administer an effective formulation from available information using the teachings provided herein.

The peptide inhibitors of the invention can be formulated as pharmaceutical compositions and administered to a mammalian host, such as a human patient in a variety of dosage forms adapted to the chosen route of administration, i.e., orally or parenterally, by intravenous, intramuscular, topical or subcutaneous routes.

Thus, the peptide inhibitors may be systemically administered, for example, intravenously or intraperitoneally by infusion or injection. Peptide inhibitors may also be locally administered, for example, by infusion or injection into a localized area, or by implantation of a drug delivery device into an affected area. Solutions of the peptide inhibitor can be prepared in water, and optionally mixed with a nontoxic surfactant. Dispersions can also be prepared in glycerol, liquid polyethylene glycols, triacetin, and mixtures thereof and in oils. Under ordinary conditions of storage and use, these preparations may contain a preservative to prevent the growth of microorganisms.

The pharmaceutical dosage forms suitable for injection or infusion or topical application can include sterile aqueous solutions or dispersions or sterile powders comprising the active ingredient that are adapted for the extemporaneous preparation of sterile injectable or infusible solutions or dispersions, optionally encapsulated in liposomes. In all cases, the ultimate dosage form must be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In some cases, one of skill in the art may choose to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the peptide or peptide conjugate in the required amount in the appropriate solvent with various of the other ingredients enumerated above, as required, followed by filter sterilization. In the case of sterile powders for the preparation of sterile injectable solutions, methods of preparation include, for example, vacuum drying and the freeze-drying techniques, which yield a powder of the active ingredient plus any additional desired ingredient present in the previously sterile-filtered solutions.

In some instances, the peptide inhibitors can also be administered orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the peptide inhibitor may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 75% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the peptide inhibitor may be incorporated into sustained-release preparations and devices.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use.

Thickeners such as synthetic polymers, fatty acids, fatty acid salts and esters, fatty alcohols, modified celluloses or modified mineral materials can also be employed with liquid carriers to form spreadable pastes, gels, ointments, and the like, for application directly to a cancer site within the user.

The active peptides may be administered topically by any means either directly or indirectly to the selected tissue as sprays, foams, powders, creams, jellies, pastes, suppositories or solutions. The term paste used in this document should be taken to include creams and other viscous spreadable compositions such as are often applied directly to the skin or spread onto a prosthetic device, bandage or dressing. Peptides of the invention can be covalently attached, stably adsorbed or otherwise applied to a skin covering, prosthetic device or wound dressing material. To facilitate healing after surgery, the active peptides can be applied directly to target tissues or to implantable prosthetic devices. The compositions can be administered by aerosol, as foam or as a mist along with other agents directly onto the surgical site, skin or wound.

The peptides can be administered in a formulation that can include an emulsion of the peptide in a wax, oil, an emulsifier, water, and/or a substantially water-insoluble material that forms a gel in the presence of water. The formulation provides the desirable properties of an emulsion, in that it is spreadable and has the creamy consistency of an emulsion, yet that does not break down when subjected to normal sterilization procedures, e.g. steam sterilization, because the gel stabilizes the emulsion. It also exhibits better water retention properties than a conventional gel because water is held both in the emulsion and in the gel.

The formulation can also contain a humectant to reduce the partial vapor pressure of the water in the cream or lotion to reduce the rate at which the cream or lotion dries out. Suitable humectants are miscible with water to a large extent and are generally suitable for application to the skin. Polyols are suitable for the purpose. Examples of suitable polyols may include monopropylene glycol or glycerin (glycerol). The polyol may be present in proportions of about 20–50% (by weight) of the total formulation; alternatively the range may be, for example, about 30–40%. This relatively high proportion of polyol also ensures that if the paste should dry out to any degree, the resulting paste remains soft and flexible because the glycerin may act as a plasticizer for the polymer. When the paste is applied on a bandage, for example, it may therefore still be removed easily from the skin when the paste has lost water without the need to cut the bandage off. The polyol also has the advantage of functioning to prevent the proliferation of bacteria in the paste when it is in contact with the skin or wound, particularly with infected wounds.

The formulation can include other ingredients. Ingredients that may be used include: zinc oxide, ichthammol, calamine, silver suphadiazine, chlorhexidine acetate, coal tar, chlorhexidine gluconate, salicylic acid, metronidazole or other antibacterial agents, or a combination thereof. Other ingredients may also be found suitable for incorporation into the cream.

One example of a wax for emulsion of the present peptides is glyceryl monostearate, or a combination of glyceryl monostearate and PEG 100 stearate that is available commercially as CITHROL GMS/AS/NA from Croda Universal Ltd. This combination provides both a wax and an emulsifier (PEG 100 stearate) that is especially compatible with the wax, for forming an emulsion in water. A second emulsifier can be included in the formulation to increase the stability of the emulsion, for example, a PEG20 stearate, such as CITHROL 1OMS that is supplied by Croda Universal Ltd. The total concentration of emulsifier in the cream should normally be in the range of from 3–15%. Where two emulsifiers are used, one may be present in a greater concentration than the other.

The water-insoluble material forms a gel with the water of the formulation. The material is therefore hydrophilic but does not dissolve in water to any great extent. The material can be a polymeric material that is a water-absorbing non water-soluble polymer. However, non-polymeric materials that form gels with water and that are stable at elevated temperatures could also be used, e.g. clays such as kaolin or bentonite. Some polymers used in the invention are superabsorbent polymers such as those disclosed in WO-92/16245 and that comprise hydrophilic cellulose derivatives that have been partially cross-linked to form a three dimensional structure. Suitable cross-linked cellulose derivatives include those of the hydroxy lower alkyl celluloses, wherein the alkyl group contains from 1 to 6 carbon atoms, e.g. hydroxyethyl cellulose or hydroxypropylcellulose, or the carboxy-celluloses e.g. carboxymethyl hydroxyethyl cellulose or carboxymethylcellulose. An example of a polymer that is partially cross-linked is sodium carboxymethylcellulose, supplied as AKUCELL X181by Akzo Chemicals B.V. This polymer is a superabsorbent polymer in that it may absorb at least ten times its own weight of water. The cross-linked structure of the polymer prevents it from dissolving in water but water is easily absorbed into and held within the three-dimensional structure of the polymer to form a gel. Water is lost less rapidly from such a gel than from a solution and this is advantageous in slowing or preventing the drying out of the cream formulation. The polymer content of the formulation is normally less than 10%, for example, in the range of about 0.5 to about 5.0% by weight, or about 1.0% to about 2%.

The formulation may be sterilized and components of the formulation should be selected, by varying the polymer content, to provide the desired flow properties of the finished product. That is, if the product is to be sterilized, then the formulation should be chosen to give a product of relatively high viscosity/elasticity before sterilization. If certain components of the formulation are not to be sterilized, the formulation can be sterilized before addition of those components, or each component can be sterilized separately. The formulation can then be made by using sterile conditions to mix each sterilized ingredient into the formulation. When components are separately sterilized and then mixed together, the polymer content can be adjusted to give a product having the desired flow properties of the finished product. The emulsion content determines the handling properties and feel of the formulation, higher emulsion content leading to increased spreadability and creaminess.

The formulation may be packaged into tubes, tubs or other suitable forms of container for storage or it may be spread onto a substrate and then subsequently packaged. Suitable substrates include dressings, such as implantable devices, film dressings, and bandages.

The invention is further described by the following examples, which are illustrative of specific modes of practicing the invention and are not intended as limiting the scope of the invention as defined by the appended claims.

EXAMPLE 1

Peptide Inhibitors of Matrix Metalloproteinases

General Materials

All peptides were synthesized by Sigma-Genosys, Inc. The released peptides were purified to >95% homogeneity via RP-HPLC by the company. The pooled eluted peak material was desalted and lyophilized. Mass Spectroscopy analysis confirmed the peptide molecular weight and purity. Unless otherwise noted, all chemicals were purchased from Sigma Chemical Corp. or from Fluka Chemical Co. Active MMP-9 enzyme was purchased from Calbiochem.

Molecular Modeling

Molecular modeling utilized two visualization programs, Swiss PDB Viewer (Guex and Peitsch, 1997) and Rasmol (Sayle and Milner-White, 1995). Model work was performed on a Compaq PC running Windows 95, as well as a Silicon Graphics, Inc. Octane UNIX workstation. Additionally, the Cerius2 molecular package from Molecular Simulations, Inc. was utilized on the Octane. Three dimensional structure files were downloaded from the Protein Databank as follows (filename, reference): MMP-1 (1FBL, Li et al., 1995), MMP-2 (1GEN, Libson et al., 1995), MMP-8 (1JAO, 1JAN, Grams, et al., 1995; Reinemer et al., 1994), MMP-9 (1MMQ, Browner et al., 1995), TIMP-2/MT-1 MMP complex (1BUV, Fernandez-Catalan et al., 1998), TIMP-2 (1BR9, Tuuttila et al., 1998), and TIMP-1/MMP complex (1UEA, Gomis-Ruth et al., 1997; Huang et al., 1996; Becker et al., 1995). These files were used to analyze the three-dimensional structure of the proteins, as well as being the source of primary sequence data.

Inhibition Assays

Two enzymatic assays were performed. The first assay measured the enzymatic hydrolysis of fluoresceinated collagen by MMP-9 as a function of time. Fluoresceinated collagen (Molecular Probes, Inc.), at a concentration of 5 μM was added to reaction buffer (50 mM Tris-HCl (pH 7.6), 150 mM NaCl, 5 mM $CaCl_2$, 0.1 mM $NaN_3$) and was placed into a Spectrosil™ quartz fluorimeter cuvette. MMP, at a concentration of 0.1 μM, was mixed with varying amounts of peptide and incubated at 25° C. for 10 minutes in order to affect binding. The protein mixture was added to the collagen substrate, and was quickly mixed. Fluorescence emission intensity at 520 nm was measured as a function of time (excitation wavelength 495 nm) in a Shimadzu RF5301 fluorimeter (Lakowicz, 1983). The fluorescein release assay was used to determine the inhibitory constant (Ki) of the peptide inhibitor ([I]) according to Segel (1993) via the use of Dixon plots (1/v vs. [I]), such that:

$$\text{slope} = Km/(V\text{max } Ki\ [S]) \tag{1}$$

where Km is the Michaelis constant, Vmax is the reaction maximum velocity, and [S] is the substrate concentration.

The second assay utilized the technique of fluorescence resonance energy transfer (FRET). The substrate peptide (Calbiochem) of seven amino acids was coupled to a carboxyl terminal dinitrophenyl acceptor, and an amino terminal 2-aminobenzo-anthraniloyl (Abz) moiety donor. Cleavage of this substrate by MMP-9 resulted in the liberation of a fluorescent product (365 nm excitation, 450 nm emission). Peptide at a concentration of 5 μM was added to reaction buffer (50 mM Tris-HCl (pH 7.6), 150 mM NaCl, 5 mM CaCl$_2$, 0.1 mM NaN$_3$) and the mixture was placed into a black 96-well microtiter plate well that had been previously blocked with 1% BSA. MMP at a concentration of 0.1 μM was mixed with varying amounts of either the 9-mer (SEQ ID NO:12), the 10-mer (SEQ ID NO:13), or the 19-mer (SEQ ID NO:11) peptide and incubated at 25° C. for 10 minutes in order to effect binding. The protein mixture was added to the fluorescent peptide substrate, and was quickly mixed. Fluorescence intensity as a function of time was measured with a Dynex MFX fluorescence microtiter plate reader. Fluorescence intensity was related back to moles of peptide cleaved by producing a standard curve with an Abz containing non-FRET peptide. Inhibitory constants were derived from the curves as above. Other matrix metalloproteinase enzymes were tested in a similar manner utilizing specific substrate FRET peptides (all from Calbiochem).

Anti-activation Assay

The assay measured how much proenzyme was converted into mature matrix metalloproteinase. Proenzyme pro-MMP-9 (100 μg) was mixed with 0.5 μg of stromilysin in PBS. The reaction was incubated at 35° C. Aliquots were removed from the reaction over an 80 minute time course. Each aliquot was mixed with EDTA to a final concentration of 1 mM, injected onto a BioSelect 125 HPLC column and chromatographed in PBS. The zero (injection) time point was a single peak that elutes from the column in approximately 750 seconds. This peak reduced in size as a function of time, and two new peaks appeared. The first peak eluted at approximately 800 seconds, and represented the mature form of MMP-9. The second peak eluted at approximately 1100 seconds, and corresponded to the N-terminal prodomain fragment. Peak areas were determined by integrating over the elution profile, and the percent area changes were plotted.

Isothermal Titration Calorimetry

Isothermal titration calorimetry (ITC) was performed with a VP-ITC instrument from MicroCal, Inc. Titrations were carried out by injecting 5 μL of an inhibitor peptide solution (at concentration ranges from 0.5 mM to 2.0 mM) into the 1.4 mL stirred reaction cell. MMP-9 ranged in concentration from 50 to 80 μM in the cell. Both the inhibitor and the enzyme were in 20 mM sodium cacodylate (pH 5.5–7.0), 40 mM NaCl, or 20 mM Tris-HCl (pH 7.0–7.5), 40 mM NaCl. Titrations were conducted between 20° C. and 40° C. Typical experimental conditions for the titrations were a 10 second injection period followed by a 240 second delay between injections for a total of 40 injections. Blank titrations of inhibitor peptide into buffer were performed in order to correct for heats of dilution and mixing.

The independent set of multiple binding sites is the most common model for binding experiment evaluations. The analytical solution for the total heat was determined by (Freire et al., 1990):

$$Q = V \Delta H \times \left[ [L] + \frac{1 + [M]nK - \sqrt{(1 + [M]nK - [L]K)^2 + 4K[L]}}{2K} \right] \quad (2)$$

where Q is the total heat, V is the cell volume, ΔH is the enthalpy, M is the macromolecule concentration (the binding partner in the cell), n is the binding stoichiometry, L is the ligand concentration (the binding partner in the syringe), and K is the association constant. Data were fit to this model using Origin version 5 (MicroCal, Inc.).

Surface Plasmon Resonance

The BiaCore-X surface plasmon resonance (SPR) device (BiaCore, Inc.) was utilized to measure the interaction between the 19-mer (SEQ ID NO:11) peptide (P) and MMP-9. For these experiments a carboxymethyl dextran sensor chip (CM-5, Lofas et al., 1993) was activated with 50 mM N-hydroxysuccinimide, 0.2 M N-ethyl-N'-(dimethylaminopropyl)-carbodiimide at a flow rate of 10 μL per minute for ten minutes. MMP-9 at a concentration of 75 ng/μL was coupled to the activated surface at a flow rate of 10 μL per minute for ten minutes. The final surface was inactivated by flowing 1 M ethanolamine-HCl at a rate of 10 μL per minute for five minutes over the sensor surface. The 19-mer (SEQ ID NO:11) peptide was flowed over the sensor surface at a rate of 20 μL per minute, and at concentrations that ranged from 10 to 50 nM. The association and dissociation phases of the binding isotherms were smoothed by an automated FFT routine prior to modeling rate constants. Binding isotherms were evaluated by simultaneously fitting the forward ($k_a$) and reverse ($k_d$) rate constants to:

$$d[P\sim MMP\text{-}9]/dt = (k_a[P][MMP\text{-}9]) - (k_d[P\sim MMP\text{-}9]) \quad (3)$$

(Karlsson and Falt, 1997) where [P], [MMP-9], and [P~MMP-9] are the concentrations of free peptide, free MMP-9, and the complex respectively. The equilibrium affinity constant ($K_A$) is then defined as:

$$K_A = k_a/k_d \quad (4)$$

Equation 3 is properly expressed in terms of the SPR signal (Morton et al., 1995) as:

$$dR/dt = k_a C R_{max} - (k_a C + k_d) R \quad (5)$$

where R is the SPR signal (in response units, RU) at time t, $R_{max}$ is the maximum MMP-9 binding capacity in RU, and C is the chelating peptide concentration. Kinetic analysis (O'Shannessy et al., 1993) was performed using Origin from Microcal, Inc.

Viability Assays

The relative toxicity of the 9-mer (SEQ ID NO:12), the 10-mer (SEQ ID NO:13) and the 19-mer (SEQ ID NO:11) peptides was assayed using the skin model Epiderm™ from MatTek Corp. The individual skin sample containers were preincubated in culture medium at 37° C., 5% CO$_2$ for two hours prior to the addition of the peptides. The sample containers were transferred to 6 well plates that contained fresh media. All peptides were dissolved in PBS at a final concentration of 10 mM, and 100 μL each peptide solution was pipetted onto the surface of the Epiderm sample container. Incubation was continued for 12 hours at 37° C., 5% CO$_2$. After the incubation period, the sample containers were washed three times with PBS and the sample containers were transferred to a 24 well plate that contained 300 μL of MTT assay media per well (MTT concentration was 1 mg/mL). The colorimetric assay was allowed to develop for three hours (incubation at 37° C., 5% $CO_2$). Sample containers were then transferred to a 24 well culture plate that contained 2 mL of isopropanol per well. Extraction of the colored precipitate occurred over a period of four hours at room temperature. Absorbance readings were taken at 570 nm and 650 nm for each sample. The percent viability of each sample relative to a PBS control was calculated as:

$$100 \times (OD_{570}^{sam-OD_{650}^{sam}})/(OD_{570}^{con-OD_{650}^{con}}) \quad (6)$$

Routinely, the peptide sample was assayed in triplicate.

Results

The sequence of matrix metalloproteinase-2 (SEQ ID NO:14) is provided below to facilitate definition of the various domains and regions in matrix metalloproteinases.

```
  1 MEALMARGAL TGPLRALCLL GCLLSHAAAA PSPIIKFPGD
 41 VAPKTDKELA VQYLNTFYGC PKESCNLFVL KDTLKKMQKF
 81 FGLPQTGDLD QNTIETMRKP RCGNPDVANY NFFPRKPKWD
121 KNQITYRIIG YTPDLDPETV DDAFARAFQV WSDVTPLRFS
161 RIHDGEADIM INFGRWEHGD GYPFDGKDGL LAHAFAPGTG
201 VGGDSHFDDD ELWTLGEGQV VRVKYGNADG EYCKFPFLFN
241 GKEYNSCTDT GRSDGFLWCS TTYNFEKDGK YGFCPHEALF
281 TMGGNAEGQP CKFPFRFQGT SYDSCTTEGR TDGYRWCGTT
321 EDYDRDKKYG FCPETAMSTV GGNSEGAPCV FPFTFLGNKY
361 ESCTSAGRSD GKMWCATTAN YDDDRKWGFC PDQGYSLFLV
401 AAHEFGHAMG LEHSQDPGAL MAPIYTYTKN FRLSQDDIKG
441 IQELYGASPD IDLGTGPTPT LGPVTPEICK QDIVFDGIAQ
481 IRGEIFFFKD RFIWRTVTPR DKPMGPLLVA TFWPELPEKI
521 DAVYEAPQEE KAVFFAGNEY WIYSASTLER GYPKPLTSLG
541 LPPDVQRVDA AFNWSKNKKT YIFAGDKFWR YNEVKKKMDP
601 GFPKLIADAW NAIPDNLDAV VDLQGGGHSY FFKGAYYLKL
641 ENQSLKSVKF GSIKSDWLGC
```

A robust pairwise alignment of the cleavage region of nine MMP amino acid sequences was calculated using the program CLUSTAL™ (Higgins et al., 1992). This alignment defined the positions of both conserved and nonconserved amino acids that flanked the activation proteinase cleavage site. An arbitrary number of N-terminal amino acids, as well as the number of amino acids C-terminal to the activation cleavage site were picked for the alignment. The alignment of MMP sequences (Table 1) shown in FIG. 1 indicated that all of the MMP activation regions can be aligned in a statistically significant manner. The regions chosen for the alignment roughly corresponded to amino acids 70–120, assuming an average MMP structure of signal sequence was amino acids 1–20, the propeptide domain was amino acids 21–100, and the mature active enzyme was from amino acids 101 to the end. The 19-mer (SEQ ID NO:11) sequence that was chosen for study is contained within the alignment region. Specifically, in MMP-2 the 19-mer (SEQ ID NO:11) corresponds to amino acids 100–118.

Alignment of the MMP sequences indicated that the central region of the activation domain, PRCGVPDV (SEQ ID NO:1), is highly conserved and that there is a larger degree of sequence variation flanking this area. The sequence heterogeneity can be used to design peptide sequences that inhibit specific MMP enzymes, or combinations of MMPs, simply by choice of matrix metalloproteinase-specific amino acids (based on this alignment). In addition the length of a particular peptide can be varied in order to modulate potency.

The three dimensional structure of proMMP-1 is provided in FIG. 2, indicating that the activation regions shown in Table 1 and FIG. 1 each constitute a bridge that interconnects two large globular domains. The cleavage region is defined as a short unstructured domain that connects the propeptide domain to the active enzyme domain. This sequence is cleaved in two as part of the activation step. It is also the region that is sensitive to $HgCl_2$ mediated activation in vitro.

Figure 3:
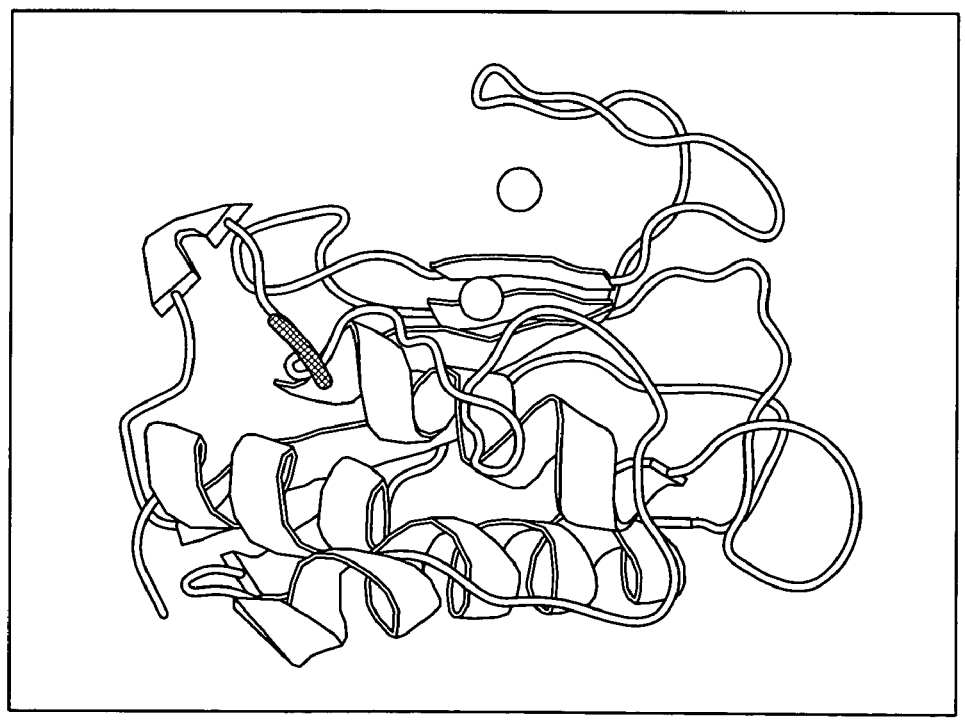
FIG. 3 provides a three-dimensional model of MMP-9. The cleavage region that creates the N-terminus of the active proteinase is shown in cross-hatching. The two zinc ions are illustrated as spheres. The cleavage domain peptide may bind to the MMP in the vicinity of its normal location in the proenzyme. This binding (also near the catalytic zinc) sterically blocks a portion of the active site. This blockage prevents substrate binding.

Activation removes the steric block (that was the propeptide domain) uncovering the mature enzyme active site. The N-terminal end is in proximity to the catalytic zinc ion, which is absolutely required for enzymatic activity. The structure of active MMP-9 is shown in FIG. 3, with the zinc ions depicted as solid balls. The second zinc is a structural ion, that is, it contributes to protein stability, but not to catalysis. The C-terminal half of the 19-mer (SEQ ID NO:11) peptide is now the enzyme's extreme amino terminus, shown to the left of FIG. 3 as an ascending portion of the last loop (in crosshatching). Modeling of the activation domain peptide to the surface of the activated MMPs indicates that the peptide (especially if longer N-terminal regions are included) can interact with the active site region, in effect, blocking substrate access to the active site. In that manner it may act as a mini pro-domain or enzymatic "cap."

It is known that enzymes can be proteolyzed into fragments and these fragments can be reconstituted to regenerate active enzyme. The various peptide domains reassemble and are held together by noncovalent intermolecular forces. A classic example of such a peptide-protein interaction involves the ribonuclease S-peptide/ribonuclease S-protein interaction (Levit and Berger, 1976). The ribonuclease S-peptide binds to the S-protein in its proper position and the resulting complex restores the enzymatic activity of RNAse-S.

According to the invention, the activation domain peptides may rebind to the activated MMP in the area where they occur in the proMMP forming an inactive complex. Such binding can be measured (see below). Moreover, the 19-mer (SEQ ID NO:11) peptide may ligand the zinc through its cysteine residue, again preventing catalysis.

Inhibition of MMP Enzymatic Activity

The first inhibition studies were performed with a 19 amino acid peptide (SEQ ID NO:11) that was derived from the MMP-2 cleavage domain region. This peptide was selected from the area of the CLUSTAL alignment that demonstrated the highest degree of conservation. The selected 19-mer (SEQ ID NO:11) is strictly conserved at the N-terminus, but shows a high degree of variability in the C-terminus. Two smaller peptides that represent the N-terminal and C-terminal halves of this peptide were also tested. The two halves roughly divide the peptide into the conserved N-terminal portion (9-mer (SEQ ID NO:12)) and the non conserved C-terminal portion (10-mer (SEQ ID NO:13)). This allows for testing not only for the overall efficacy of inhibition, but also for sequence selectivity.

```
19-mer:    PRCGNPDVANYNFFPRKPK (SEQ ID NO:11)
9-mer:     PRCGNPDVA           (SEQ ID NO:12)
10-mer:             NYNFFPRKPK (SEQ ID NO:13)
```

Figure 4:
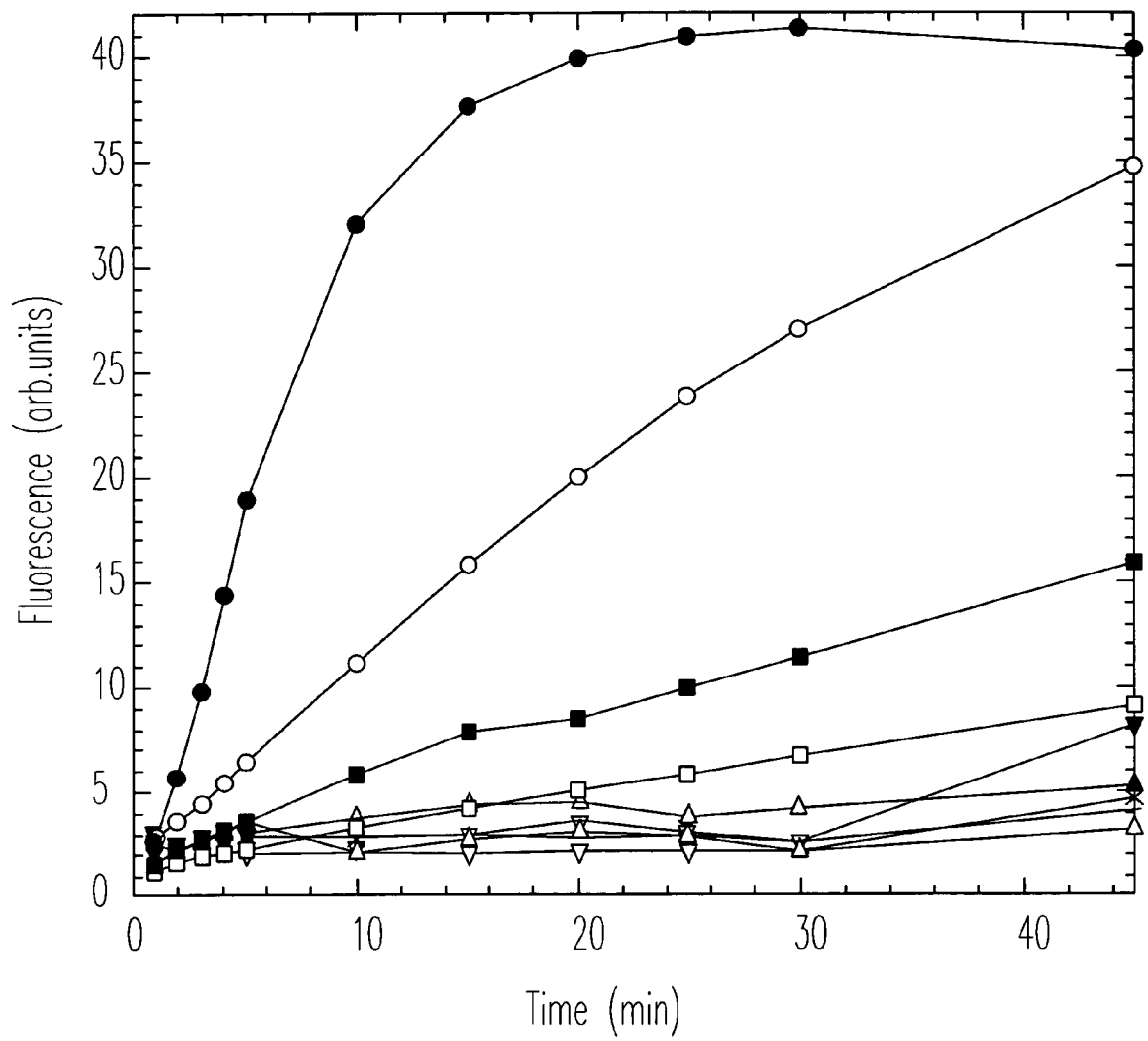
FIG. 4 illustrates the inhibition of MMP-9 activity by the 19-mer (SEQ ID NO:11) cleavage domain peptide. MMP-9 was mixed with the 19-mer (SEQ ID NO:11) peptide prior to the FRET assay. The concentrations of the 19-mer (SEQ ID NO:11) peptide were as follows: 0 mM (closed circles), 0.01 mM (open circles), 0.03 mM (closed squares), 0.06 mM (open squares), 0.125 mM (closed triangles), 0.25 mM (open triangles), 0.5 mM (x's), 1 mM (inverted closed triangles), 2 mM (inverted open triangles).

All three peptides were capable of inhibiting MMP-9 in either fluorescence based assay. In all cases studied, the 19-mer (SEQ ID NO:11) was a better enzymatic inhibitor than were the two half peptides. The 9-mer (SEQ ID NO:12) was a more effective inhibitor than the C-terminal 10-mer (SEQ ID NO:13) peptide. These results indicate that the cysteine may be needed because it acts as a zinc ligand or that N-terminal regions are required to effect the steric blocking of the enzyme active site. This hypothesis may be tested by producing inhibitor peptides that contain more N-terminal sequence (meaning amino acids before residue 100). A typical inhibition plot of MMP-9 titrated with the 19-mer (SEQ ID NO:11) is shown in FIG. 4.

Figure 5:
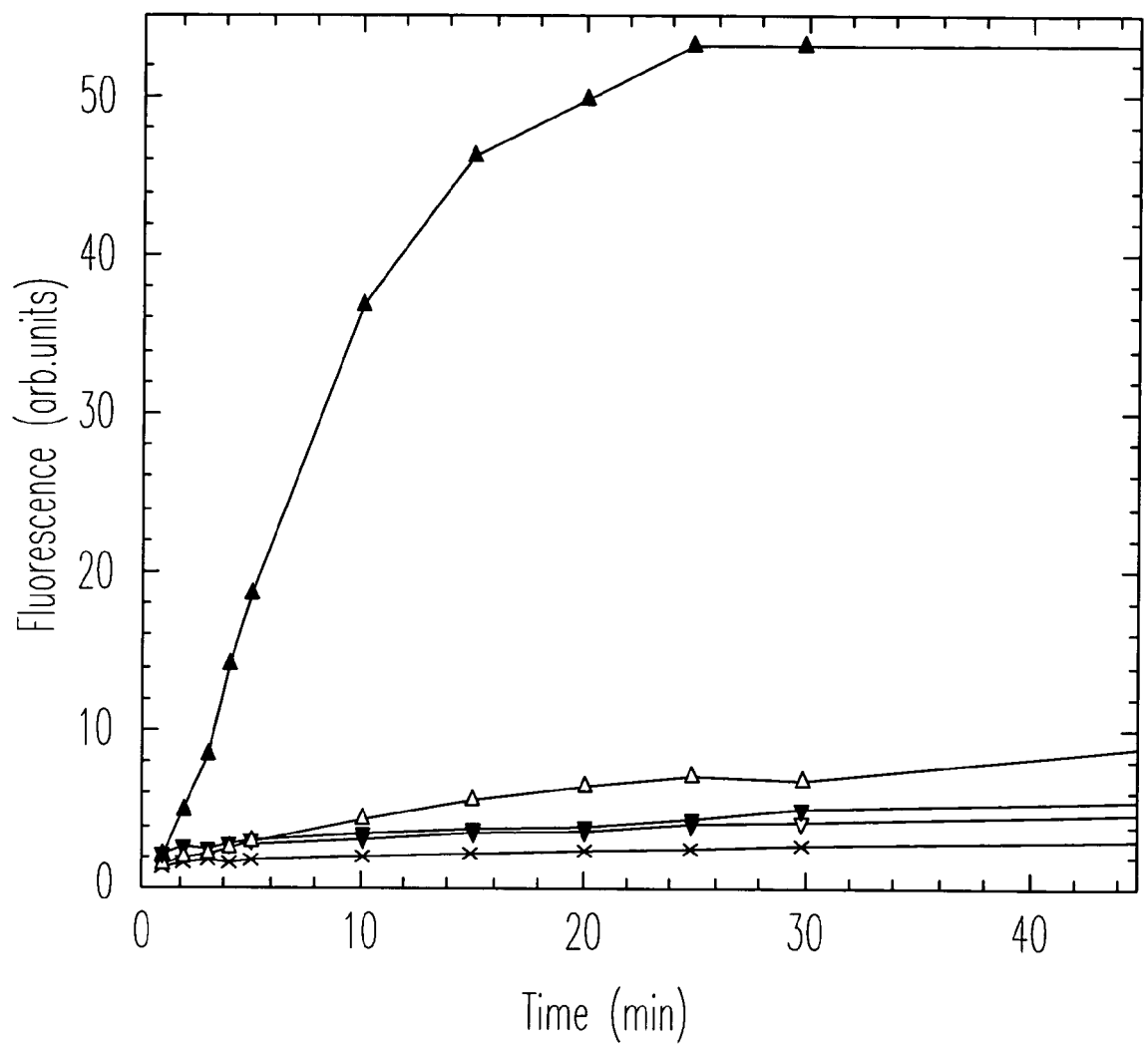
FIG. 5 illustrates the inhibition of MMP-9 activity by the 10-mer (SEQ ID NO:13) cleavage domain peptide. MMP-9 was mixed with the 10-mer (SEQ ID NO:13) peptide prior to the FRET assay. The concentrations of the 10-mer (SEQ ID NO:13) peptide were as follows: 0 mM (closed triangles), 0.25 mM (open triangles), 0.5 mM (open inverted triangles), 1.0 mM (closed inverted triangles), 2.0 mM (x's).
Figure 6:
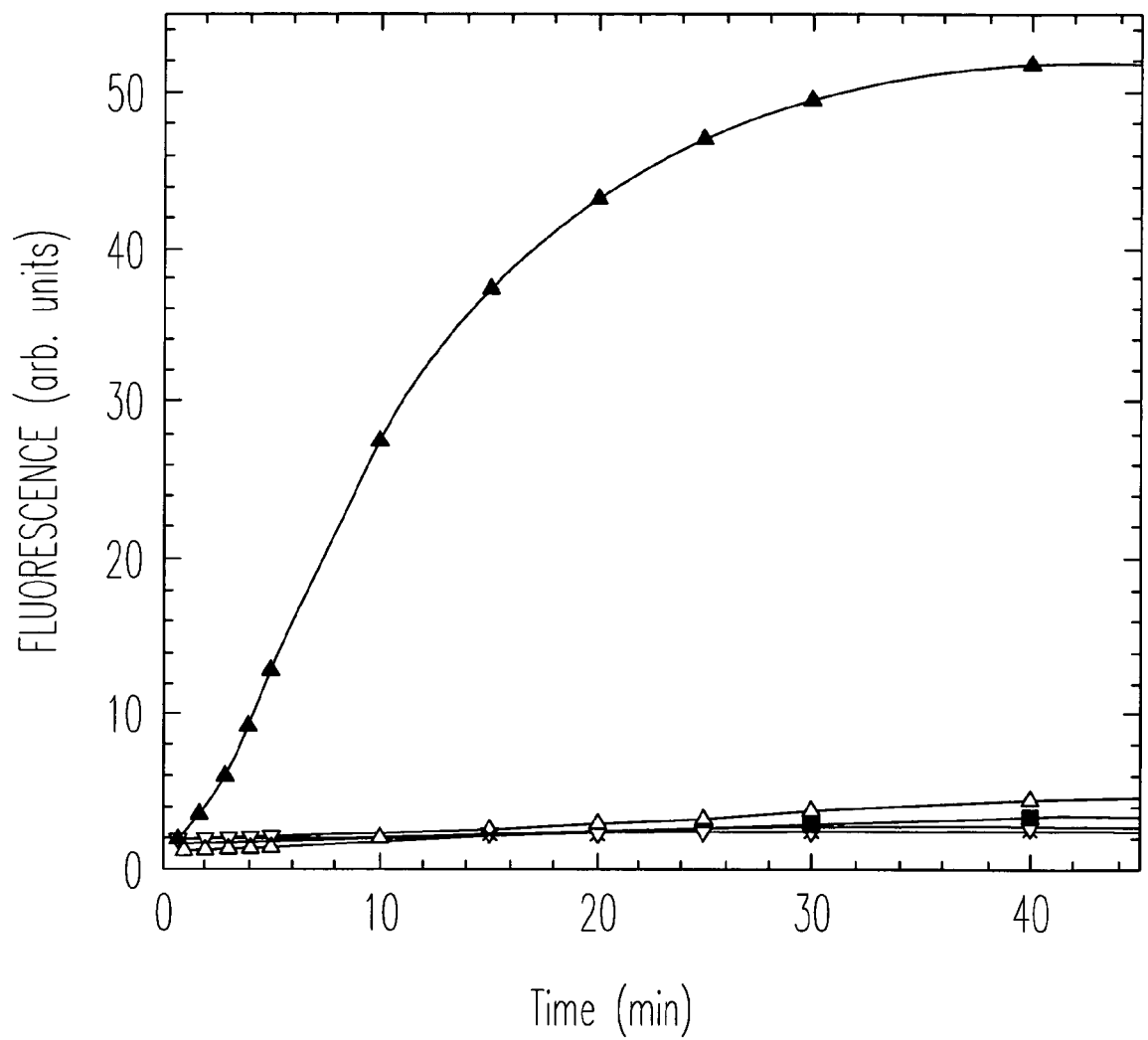
FIG. 6 illustrates the inhibition of MMP-9 activity by the 9-mer (SEQ ID NO:12) cleavage domain peptide. MMP-9 was mixed with the 9-mer (SEQ ID NO:12) peptide prior to the FRET assay. The concentrations of the 9-mer (SEQ ID NO:12) peptide were as follows: 0 mM (closed triangles), 0.25 mM (open triangles), 0.5 mM (open inverted triangles), 1.0 mM (closed inverted triangles), 2.0 mM (x's).
Figure 7:
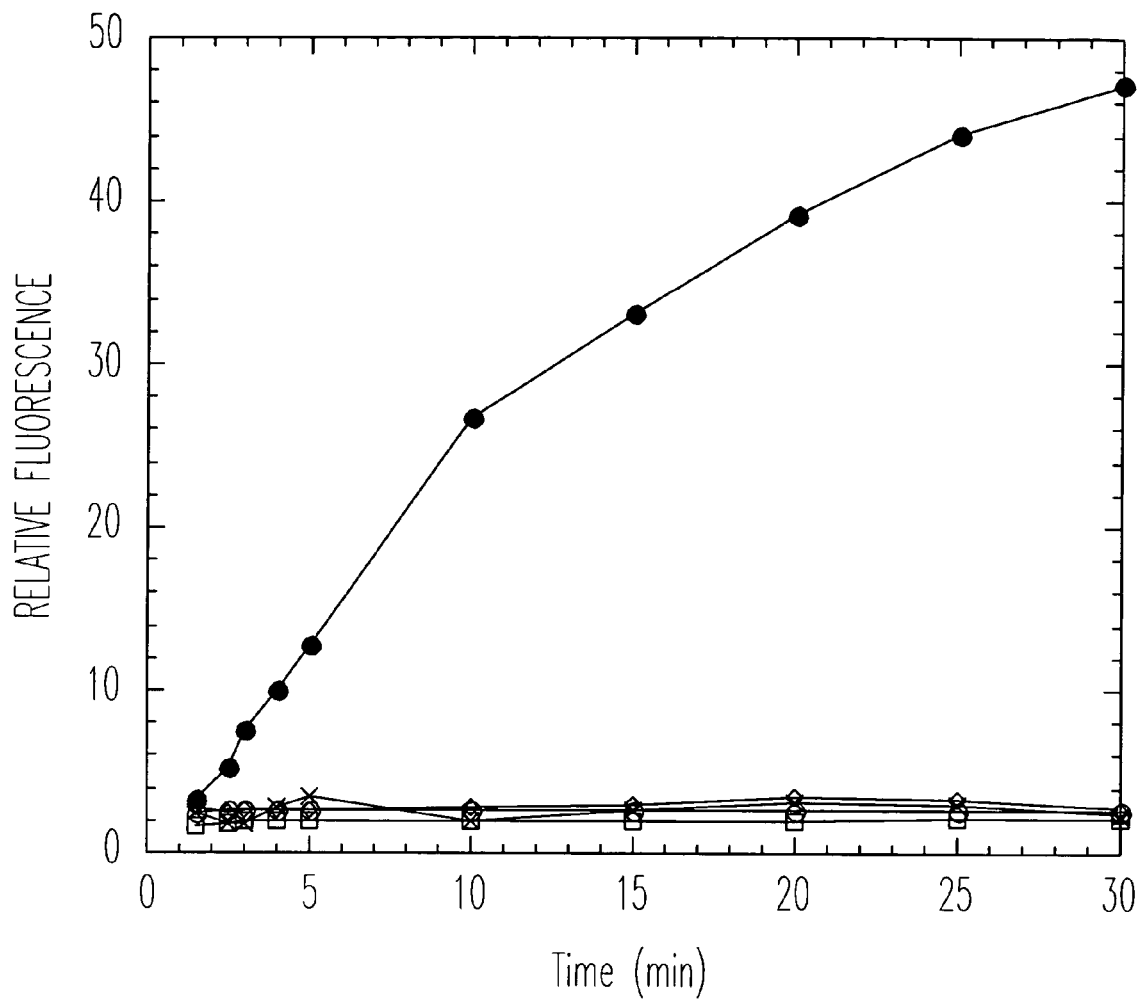
FIG. 7 illustrates the inhibition of MMP-9 activity by the 19-mer (SEQ ID NO:11) cleavage domain peptide. MMP-9 was mixed with the 19-mer (SEQ ID NO:11) peptide prior to the fluorescent collagen assay. The concentrations of the 19-mer (SEQ ID NO:11) peptide were as follows: 0 mM (closed circles), 0.06 mM (open diamonds), 0.1 mM (open squares), 0.25 mM (open circles), 0.5 mM (x's).
Figure 8:
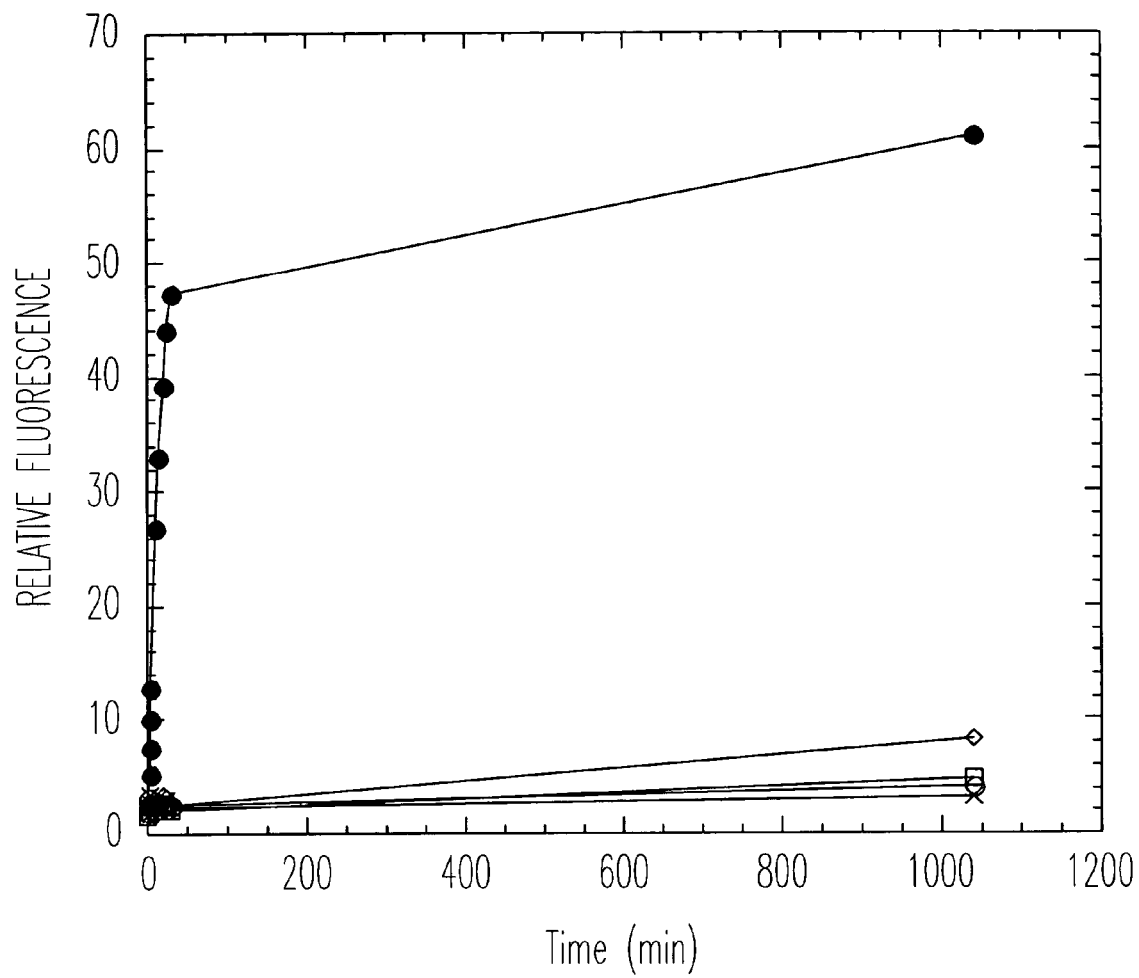
FIG. 8 illustrates a longer time course inhibition of MMP-9 activity by the 19-mer (SEQ ID NO:11) cleavage domain peptide. MMP-9 was mixed with the 19-mer (SEQ ID NO:11) peptide prior to the fluorescent collagen assay. The concentrations of the 19-mer (SEQ ID NO:11) peptide were as follows: 0 mM (closed circles), 0.06 mM (open diamonds), 0.1 mM (open squares), 0.25 mM (open circles), 0.5 mM (x's).
Figure 9:
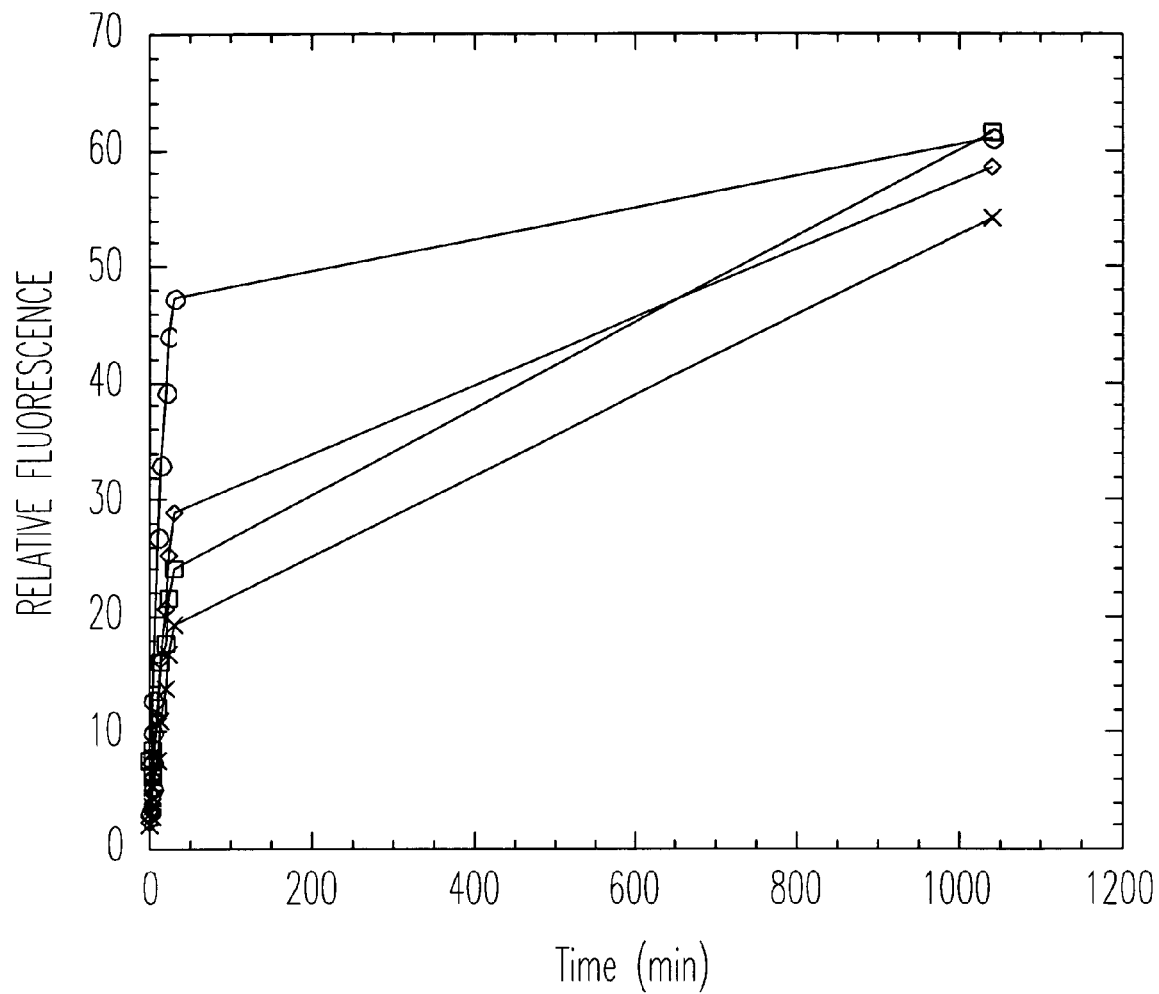
FIG. 9 illustrates a longer time course inhibition of MMP-9 activity by the 10-mer (SEQ ID NO:13) cleavage domain peptide. MMP-9 was mixed with the 10-mer (SEQ ID NO:13) peptide prior to the fluorescent collagen assay. The concentrations of the 10-mer (SEQ ID NO:13) peptide were as follows: 0 mM (open circles), 0.1 mM (open diamonds), 0.2 mM (open squares), 0.4 mM (x's).

Similar inhibition analyses performed with the 10-mer (SEQ ID NO:13) and the 9-mer (SEQ ID NO:12) peptides are shown in FIGS. 5 and 6 respectively. Each peptide was capable of inhibiting MMP-9 in the FRET-based assay, with inhibitor constants (Ki's) ranging from 45.2 to 327.7 µM (see Table 4). The choice of substrate (FRET peptide or fluoresceinated collagen) made little difference in the relative inhibition of the three peptides, with a consistent trend as follows: 19-mer (SEQ ID NO:11)>9-mer (SEQ ID NO:12)>10-mer (SEQ ID NO:13). Typical reaction plots for titrating MMP-9 with the peptides are shown in FIGS. 7–9.

Inhibitor constants were slightly lower overall for the collagen substrate, ranging from 30.3 to 221.3 µM for collagen and 45.2 to 327.7 µM for the FRET-peptide. These data indicate that the peptides are somewhat more effective inhibitors when a collagen substrate is utilized, suggesting that the inhibitor peptide blocks the active site and that, because collagen is significantly larger than the FRET-peptide substrate, it is easier to prevent its access to the enzyme active site. The smaller FRET-peptide substrate may more readily gain access the active site, even in the presence of an inhibitor peptide.

Figure 10:
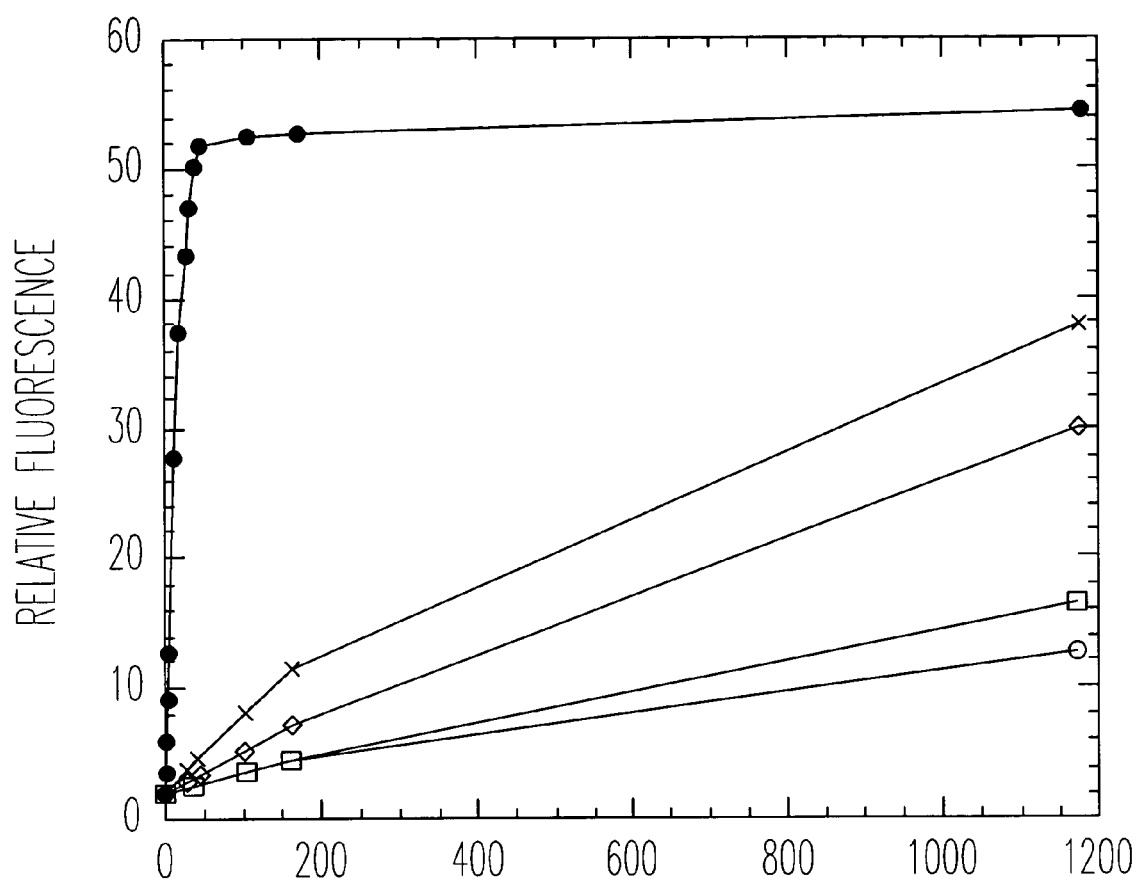
FIG. 10 illustrates a longer time course of inhibition of MMP-9 activity by the 9-mer (SEQ ID NO:12) cleavage domain peptide. MMP-9 was mixed with the 9-mer (SEQ ID NO:12) peptide prior to the fluorescent collagen assay. The concentrations of the 9-mer (SEQ ID NO:12) peptide were as follows: 0 mM (closed circles), 0.06 mM (open diamonds), 0.1 mM (open squares), 0.25 mM (open circles), 0.5 mM (x's).

Typically, enzymatic assays (e.g., as shown in FIGS. 4–7) were conducted for 30–40 minutes. However, extended time assays showed that the 19-mer (SEQ ID NO:11) effectively inhibited the MMP-9 catalyzed hydrolysis of collagen for periods of time beyond 1000 minutes (FIG. 8). The 10-mer (SEQ ID NO:13) peptide was less effective at preventing the destruction of collagen at long time points (FIG. 9) than is the 9-mer (SEQ ID NO:12) peptide (FIG. 10). Again the 19-mer (SEQ ID NO:11) peptide showed the greatest degree of inhibition.

Similar enzymatic studies were performed on other MMP enzymes to test the effectiveness of the 19-mer (SEQ ID NO:11) peptide. These assays utilized FRET peptides that incorporated specific MMP cleavage sites into their sequences. The 19-mer (SEQ ID NO:11) peptide was capable of potently inhibiting multiple MMPs. The effectiveness of the 19-mer (SEQ ID NO:11) peptide against the various MMPs was as follows: MMP-2>MMP-3>MMP-8>MMP-7>MMP-9>MMP-1, with inhibitor constants that ranged from 3.1 µM (MMP-2) to 41.1 µM (MMP-1). These data are summarized in Table 4.

TABLE 4

Summary of inhibitor data

| Peptide | Enzyme | Substrate | Ki (µM) |
|---|---|---|---|
| 19-mer (SEQ ID NO:11) | MMP-9 | Collagen | 30.3 |
| 9-mer (SEQ ID NO:12) | MMP-9 | Collagen | 185.9 |
| 10-mer (SEQ ID NO:13) | MMP-9 | Collagen | 221.3 |
| 19-mer (SEQ ID NO:11) | MMP-9 | FRET peptide | 45.2 |
| 9-mer (SEQ ID NO:12) | MMP-9 | FRET peptide | 232.8 |
| 10-mer (SEQ ID NO:13) | MMP-9 | FRET peptide | 327.7 |
| 19-mer (SEQ ID NO:11) | MMP-1 | FRET peptide | 41.1 |
| 19-mer (SEQ ID NO:11) | MMP-2 | FRET peptide | 3.1 |
| 19-mer (SEQ ID NO:11) | MMP-3 | FRET peptide | 6.4 |
| 19-mer (SEQ ID NO:11) | MMP-7 | FRET peptide | 22.8 |
| 19-mer (SEQ ID NO:11) | MMP-8 | FRET peptide | 12.5 |

Anti-Splicing Activity of the 19-mer (SEQ ID NO:11) Peptide:

MMPs are biosynthetically produced in an inactive proenzyme form. Proteolytic cleavage of the proenzyme, often by a separate class of membrane bound MMPs, results in MMP activation. The proenzyme leader sequence is approximately 100 amino acids in length (it varies somewhat from MMP to MMP) and is found at the extreme amino terminus of the protein. Inhibition of proenzyme activation may be a fruitful method of lowering the activity of MMP enzymes in chronic wounds. If these enzymes are incapable of functioning, the rate of extracellular matrix (ECM) degradation will be reduced, which in turn may result in faster rates of chronic wound healing.

Clearly the activation domain peptides (the 19-mer (SEQ ID NO:11), the 9-mer (SEQ ID NO:12), and the 10-mer (SEQ ID NO:13)) inhibit the enzymatic activity of a variety of MMPs. In addition to this activity, the 19-mer (SEQ ID NO:11) peptide prevents the activation of the pro (inactive) form of MMP-9. Thus the 19-mer (SEQ ID NO:11) peptide can lower the overall level of MMP activity in the skin and within chronic wound exudate by inhibiting already activated MMPs or by preventing the activation of newly synthesized pro-MMPs.

Figure 11:
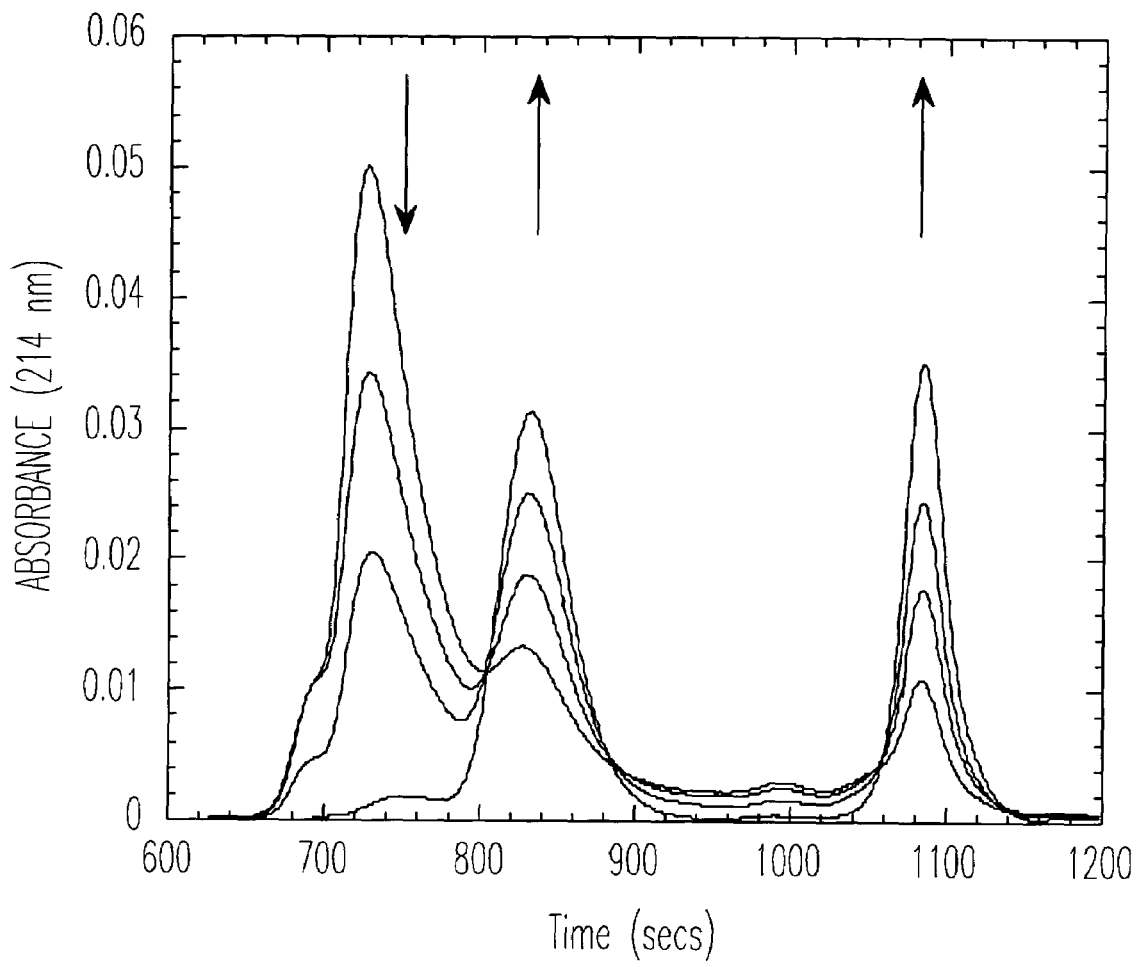
FIG. 11 provides the HPLC elution profiles of a typical splicing reaction. The arrows indicate that the first peak decreases in area over the course of the reaction (pro-MMP-9 peak), while the second two peaks (mature MMP-9 and N-terminal cleavage product, respectively) increase in area.
Figure 12:
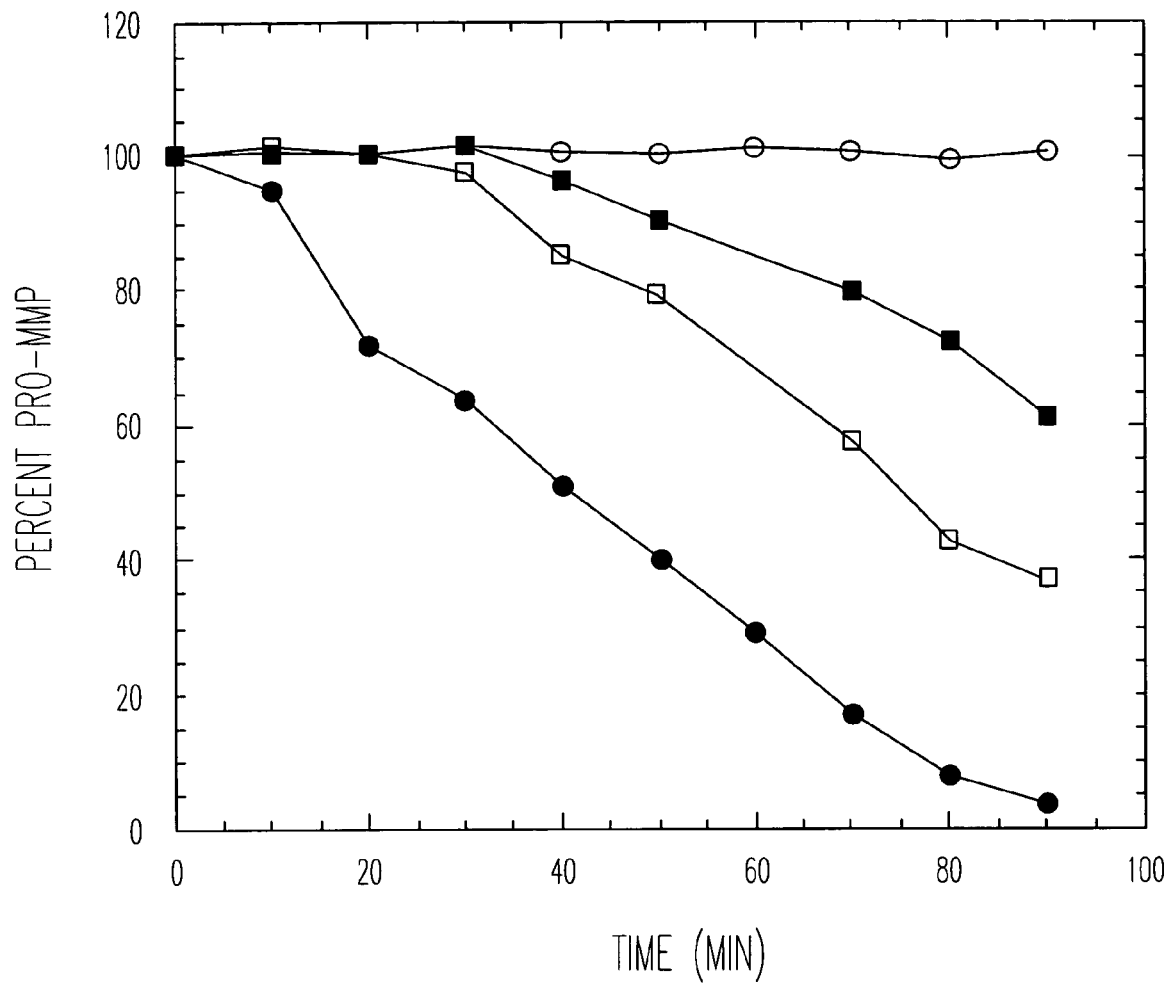
FIG. 12 illustrates the conversion of pro-MMP-9 into N-terminal and C-terminal domains by stromilysin. Pro-MMP-9 was reacted with stromilysin in the presence of zero (closed circles), 0.5 µM (open squares) or 1.0 µM (closed squares) 19-mer (SEQ ID NO:11) peptide. At the times indicated, an aliquot was removed and subjected to HPLC. The pro-MMP peak area was integrated and was set to 100 percent for the zero time point sample. Open circles represent pro-MMP incubated in buffer without stromilysin or 19-mer (SEQ ID NO:11) peptide.

FIG. 11 shows a typical splicing assay. The first peak, eluting at approximately 700 seconds, is pro-MMP-9. As the splicing reaction proceeds, this peak decreases in intensity (as marked with the downwards arrow), and two new peaks appear. The first new peak, eluting at approximately 800 seconds, is mature and active MMP-9. The second new peak, eluting at approximately 1050 seconds, is the prodomain. As the splicing reaction proceeds, the intensity of these two peaks increases (as marked with the upwards arrows). When the reaction is complete, there is no detectable pro-MMP-9 remaining. Titrating the standard splicing reaction with the 19-mer (SEQ ID NO:11) peptide prevents the conversion of pro-MMP-9 into the prodomain and the active enzyme. FIG. 12 shows the results of this titration. Splicing can be inhibited in a dose dependent manner with micromolar 19-mer (SEQ ID NO:11) peptide.

Isothermal Titration Calorimetry

Figure 13A:
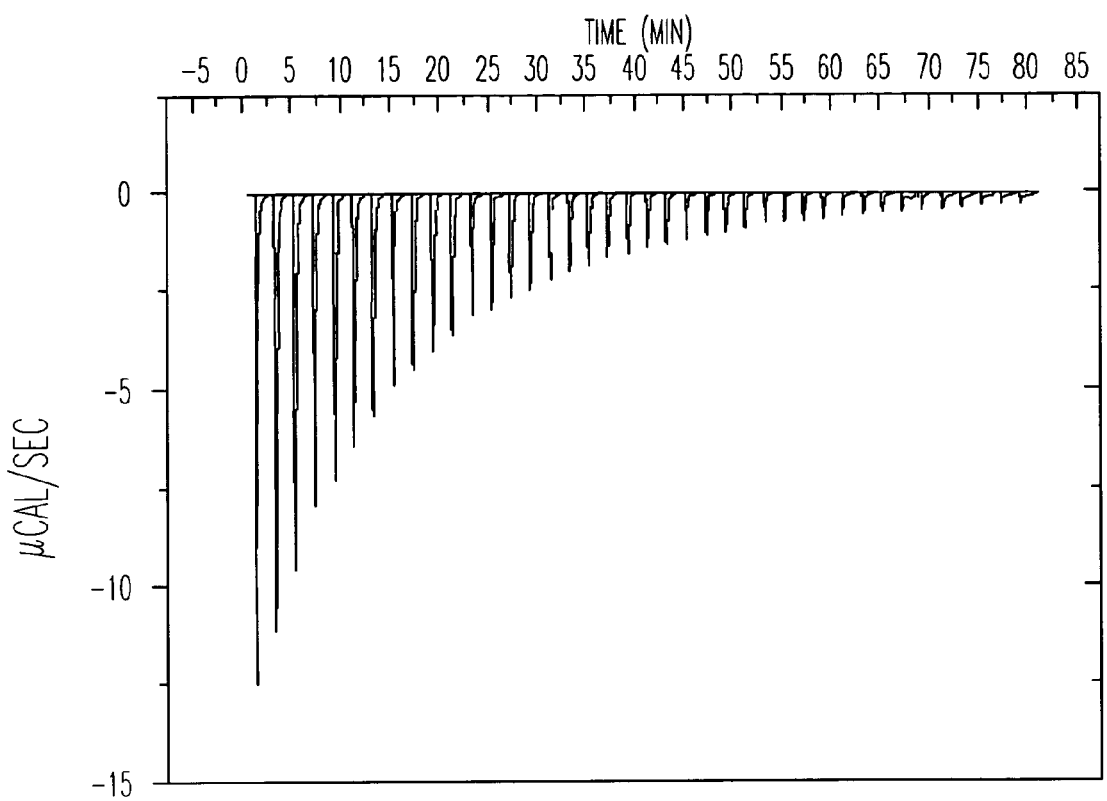
FIG. 13A provides an isothermal titration calorimetry analysis of the interaction of the 19-mer (SEQ ID NO:11) inhibitor peptide with MMP-9. Each peak shows the heat produced by the injection and subsequent binding reaction.
Figure 13B:
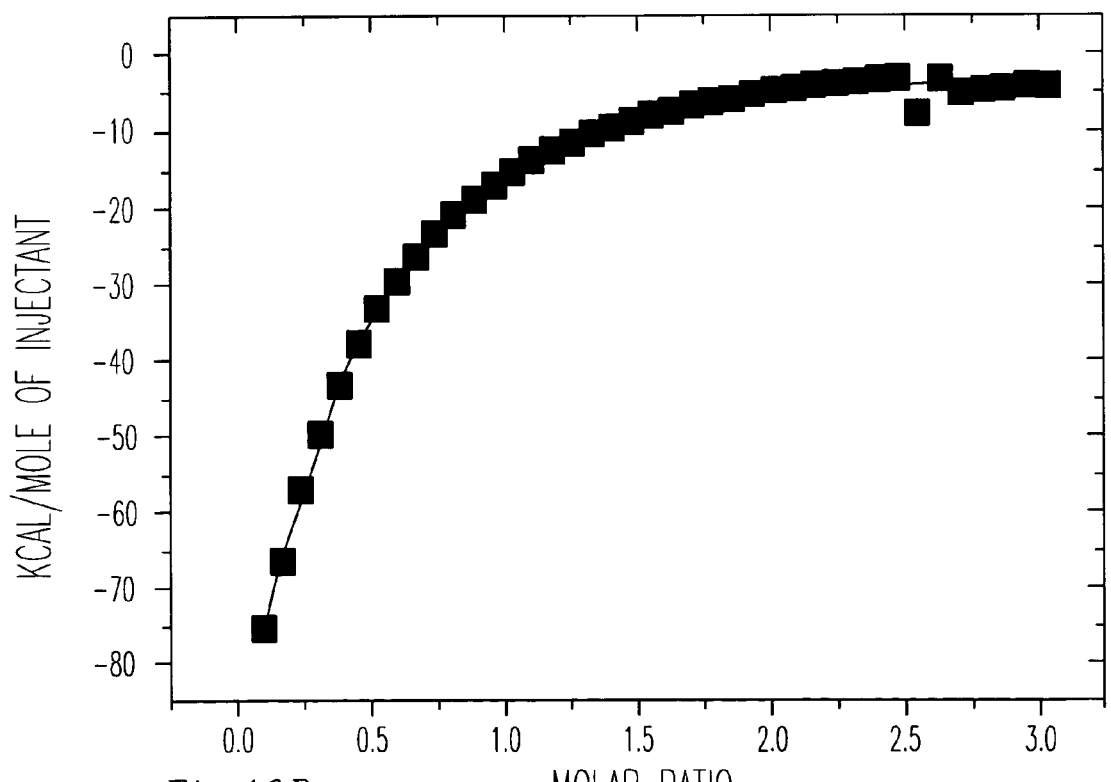
FIG. 13B provides a binding isotherm produced by integrating the value of each injection peak from FIG. 13A with respect to time.

Calorimetry was utilized to determine whether or not the 19-mer (SEQ ID NO:11) peptide formed a stable non-covalent complex with active MMP-9. These data provide an understanding of the mechanism of enzyme inhibition and anti activation properties of the 19-mer (SEQ ID NO:11) peptide. FIG. 13 shows an isothermal calorimetry experiment for the interaction between the 19-mer (SEQ ID NO:11) MMP inhibitor and MMP-9. The peptide was dissolved in 20 mM cacodylate (pH 6.8), 20 mM NaCl at a final concentration of 1 mM. MMP-9 was dialyzed into the same buffer at a final concentration of 20 µM. A series of standard injections were performed as described above. Results for the interaction between MMP-9 and the 19-mer (SEQ ID NO:11) are as follows:

| Stoichiometry: | $0.975 \pm 0.02$ |
| --- | --- |
| ?H (kcal/mol): | $-26.1 \pm 1.45$ |
| ?S (cal mol$^{-1}$ K$^{-1}$): | $-11.6 \pm 2.2$ |
| $K_A$ (M$^{-1}$): | $1.65 \times 10^6 \pm 4.5 \times 10^4$ |

These results indicate that the interaction between the 19-mer (SEQ ID NO:11) peptide and MMP-9 is enthalpically driven, that is ?H is negative. The reaction is not favored entropically as evidenced by the negative value of ?S. However, the enthalpic term is larger in magnitude than the term, T?S, hence the overall free energy (?G) is negative.

Figure 14A:
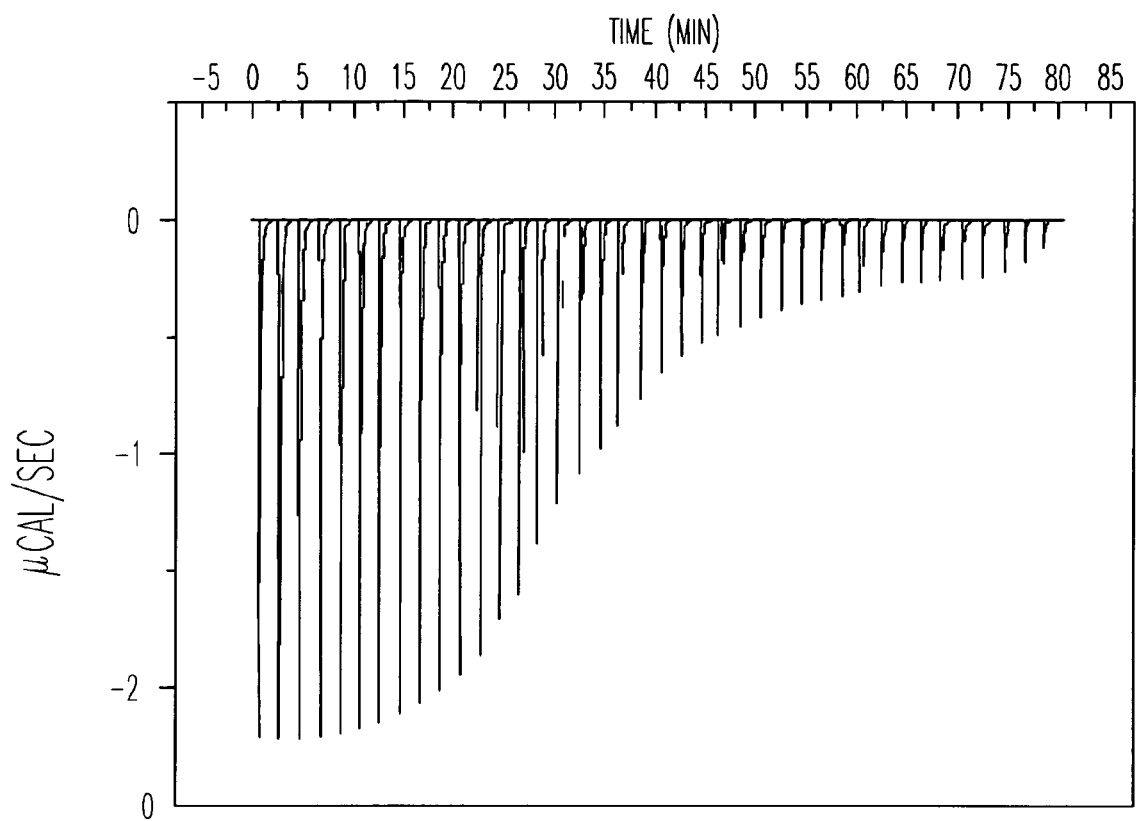
FIG. 14A provides the raw isothermal calorimetry data for the titration of 19-mer (SEQ ID NO:11) (1 mM) into MMP-2 (20 µM) in 20 mM cacodylate (pH 6.8), 10 mM NaCl at 25° C. Each peak shows the heat produced by the injection and subsequent binding reaction.
Figure 14B:
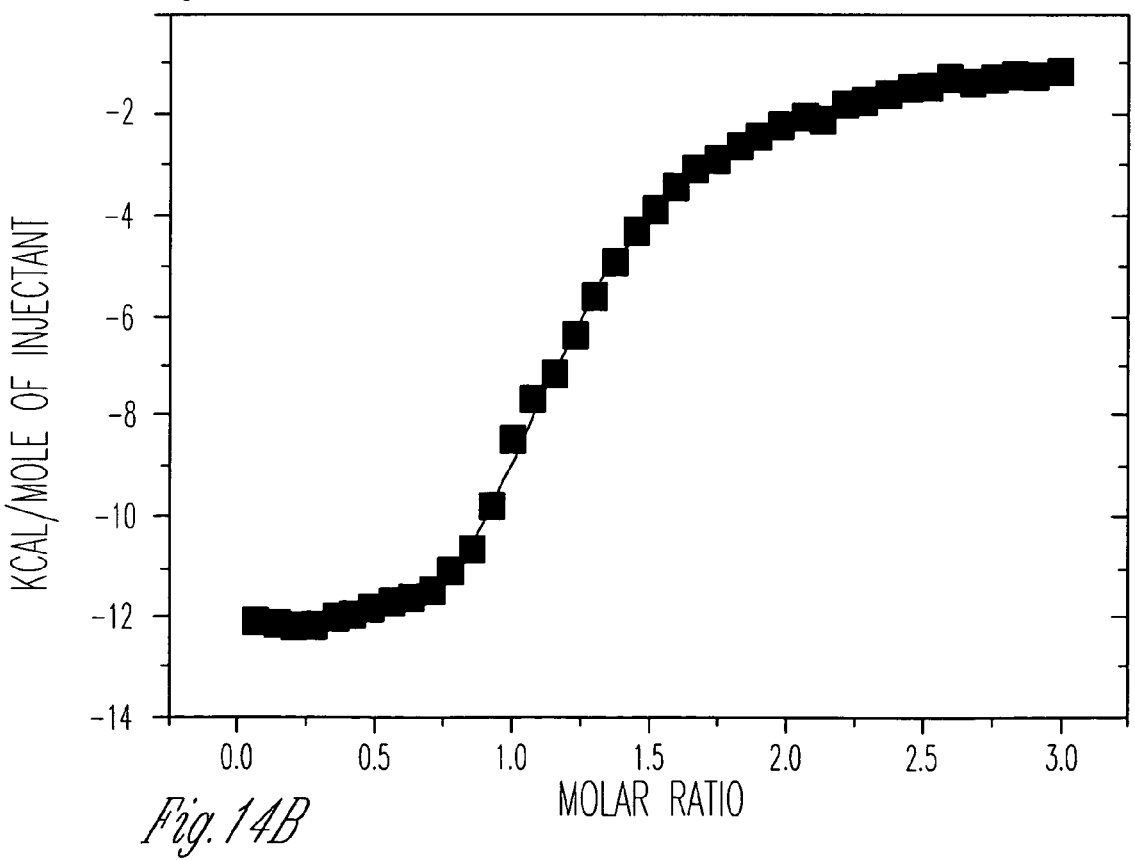
FIG. 14B provides a binding isotherm produced by integrating the value of each injection peak from FIG. 14A with respect to time.

The 19-mer (SEQ ID NO:11) reaction with MMP-2 was observed and found to be enthalpically driven and entropically unfavorable. The isothermal calorimetry analysis shown in FIG. 14 was produced by titration of the 19-mer (SEQ ID NO:11) with MMP-2. The following values were obtained from these experiments.

| Stoichiometry: | $0.99 \pm 0.03$ |
| --- | --- |
| ?H (kcal/mol): | $-15.4 \pm 2.05$ |
| ?S (cal mol$^{-1}$ K$^{-1}$): | $-21.1 \pm 1.8$ |
| $K_A$ (M$^{-1}$): | $2.40 \times 10^6 \pm 3.7 \times 10^4$ |

Hence, the binding reactions are entropically unfavorable, possibly because of a loss of configurational entropy upon peptide binding. A fully flexible peptide contains a large numbers of degrees of freedom that can be constrained in a binding reaction. In all binding cases, the peptide to MMP stoichiometry is 1:1, which indicates that a single 19-mer (SEQ ID NO:11) peptide interacts with a single MMP molecule.

Surface Plasmon Resonance

Figure 15:
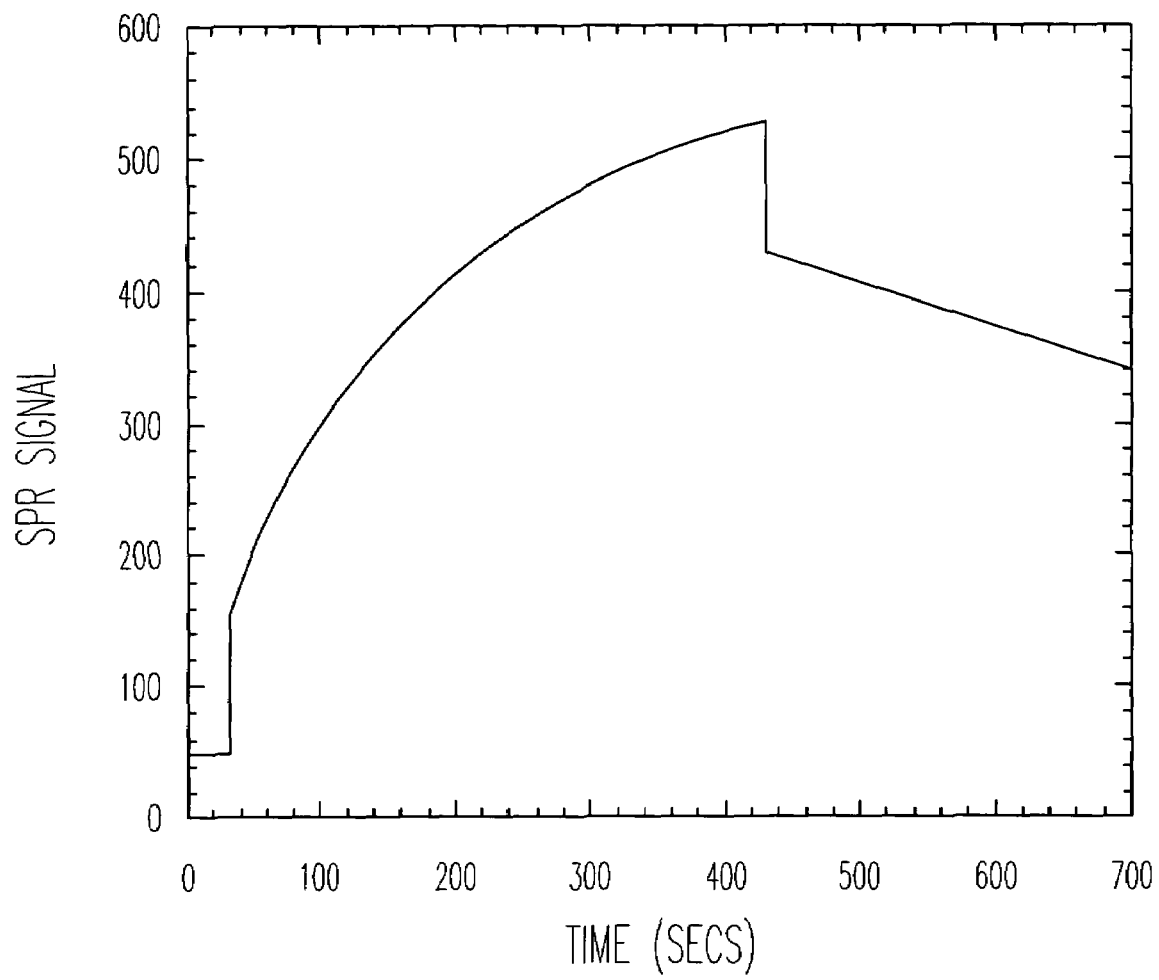
FIG. 15 provides a surface plasmon resonance binding isotherm generated when the 19-mer (SEQ ID NO:11) peptide is flowed over a surface of immobilized MMP-9.

The binding of the 19-mer (SEQ ID NO:11) to MMP-9 was kinetically studied using the technique of surface plasmon resonance (SPR). A sensor chip was constructed by tethering active MMP-9 to the surface of a BIACore, Inc. CM-5 chip following the standard chemistries that were recommended by the manufacturer. A solution of the 19-mer (SEQ ID NO:11) peptide was passed over the MMP-9 surface in a BIACore-X™ instrument. Binding and dissociation were monitored in real time. A typical binding isotherm is shown in FIG. 15. The association phase (30–430 seconds) was best fit to a single binding site model and resulted in an association rate constant ($k_a$) of $2.2 \times 10^4$ M$^{-1}$s$^{-1}$. The dissociation phase (440–700 seconds) was similarly fit and resulted in a dissociation rate constant ($k_d$) of $4.1 \times 10^{-3}$ s$^{-1}$. The calculated equilibrium association constant ($K_a = k_a/k_d$) of $5.3 \times 10^6$ was in close agreement with the thermodynamic data. There was an observed bulk transport effect of approximately 100 response units at the start of the dissociation phase that was not modeled. Thus binding of the 19-mer (SEQ ID NO:11) peptide to MMP-9 is both kinetically and thermodynamically favorable.

Viability Assays

Figure 16:
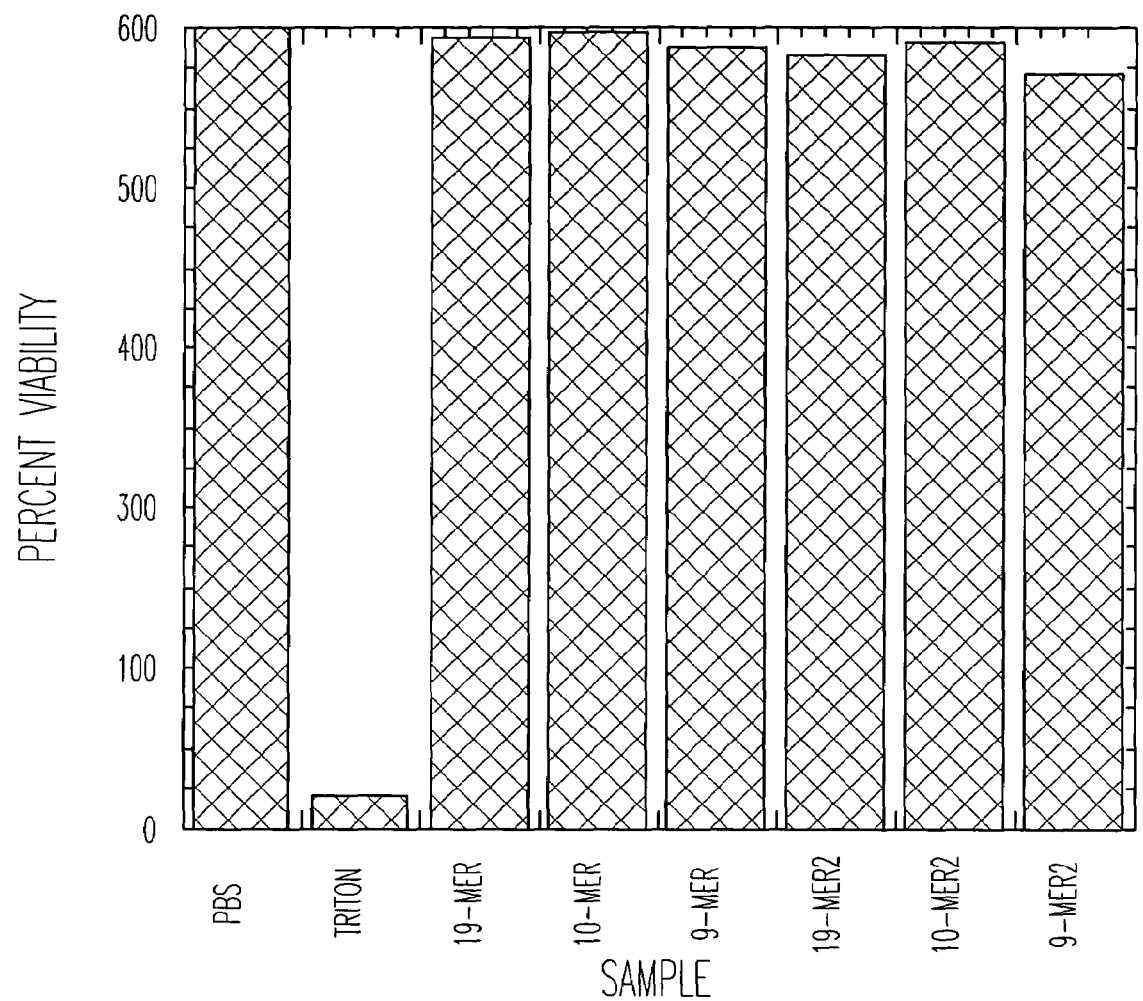
FIG. 16 provides a bar graph showing the percent living cells, relative to a positive control, in a skin model after treatment with two concentrations of peptide. The first sample, treated with phosphate buffered saline (PBS), is the positive control used to establish the cell count representing 100% viability. The second sample is a negative control where cells were exposed to 1% Triton-X100, showing that the assay can detect cell death. The next three samples are the 19-mer (SEQ ID NO:11), the 10-mer (SEQ ID NO:13), and the 9-mer (SEQ ID NO:12) peptides used at a concentration of 500 µM. The final three samples are the 19-mer (SEQ ID NO:11), the 10-mer (SEQ ID NO:13), and the 9-mer (SEQ ID NO:12) peptides used at a concentration of 2 mM. Data shown represent the average of three samples.

Unlike many small molecule MMP inhibitors, the three peptides in this study were not toxic to cells when dosed onto the EpiDerm skin model. FIG. 16 shows that peptide at two concentrations (500 µM and 2 mM) resulted in only a slight reduction in viability compared to a PBS control. The total average viability of the peptides was 97.6% (for the 19-mer (SEQ ID NO:11)), 89.6% (for the 10-mer (SEQ ID NO:13)), and 95.8% (for the 9-mer (SEQ ID NO:12)). These results indicate that the inventive therapeutic approach to cancer treatment, cancer prevention and wound healing is not toxic to mammalian cells. The data plotted in FIG. 16 are an average of triplicate samples. The standard deviation for the viability ranged from 2.2 to 3.7 for the study and showed no correlation to dose or peptide identity. Viability was slightly lower at the higher peptide concentrations.

These results show that the peptides are not toxic in an EpiDerm™ skin model, that they are kinetically and entropically favored to form binding complexes with MMPs, and that they inhibit enzymatic activity and prevent activation of matrix metalloproteinases.

EXAMPLE 2

Wound Healing by Peptide Inhibitors

Methods

Wounds were created in C57BL6/KsJ db/db mice with a 4 mm biopsy punch. The mice were obtained from The Jackson Laboratories and were aged 3–7 months before the onset of the wounding protocol. All mice were anesthetized prior to wounding. Two wounds were introduced onto the upper back of each animal by pulling the skin away from underlying structures and pushing the punch through the isolated skin. Typically, wounds were created to an average depth of 1.7 mm, with a range of 1.3 to 2.2 mm. No muscle involvement occurred during the course of wounding. Immediately after wounding the wounds were treated either with normal saline (to serve as the non treated control group) or with 5 µL of 20 µg/mL 19-mer peptide (SEQ ID NO:11).

Each day the wounds were digitally photographed and wound areas were determined by computer integration of the photographs. All wound treatments and the subsequent data analyses were performed in a blind manner (see e.g., Brown et al., 1994). Wound area at the time of wounding (day 0) was arbitrarily set to a relative value of 1 for all wounds; such that subsequent wound areas were converted to relative wound areas by dividing the wound area at day n by the wound area at day zero.

Figure 17:
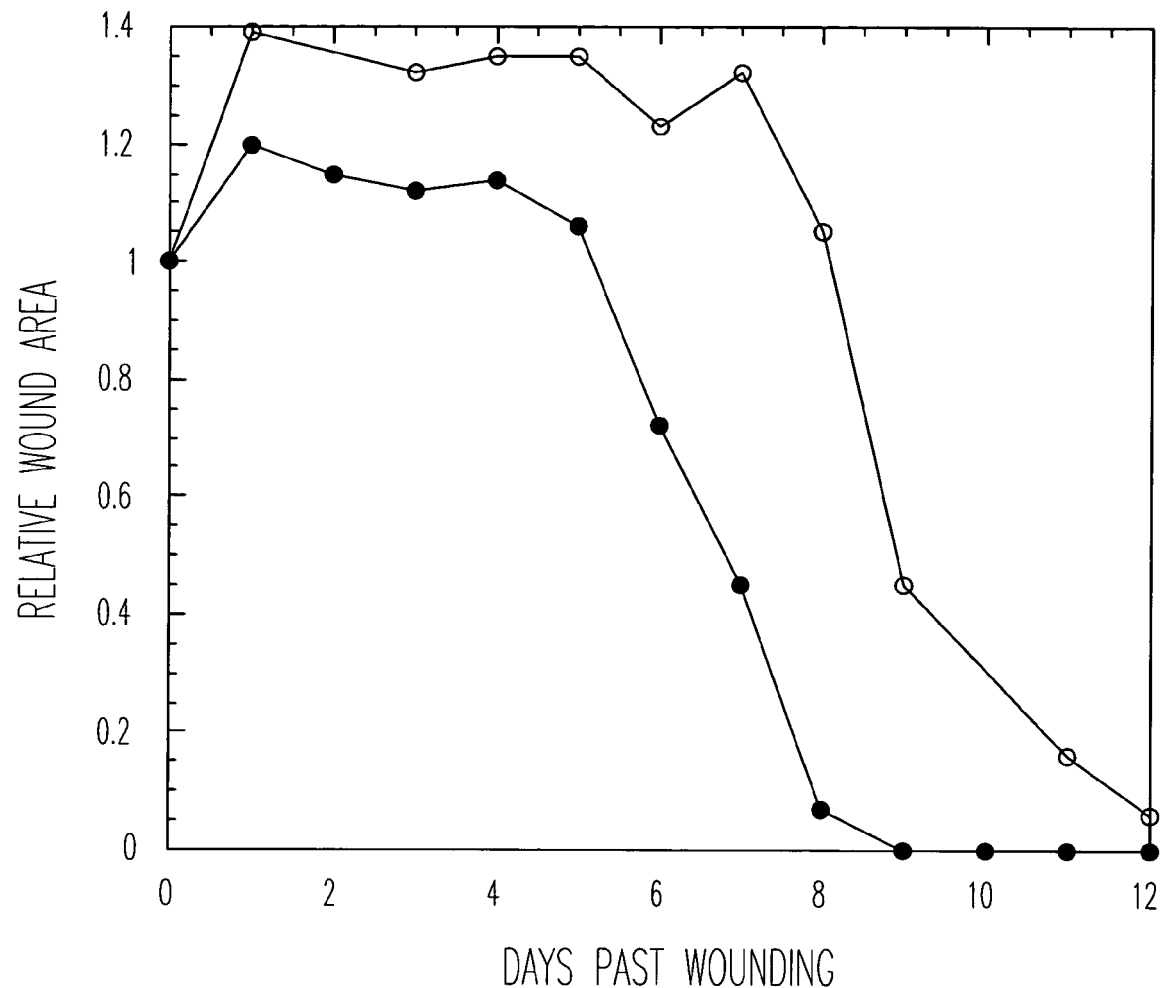
FIG. 17 graphically depicts the time course of wound healing in db/db diabetic mice. The plot shows the relative average wound area versus days post wounding for mice treated with either normal saline (open circles) or 20 µg/mL of the 19-mer peptide (SEQ ID NO:11) (closed circles). Data presented show the mean relative wound diameter derived from ten subject animals.

Results:

As can be seen in FIG. 17, the application of a single dose of the 19-mer peptide (at the time of wounding, day zero) greatly accelerated the time to full wound closure in the diabetic mouse model. On average, wounds treated with the 19-mer peptide closed in 9 days post wounding compared to 14 days in the saline treated control. In addition, wounds treated with the 19-mer peptide (SEQ ID NO:11) showed a reduction in wound inflammation at day one post wounding. Also of note is the observation that the 19-mer peptide (SEQ ID NO:11) treated wounds began the contraction process faster than did the saline treated control wounds (day 5 versus day 8).

EXAMPLE 3

Peptide Inhibitors Inhibit Chondrosarcoma Cell Growth

In this experiment the 19-mer (SEQ ID NO:11) peptide was tested to ascertain whether it could inhibit growth of chrondrosarcoma cells.

Materials and Methods

Human chondrosarcoma cells (SW1351) were purchased from the American Type Culture Collection (ATCC No. HTB-94). A frozen vial of cells was thawed by gentle agitation in a 37° C. water bath for about 2 minutes. The vial was decontaminated with 70% ethanol and the cells were transferred to a T75 flask containing pre-warmed Leibovitz's L-15 medium (ATCC Catalog No. 30-2008) with 10% fetal bovine serum. The culture as incubated at 37° C. until 80% confluence. The culture medium was removed and the cells were dissociated from the T75 flask using 3 ml 0.25% trypsin, 0.03 mM EDTA at 37° C. After incubation for 5 minutes, 8 ml culture medium was added to stop trypsinization. The cells were counted with trypan blue and then seeded in 96 well plates at a density of about 2500 cells/well.

The cells were then treated with $10^{-6}$, $10^{-5}$ or $10^{-4}$ M of the 19-mer (SEQ ID NO:11), the 9-mer (SEQ ID NO:12) or the 10-mer (SEQ ID NO:13) peptides. Six separate cell cultures were tested at each concentration of each peptide (n=6). Control cells received culture medium only.

Cell cultures were then incubated at 37° C. in an atmosphere of 5% $CO_2$. Cell proliferation was determined after 18 or 72 hr by using the CellTiter 96 Aqueous One Solution purchased from Promega (Catalog No. TB245). Briefly, the CellTiter solution was warmed up to room temperature. Twenty microliters of the solution was added to each well. Cells were incubated at 37° C. for 1–2 hours. The absorbance at 490 nm was then recorded using a 96 well plate reader. The data were statistically analyzed using a Student T test. Differences were considered significant at the level of $p<0.05$.

Results

Figure 18:
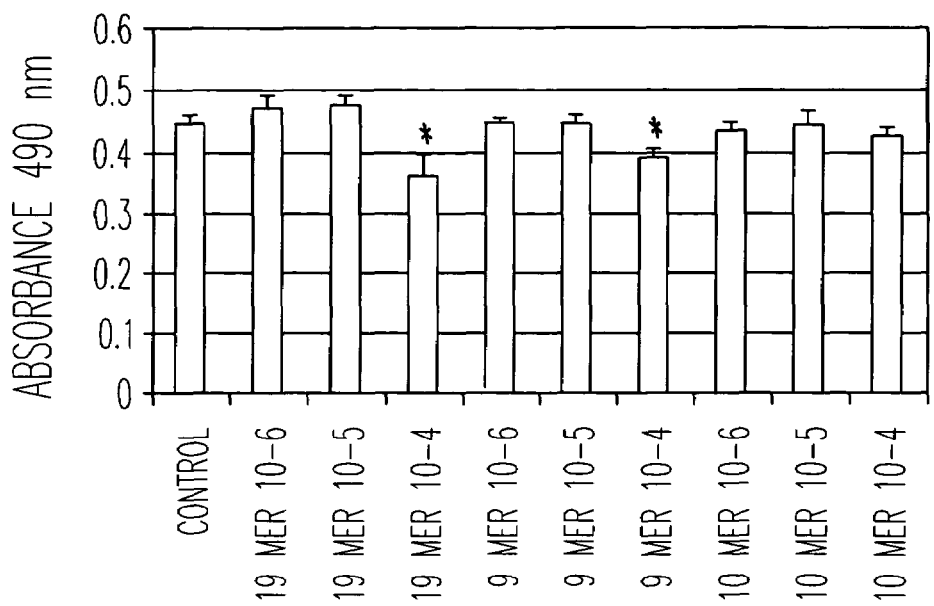
FIG. 18 illustrates that 18 hours of exposure to the 19-mer (SEQ ID NO:11), and the 9-mer (SEQ ID NO:12) peptide significantly inhibits or depresses growth of chrondrosarcoma cells compared to untreated chrondrosarcoma cells. This figure provides a bar graph of the absorbance at 490 nm for chrondrosarcoma cells treated with the 19-mer (SEQ ID NO:11), the 9-mer (SEQ ID NO:12) or the 10-mer (SEQ ID NO:13) peptides. As illustrated, the growth of cells treated with the 19-mer (SEQ ID NO:11) or the 9-mer (SEQ ID NO:12) was substantially less than growth of negative control cells (untreated chrondrosarcoma cells). The symbol * indicates that a statistically significant decrease in growth was observed compared to the control group (p<0.05).
Figure 19:
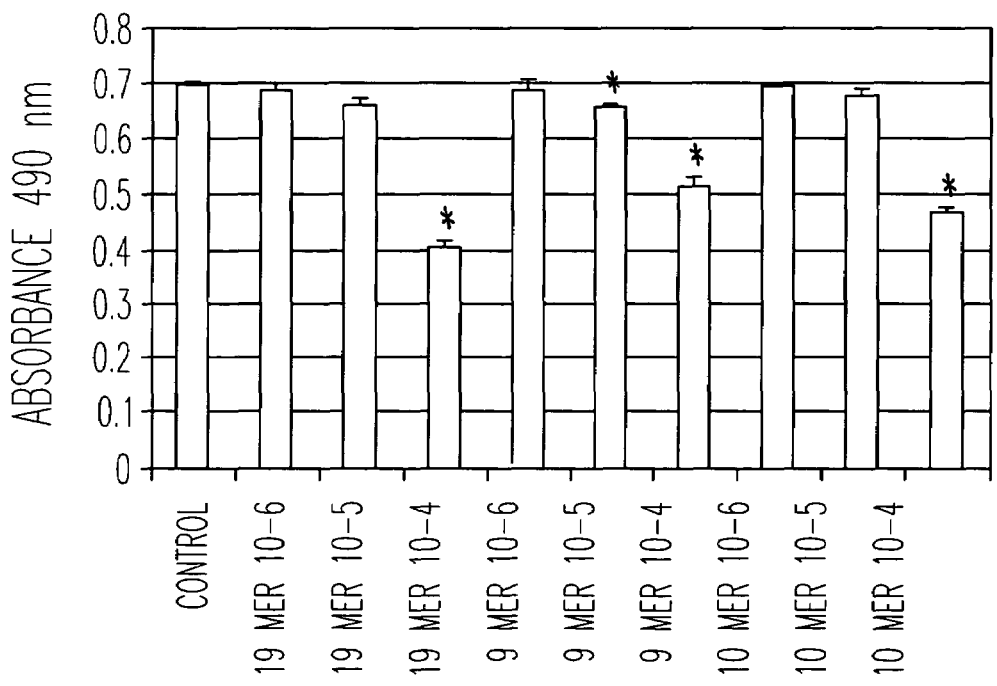
FIG. 19 further illustrates that 72 hours of exposure to the 19-mer (SEQ ID NO:11), 10-mer (SEQ ID NO:13) and the 9-mer (SEQ ID NO:12) peptide significantly inhibits or depresses growth of chrondrosarcoma cells compared to untreated chrondrosarcoma cells. This figure provides a bar graph of the absorbance at 490 nm for chrondrosarcoma cells treated with the 19-mer (SEQ ID NO:11), the 9-mer (SEQ ID NO:12) or the 10-mer (SEQ ID NO:13) peptides. As illustrated, the growth of cells treated with the 19-mer (SEQ ID NO:11), 10-mer (SEQ ID NO:13) or the 9-mer (SEQ ID NO:12) was substantially less than growth of negative control cells (untreated chrondrosarcoma cells). The symbol * indicates that a statistically significant decrease in growth was observed compared to the control group (p<0.05).

As shown in FIG. 18, at concentrations of $10^{-4}$ M the 19-mer (SEQ ID NO:11) and 9-mer (SEQ ID NO:12) peptides significantly inhibited SW1353 chondrosarcoma cell proliferation after 18 hours of incubation. At 18 hr., the 10-mer (SEQ ID NO:13) did not show any significant effect at the three concentrations tested. However, after 72 hours of treatment, all three peptides at $10^{-4}$ M concentration, as well as the 9-mer (SEQ ID NO:12) at $10^{-5}$ M concentration, significantly reduced the proliferative activity of the chondrosarcoma cells (FIG. 19).

Hence, the peptides of the invention can significantly reduce growth of chondrosarcoma cells.

REFERENCES

The following references and any other references cited herein are incorporated by reference.

Agren, M. S. (1999). Matrix metalloproteinases (MMPs) are required for re-epithelialization of cutaneous wounds. Arch. Dermatol. Res. 291, 583–590.

Baker, E., et al. Proteinases, their inhibitors, and cytokine profiles in acute wound fluid. Wound Repair Regen. September–October 2000; 8(5): 392–8.

Becker, J. W., Marcy, A. I., Rokosz, L. L., Axel, M. G., Burbaum, J. J., Fitzgerald, P. M., Cameron, P. M., Esser, C. K., Hagmann, W. K., Hermes, J. D., and Springer, J. P. (1995). Stromelysin-1: Three dimensional structure of the inhibited catalytic domain and of the C-truncated proenzyme. Protein Sci. 4, 1966–76.

Berend K. R. et al. (1999) Association between ratio of matrix metalloproteinase-1 to tissue inhibitor of metalloproteinase-1 and local recurrence, metastasis and survival in human chondrosarcoma. J. Bone Joint Surg. Am. 816: 893–95.

Brown, R L., Breeden, M P., and Greenhalgh, M D., (1994). PDGF and TGF-a act synergistically to improve wound healing in the genetically diabetic mouse. J. Surg. Res. 56, 562–570.

Browner, M. F., Smith, W. W., Castelhano, A. L. (1995). Matrilysin-inhibitor complexes: Common themes among 18 metalloproteinases. Biochemistry 34, 6602–10.

Calvin, M. Cutaneous wound repair. Wounds 1998; 10(1): 12–32.

Di Colandrea, T., Wang, L., Wille, J., D'Armiento, J., and Chada, K. K. (1998). Epidermal expression of collagenase delays wound healing in transgenic mice. J. Invest. Dermatol. 111, 1029–1033.

Duivenvoorden, W. C. M., Hirte, H. W., and Singh, G. (1997). Use of tetracycline as an inhibitor of matrix metalloproteinase activity secreted by human bone metastasizing cancer cells. Invasion and Metas. 17, 312–322.

Fernandez-Catalan, C., Bode, W., Huber, R., Turk, D., Calvete, J. J., Lichte, A., Tschesche, H., and Maskos, K. (1998). Crystal structure of the complex formed by membrane type-1 matrix metalloproteinase with the tissue inhibitor of metalloproteinases-2, the soluble progelatinase A receptor. EMBO J. 17, 5238–48.

Freire, E., van Osdol, W W., Mayorga, O L, and Sanchez-Ruiz, J M. (1990). Calorimetrically determined dynamics of complex unfolding transitions in proteins. Annu Rev Biophys Biophys Chem.19, 159–88.

Gomis-Ruth, F. X., Maskos, K., Betz, M., Bergner, A., Huber, R., Suzuki, K., Yoshida, N., Nagase, H., Brew, K., Bourenkov, G. P., Bartunik, H., and Bode, W. (1997). Mechanism of inhibition of the human matrix metalloproteinase stromelysin-1 by TIMP-1. Nature 389, 77–81.

Grams, F., Reinemer, P., Powers, J. C., Kleine, T., Pieper, M., Tschesche, H., Huber, R., Bode, W. (1995). X-ray structures of human neutrophil collagenase complexed with peptide hydroxamate and peptide thiol inhibitors: Implications for substrate binding and rational drug design. Eur. J. Biochem. 228, 830–834.

Guex, N. and Peitsch, M. C. (1997). Swiss Model and the Swiss-PdbViewer: An environment for comparative protein modeling. Electrophoresis 18, 2714–2723.

Higgins, D G., Bleasby, A J., and Fuchs, R. (1992). CLUSTAL V: improved software for multiple sequence alignment. Comput Appl Biosci.,8(2),189–91.

Howard, E. W., Bullen, E. C., and Banda, M. J. (1991). Preferential inhibition of 72 and 92 kDa gelatinase by tissue inhibitor of metalloproteinase-2. J. Biol. Chem. 266, 13070–13075.

Huang, W., Suzuki, K., Nagase, H., Arumugam, S., Van Doren, S. R., and Brew, K. (1996). Folding and characterization of the amino terminal domain of human tissue inhibitor of metalloproteinases-1 (TIMP-1) expressed at high yield in *E. coli*. FEBS Lett. 384, 155–161.

Karlsson, R., and Falt, A. (1997). Experimental design for kinetic analysis of protein-protein interactions with surface plasmon resonance biosensors. J. Immunol. Meths. 200, 121–33.

Kerkela, E. et al. (2001) Human macrophage metalloelastase (MMP-12) expression is induced in chondrocytes during fetal development and malignant transformation. Bone 29: 487–93.

Kim, Y. et al. Endostatin blocks VEGF-mediated signaling via direct interaction with KDR/Flk-1. J Biol Chem 2002; May 23.

Lakowicz, J. R. (1983). Principles of Fluorescence Spectroscopy, Chapter 10, Plenum Press, New York, London.

Levenson, S., et al. The Healing of Rat Skin Wounds. Ann. Surg. 1965; 161: 293–308.

Levit, S., and Berger, A. (1976). Ribonuclease S-peptide. A model for molecular recognition. J. Biol. Chem. 251, 1333–9.

Levy, D. E., Lapierre, F., Liang, W., Ye, W., Lange, C. W., Li, X., Grobelny, D., Casabonne, M., Tyrrell, D., Holme, K., Nadzan, A., and Galardy, R. E. (1998). Matrix metalloproteinase inhibitors: A structure activity study. J. Med. Chem. 41, 199–223.

Li, J., Brick, P., O'Hare, M. C., Skarzynski, T., Lloyd, L. F., Curry, V. A., Clark, I. M., Bigg, H. F., Hazleman, B. L., Cawston, T. E. et al.(1995). Structure of full-length porcine synovial collagenase reveals a C-terminal domain containing a calcium-linked, four-bladed beta-propeller. Structure 3, pp. 541–49.

Libson, A. M., Gittis, A. G., Collier, I. E., Marmer, B. L., Goldberg, G. I., and Lattman, E. E. (1995). Crystal structure of the haemopexin-like C terminal domain of gelatinase A. Nat. Struct. Biol. 2, 938–42.

Lofas, S., Johnsson, B., Tegendahl, K., and Ronnberg, I. (1993). Dextran modified gold surfaces for surface plasmon resonance biosensors; immunoreactivity of immobilized antibodies and antibody-surface interaction studies. J. Colloid Interface Sci. 65, 423–431.

Morton, T. A., Myska, D. G., and Chaiken, I. M. (1995). Interpreting complex binding kinetics from optical biosensors: A comparison of analysis by linearization, the integrated rate equation, and numerical integration. Anal. Biochem. 227, 176–185.

Moses, M. A., Marikovsky, M., Harper, J. W., Vogt, P., Eriksson, E., Klagsbrun, M. and Langer, R. (1996). Temporal study of the activity of matrix metalloproteinases and their endogenous inhibitors during wound healing. J. Cell. Biochem. 60, 379–386.

Nwomech, B., et al. Dynamics of the matrix metalloproteinases MMP-1 and MMP-8 in acute open human dermal wounds. Wound Repair Regen. March–April 1998; 6(2): 127–34.

Odake, S., Morita, Y., and Morikawa, T. (1994). Inhibition of matrix metalloproteinases by peptidyl hydroxamic acids. Biochem. Biophys. Res. Comm. 199, 1442–1446.

Olson, M. W., Gervasi, D. C., Mobashery, S., and Fridman, R. (1997). Kinetic analysis of the binding of human matrix metalloproteinase 2 and 9 to tissue inhibitor of metalloproteinase (TIMP)-1 and TIMP-2. J. Biol. Chem. 272, 29975–29983.

O'Shannessy, D. J., Brigham-Burke, M., Soneson, K. K, Hensley, P., and Brooks, I. (1993). Determination of rate and equilibrium binding constants for macromolecular interactions using surface plasmon resonance: use of non linear least squares analysis methods. Anal. Biochem. 212, 457–468.

Reinemer, P., Grams, F., Huber, R., Kleine, T., Schnierer, S., Pieper, M., Tschesche, H., Bode, W. (1994). Structural implications for the role of the N terminus in the super-activation of collagenase: A crystallographic study. FEBBS Lett. 338, 227–33.

Saarialho-Kere, U. K. (1998). Patterns of matrix metalloproteinase and TIMP expression in chronic ulcers. Arch. Dermatol. Res. 290 (suppl), 47–54.

Sakamoto A. et al. (1999) Expression of membrane type 1 matrix metalloproteinase, matrix metalloproteinase 2 and tissue inhibitor of metalloproteinase 2 in human cartilaginous tumors with special emphasis on mesenchymal and dedifferentiated chrondrosarcoma. J. Cancer Res. Clin. Oncol. 125: 541–48.

Sayle, R. A. and Milner-White, E. J. (1995). RasMol: Biomolecular graphics for all. Trends in Biochemical Sciences 20, 374–376.

Segel, I H. (1993) Enzyme Kinetics: Behavior and analysis of rapid equilibrium and steady-state enzyme systems. Wiley Classics Library, John Wiley and Sons, Inc. New York.

Singer, A. J., et al. Cutaneous Wound Healing. New Eng. J. of Med. 1999; Vol.341, No. 10:738–746.

Soderstrom et al. (2001) Expression of matrix metalloproteinase and tissue inhibitors of metalloproteinases in human chondrosarcoma, APMIS 109: 305–15.

Su, J-L., Becherer, D., Edwards, C., Bukhart, W., McMgeehan, G. M., and Champion, B. R. (1995). Monoclonal antibodies against human collagenase and stromelysin. Hybridoma. 14, 383–390.

Taylor, K. B., Windsor, J. L., Caterina, N. C. M., Bodden, M. K., and Engler, J. A. (1996). The mechanism of inhibition of collagenase by TIMP-1. J. Biol. Chem. 271, 23938–23945.

Tuuttila, A., Morgunov, E., Bergmann, U., Lindquist, Y., Maskos, K., Fernandez-Catalan, C., Bode, W., Tryggvason, K., and Schneider, G. (1998). Three dimensional structure of human tissue inhibitor of metalloproteinases-2 at 2.1 Å resolution. J. Mol. Biol. 284, 1133–1140.

U.S. markets for wound management products. Irvine, Calif.: Medical Data International, August 1997.

Vaalamo, M., Weckroth, M., Puolakkainen, P., Kere, J., Saarinen, P., Lauharanta, J., and Saarialho-Kere, U. K. (1996). Patterns of matrix metalloproteinase and TIMP-1 expression in chronic and normally healing human cutaneous wounds. Brit. J. Dermatol. 135, 52–59.

Vaalamo, M., Mattila, L., Johansson, N., Kariniemi, A- L., Karjalainen-Lindsberg, L., Kahari, V-M., and Saarialho-Kere, U. K. (1997). Distinct populations of stromal cells express collagenase-3 (MMP-13) and collagenase-1 (MMP-1) in chronic ulcers, but not in normally healing wounds. J. Investig. Dermatol. 109, 96–101.

Weckroth, M., Vaheri, A., Lauharanta, J., Sorsa, T., and Konttinen, Y. T. (1996). Matrix metalloproteinases, gelatinases, and collagenases in chronic leg ulcers. J. Investig. Dermatol. 108, 1119–1124.

Wojtowicz-Praga, S. M., Dickson, R. B., and Hawkins, M. J. (1997). Matrix metalloproteinase inhibitors. Investigational new Drugs. 15, 61–75.

All patents and publications referenced or mentioned herein are indicative of the levels of skill of those skilled in the art to which the invention pertains, and each such referenced patent or publication is hereby incorporated by reference to the same extent as if it had been incorporated by reference in its entirety individually or set forth herein in its entirety. Applicants reserve the right to physically incorporate into this specification any and all materials and information from any such cited patents and publications.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. The methods and processes illustratively described herein suitably may be practiced in differing orders of steps, and that they are not necessarily restricted to the orders of steps indicated herein or in the claims. It is also that as used herein and in the appended claims, the singular forms "a," "an," and "the" include plural reference unless the context clearly dictates otherwise. Thus, for example, a reference to "a host cell" includes a plurality (for example, a culture or population) of such host cells, and so forth. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

What is claimed:

1. A method for decreasing growth of chondrosarcoma cells that comprises contacting a chondrosarcoma cell with an effective amount of a peptide selected from the group consisting of SEQ ID NO:11, SEQ ID NO:12, or SEQ ID NO:13.

2. The method of claim 1, wherein the peptide is SEQ ID NO: 11.

3. A method for decreasing growth of chondrosarcoma cells in a mammal that comprises administering an effective amount of a peptide selected from the group consisting of SEQ ID NO: 11, SEQ ID NO:12 or SEQ ID NO:13 to the mammal.

4. The method of claim 1 or 3, wherein decreasing growth of chondrosarcoma cells decreases growth of conventional chondrosarcoma, myxoid chondrosarcoma, mesenehymal chondrosarcoma, clear cell chondrosarcoma, or dedifferentiated (spindle cell) chondrosarcoma.

5. The method of claim 3, wherein the chondrosarcoma cells comprise a tumor.

6. The method of claim 5, wherein the tumor is metastatic, non-metastatic, vascularized, non-vascularized, hard or soft.

7. The method of claim 5, wherein the peptide is administered locally to the tumor.

* * * * *

SEQUENCE LISTING

```
<160> NUMBER OF SEQ ID NOS: 21

<210> SEQ ID NO 1
<211> LENGTH: 8
<212> TYPE: PRT
<213> ORGANISM: Homo sapiens

<400> SEQUENCE: 1

Pro Arg Cys Gly Val Pro Asp Val
1               5

<210> SEQ ID NO 2
<211> LENGTH: 44
<212> TYPE: PRT
<213> ORGANISM: Homo sapiens

<400> SEQUENCE: 2

Met Gln Lys Phe Phe Gly Leu Pro Gln Thr Gly Asp Leu Asp Gln Asn
1               5                   10                  15

Thr Ile Glu Thr Met Arg Lys Pro Arg Cys Gly Asn Pro Asp Val Ala
            20                  25                  30

Asn Tyr Asn Phe Phe Pro Arg Lys Pro Lys Trp Asp
        35                  40

<210> SEQ ID NO 3
<211> LENGTH: 50
<212> TYPE: PRT
<213> ORGANISM: Homo sapiens

<400> SEQUENCE: 3
```

Met Gln Ser Phe Phe Gly Leu Glu Val Thr Gly Lys Leu Asp Asp Asn
1               5                   10                  15

Thr Leu Asp Val Met Lys Lys Pro Arg Cys Gly Val Pro Asp Val Gly
            20                  25                  30

Glu Tyr Asn Val Phe Pro Arg Thr Leu Lys Trp Ser Lys Met Asn Leu
        35                  40                  45

Thr Tyr
    50

<210> SEQ ID NO 4
<211> LENGTH: 56
<212> TYPE: PRT
<213> ORGANISM: Homo sapiens

<400> SEQUENCE: 4

Met Gln Lys Phe Phe Gly Leu Pro Glu Thr Gly Lys Leu Ser Pro Arg
1               5                   10                  15

Val Met Glu Ile Met Gln Lys Pro Arg Cys Gly Val Pro Asp Val Ala
            20                  25                  30

Glu Phe Ser Leu Met Pro Asn Ser Pro Lys Trp His Ser Arg Thr Val
        35                  40                  45

Thr Tyr Arg Ile Val Ser Tyr Thr
    50                  55

<210> SEQ ID NO 5
<211> LENGTH: 54
<212> TYPE: PRT
<213> ORGANISM: Homo sapiens

<400> SEQUENCE: 5

Met Gln Lys Phe Leu Gly Leu Glu Val Thr Gly Lys Leu Asp Ser Asp
1               5                   10                  15

Thr Leu Glu Val Met Arg Lys Pro Arg Cys Gly Val Pro Asp Val Gly
            20                  25                  30

His Phe Arg Thr Phe Pro Gly Ile Pro Lys Trp Arg Lys Thr His Leu
        35                  40                  45

Thr Tyr Arg Ile Val Asn
    50

<210> SEQ ID NO 6
<211> LENGTH: 55
<212> TYPE: PRT
<213> ORGANISM: Homo sapiens

<400> SEQUENCE: 6

Met Gln Lys Phe Leu Gly Leu Glu Val Thr Gly Lys Leu Asp Thr Asp
1               5                   10                  15

Thr Leu Glu Val Met Arg Lys Pro Arg Cys Gly Val Pro Asp Val Gly
            20                  25                  30

His Phe Ser Ser Phe Pro Gly Met Pro Lys Trp Arg Lys Thr His Leu
        35                  40                  45

Thr Tyr Arg Ile Val Asn Tyr
    50                  55

<210> SEQ ID NO 7
<211> LENGTH: 54
<212> TYPE: PRT
<213> ORGANISM: Homo sapiens

<400> SEQUENCE: 7

-continued

```
Met Gln His Phe Leu Gly Leu Lys Val Thr Gly Gln Leu Asp Thr Ser
 1               5                  10                  15

Thr Leu Glu Met Met His Ala Pro Arg Cys Gly Val Pro Asp Val His
            20                  25                  30

His Phe Arg Glu Met Pro Gly Pro Val Trp Arg Lys His Tyr Ile
        35                  40                  45

Thr Tyr Arg Ile Asn Asn
    50
```

<210> SEQ ID NO 8
<211> LENGTH: 47
<212> TYPE: PRT
<213> ORGANISM: Homo sapiens

<400> SEQUENCE: 8

```
Leu Gln Lys Gln Leu Ser Leu Pro Glu Thr Gly Glu Leu Asp Ser Ala
 1               5                  10                  15

Thr Leu Lys Ala Met Arg Thr Pro Arg Cys Gly Val Pro Asp Leu Gly
            20                  25                  30

Arg Phe Gln Thr Phe Glu Gly Asp Leu Lys Trp His His Asn
        35                  40                  45
```

<210> SEQ ID NO 9
<211> LENGTH: 54
<212> TYPE: PRT
<213> ORGANISM: Homo sapiens

<400> SEQUENCE: 9

```
Met Gln Glu Phe Phe Gly Leu Lys Val Thr Gly Lys Pro Asp Ala Glu
 1               5                  10                  15

Thr Leu Lys Val Met Lys Gln Pro Arg Cys Gly Val Pro Asp Val Ala
            20                  25                  30

Gln Phe Val Leu Thr Glu Gly Asn Pro Arg Trp Glu Gln Thr His Leu
        35                  40                  45

Thr Tyr Arg Ile Glu Asn
    50
```

<210> SEQ ID NO 10
<211> LENGTH: 55
<212> TYPE: PRT
<213> ORGANISM: Homo sapiens

<400> SEQUENCE: 10

```
Met Gln Arg Phe Phe Gly Leu Asn Val Thr Gly Lys Pro Asn Glu Glu
 1               5                  10                  15

Thr Leu Asp Met Met Lys Lys Pro Arg Cys Gly Val Pro Asp Ser Gly
            20                  25                  30

Gly Phe Met Leu Thr Pro Gly Asn Pro Lys Trp Glu Arg Thr Asn Leu
        35                  40                  45

Thr Tyr Arg Ile Arg Asn Tyr
    50                  55
```

<210> SEQ ID NO 11
<211> LENGTH: 19
<212> TYPE: PRT
<213> ORGANISM: Homo sapiens

<400> SEQUENCE: 11

```
Pro Arg Cys Gly Asn Pro Asp Val Ala Asn Tyr Asn Phe Phe Pro Arg
```

```
                1               5                  10                 15
Lys Pro Lys

<210> SEQ ID NO 12
<211> LENGTH: 9
<212> TYPE: PRT
<213> ORGANISM: Homo sapiens

<400> SEQUENCE: 12

Pro Arg Cys Gly Asn Pro Asp Val Ala
 1               5

<210> SEQ ID NO 13
<211> LENGTH: 10
<212> TYPE: PRT
<213> ORGANISM: Homo sapiens

<400> SEQUENCE: 13

Asn Tyr Asn Phe Phe Pro Arg Lys Pro Lys
 1               5                  10

<210> SEQ ID NO 14
<211> LENGTH: 660
<212> TYPE: PRT
<213> ORGANISM: Homo sapiens

<400> SEQUENCE: 14

Met Glu Ala Leu Met Ala Arg Gly Ala Leu Thr Gly Pro Leu Arg Ala
 1               5                  10                  15

Leu Cys Leu Leu Gly Cys Leu Leu Ser His Ala Ala Ala Ala Pro Ser
                20                  25                  30

Pro Ile Ile Lys Phe Pro Gly Asp Val Ala Pro Lys Thr Asp Lys Glu
            35                  40                  45

Leu Ala Val Gln Tyr Leu Asn Thr Phe Tyr Gly Cys Pro Lys Glu Ser
        50                  55                  60

Cys Asn Leu Phe Val Leu Lys Asp Thr Leu Lys Lys Met Gln Lys Phe
65                  70                  75                  80

Phe Gly Leu Pro Gln Thr Gly Asp Leu Asp Gln Asn Thr Ile Glu Thr
                85                  90                  95

Met Arg Lys Pro Arg Cys Gly Asn Pro Asp Val Ala Asn Tyr Asn Phe
            100                 105                 110

Phe Pro Arg Lys Pro Lys Trp Asp Lys Asn Gln Ile Thr Tyr Arg Ile
        115                 120                 125

Ile Gly Tyr Thr Pro Asp Leu Asp Pro Glu Thr Val Asp Asp Ala Phe
    130                 135                 140

Ala Arg Ala Phe Gln Val Trp Ser Asp Val Thr Pro Leu Arg Phe Ser
145                 150                 155                 160

Arg Ile His Asp Gly Glu Ala Asp Ile Met Ile Asn Phe Gly Arg Trp
                165                 170                 175

Glu His Gly Asp Gly Tyr Pro Phe Asp Gly Lys Asp Gly Leu Leu Ala
            180                 185                 190

His Ala Phe Ala Pro Gly Thr Gly Val Gly Gly Asp Ser His Phe Asp
        195                 200                 205

Asp Asp Glu Leu Trp Thr Leu Gly Glu Gly Gln Val Val Arg Val Lys
    210                 215                 220

Tyr Gly Asn Ala Asp Gly Glu Tyr Cys Lys Phe Pro Phe Leu Phe Asn
225                 230                 235                 240
```

```
Gly Lys Glu Tyr Asn Ser Cys Thr Asp Thr Gly Arg Ser Asp Gly Phe
                245                 250                 255
Leu Trp Cys Ser Thr Thr Tyr Asn Phe Glu Lys Asp Gly Lys Tyr Gly
            260                 265                 270
Phe Cys Pro His Glu Ala Leu Phe Thr Met Gly Gly Asn Ala Glu Gly
        275                 280                 285
Gln Pro Cys Lys Phe Pro Phe Arg Phe Gln Gly Thr Ser Tyr Asp Ser
    290                 295                 300
Cys Thr Thr Glu Gly Arg Thr Asp Gly Tyr Arg Trp Cys Gly Thr Thr
305                 310                 315                 320
Glu Asp Tyr Asp Arg Asp Lys Lys Tyr Gly Phe Cys Pro Glu Thr Ala
                325                 330                 335
Met Ser Thr Val Gly Gly Asn Ser Glu Gly Ala Pro Cys Val Phe Pro
            340                 345                 350
Phe Thr Phe Leu Gly Asn Lys Tyr Glu Ser Cys Thr Ser Ala Gly Arg
        355                 360                 365
Ser Asp Gly Lys Met Trp Cys Ala Thr Thr Ala Asn Tyr Asp Asp Asp
    370                 375                 380
Arg Lys Trp Gly Phe Cys Pro Asp Gln Gly Tyr Ser Leu Phe Leu Val
385                 390                 395                 400
Ala Ala His Glu Phe Gly His Ala Met Gly Leu Glu His Ser Gln Asp
                405                 410                 415
Pro Gly Ala Leu Met Ala Pro Ile Tyr Thr Tyr Thr Lys Asn Phe Arg
            420                 425                 430
Leu Ser Gln Asp Asp Ile Lys Gly Ile Gln Glu Leu Tyr Gly Ala Ser
        435                 440                 445
Pro Asp Ile Asp Leu Gly Thr Gly Pro Thr Pro Thr Leu Gly Pro Val
    450                 455                 460
Thr Pro Glu Ile Cys Lys Gln Asp Ile Val Phe Asp Gly Ile Ala Gln
465                 470                 475                 480
Ile Arg Gly Glu Ile Phe Phe Phe Lys Asp Arg Phe Ile Trp Arg Thr
                485                 490                 495
Val Thr Pro Arg Asp Lys Pro Met Gly Pro Leu Leu Val Ala Thr Phe
            500                 505                 510
Trp Pro Glu Leu Pro Glu Lys Ile Asp Ala Val Tyr Glu Ala Pro Gln
        515                 520                 525
Glu Glu Lys Ala Val Phe Phe Ala Gly Asn Glu Tyr Trp Ile Tyr Ser
    530                 535                 540
Ala Ser Thr Leu Glu Arg Gly Tyr Pro Lys Pro Leu Thr Ser Leu Gly
545                 550                 555                 560
Leu Pro Pro Asp Val Gln Arg Val Asp Ala Ala Phe Asn Trp Ser Lys
                565                 570                 575
Asn Lys Lys Thr Tyr Ile Phe Ala Gly Asp Lys Phe Trp Arg Tyr Asn
            580                 585                 590
Glu Val Lys Lys Lys Met Asp Pro Gly Phe Pro Lys Leu Ile Ala Asp
        595                 600                 605
Ala Trp Asn Ala Ile Pro Asp Asn Leu Asp Ala Val Val Asp Leu Gln
    610                 615                 620
Gly Gly Gly His Ser Tyr Phe Lys Gly Ala Tyr Tyr Leu Lys Leu
625                 630                 635                 640
Glu Asn Gln Ser Leu Lys Ser Val Lys Phe Gly Ser Ile Lys Ser Asp
                645                 650                 655
Trp Leu Gly Cys
```

660

<210> SEQ ID NO 15
<211> LENGTH: 43
<212> TYPE: PRT
<213> ORGANISM: Homo sapiens

<400> SEQUENCE: 15

Met Gln Lys Phe Phe Gly Leu Pro Gln Thr Gly Asp Leu Asp Gln Asn
1               5                   10                  15

Thr Ile Glu Thr Met Arg Lys Pro Arg Cys Gly Asn Pro Asp Val Ala
            20                  25                  30

Asn Tyr Asn Phe Phe Pro Arg Lys Pro Lys Trp
        35                  40

<210> SEQ ID NO 16
<211> LENGTH: 43
<212> TYPE: PRT
<213> ORGANISM: Homo sapiens

<400> SEQUENCE: 16

Leu Gln Lys Gln Leu Ser Leu Pro Glu Thr Gly Glu Leu Asp Ser Ala
1               5                   10                  15

Thr Leu Lys Ala Met Arg Thr Pro Arg Cys Gly Val Pro Asp Leu Gly
            20                  25                  30

Arg Phe Gln Thr Phe Glu Gly Asp Leu Lys Trp
        35                  40

<210> SEQ ID NO 17
<211> LENGTH: 43
<212> TYPE: PRT
<213> ORGANISM: Homo sapiens

<400> SEQUENCE: 17

Met Gln Glu Phe Phe Gly Leu Lys Val Thr Gly Lys Pro Asp Ala Glu
1               5                   10                  15

Thr Leu Lys Val Met Lys Gln Pro Arg Cys Gly Val Pro Asp Val Ala
            20                  25                  30

Gln Phe Val Leu Thr Glu Gly Asn Pro Arg Trp
        35                  40

<210> SEQ ID NO 18
<211> LENGTH: 35
<212> TYPE: PRT
<213> ORGANISM: Artificial Sequence
<220> FEATURE:
<223> OTHER INFORMATION: A synthetic matrix metalloproteinase
<220> FEATURE:
<221> NAME/KEY: SITE
<222> LOCATION: 2
<223> OTHER INFORMATION: Xaa = glutamine or glutamic acid
<220> FEATURE:
<221> NAME/KEY: SITE
<222> LOCATION: 5
<223> OTHER INFORMATION: Xaa = aspartic acid or glutamic acid
<220> FEATURE:
<221> NAME/KEY: SITE
<222> LOCATION: 8
<223> OTHER INFORMATION: Xaa = glutamine or serine
<220> FEATURE:
<221> NAME/KEY: SITE
<222> LOCATION: 9
<223> OTHER INFORMATION: Xaa = asparagine or alanine
<220> FEATURE:
<221> NAME/KEY: SITE
<222> LOCATION: 11

```
<223> OTHER INFORMATION: Xaa = isoleucine or leucine
<220> FEATURE:
<221> NAME/KEY: SITE
<222> LOCATION: (12)...(12)
<223> OTHER INFORMATION: Xaa = glutamic acid or lysine
<220> FEATURE:
<221> NAME/KEY: SITE
<222> LOCATION: (13)...(13)
<223> OTHER INFORMATION: Xaa = threonine or alanine
<220> FEATURE:
<221> NAME/KEY: SITE
<222> LOCATION: (16)...(16)
<223> OTHER INFORMATION: Xaa = lysine or threonine
<220> FEATURE:
<221> NAME/KEY: SITE
<222> LOCATION: (21)...(21)
<223> OTHER INFORMATION: Xaa = valine or asparagine
<220> FEATURE:
<221> NAME/KEY: SITE
<222> LOCATION: (24)...(24)
<223> OTHER INFORMATION: Xaa = valine or leucine
<220> FEATURE:
<221> NAME/KEY: SITE
<222> LOCATION: (25)...(25)
<223> OTHER INFORMATION: Xaa = alanine or glycine
<220> FEATURE:
<221> NAME/KEY: SITE
<222> LOCATION: (26)...(26)
<223> OTHER INFORMATION: Xaa = asparagine or arginine
<220> FEATURE:
<221> NAME/KEY: SITE
<222> LOCATION: (27)...(27)
<223> OTHER INFORMATION: Xaa = tyrosine or phenylalanine
<220> FEATURE:
<221> NAME/KEY: SITE
<222> LOCATION: (28)...(28)
<223> OTHER INFORMATION: Xaa = asparagine or glutamine
<220> FEATURE:
<221> NAME/KEY: SITE
<222> LOCATION: (29)...(29)
<223> OTHER INFORMATION: Xaa = phenylalanine or threonine
<220> FEATURE:
<221> NAME/KEY: SITE
<222> LOCATION: (31)...(31)
<223> OTHER INFORMATION: Xaa = proline or glutamic acid
<220> FEATURE:
<221> NAME/KEY: SITE
<222> LOCATION: (32)...(32)
<223> OTHER INFORMATION: Xaa = arginine or glycine
<220> FEATURE:
<221> NAME/KEY: SITE
<222> LOCATION: (33)...(33)
<223> OTHER INFORMATION: Xaa = lysine or aspartic acid
<220> FEATURE:
<221> NAME/KEY: SITE
<222> LOCATION: (34)...(34)
<223> OTHER INFORMATION: Xaa = proline or leucine

<400> SEQUENCE: 18

Pro Xaa Thr Gly Xaa Leu Asp Xaa Xaa Thr Xaa Xaa Xaa Met Arg Xaa
 1               5                  10                  15

Pro Arg Cys Gly Xaa Pro Asp Xaa Xaa Xaa Xaa Xaa Phe Xaa Xaa
             20                  25                  30

Xaa Xaa Lys
         35

<210> SEQ ID NO 19

<400> SEQUENCE: 19

000

<210> SEQ ID NO 20
```

-continued

```
<400> SEQUENCE: 20

000

<210> SEQ ID NO 21
<211> LENGTH: 35
<212> TYPE: PRT
<213> ORGANISM: Artificial Sequence
<220> FEATURE:
<223> OTHER INFORMATION: A synthetic peptide
<220> FEATURE:
<221> NAME/KEY: SITE
<222> LOCATION: (2)...(2)
<223> OTHER INFORMATION: Xaa = glutamine or glutamic acid
<220> FEATURE:
<221> NAME/KEY: SITE
<222> LOCATION: (5)...(5)
<223> OTHER INFORMATION: Xaa = aspartic acid or glutamic acid
<220> FEATURE:
<221> NAME/KEY: SITE
<222> LOCATION: (8)...(8)
<223> OTHER INFORMATION: Xaa = glutamine or serine
<220> FEATURE:
<221> NAME/KEY: SITE
<222> LOCATION: (9)...(9)
<223> OTHER INFORMATION: Xaa = asparagine or alanine
<220> FEATURE:
<221> NAME/KEY: SITE
<222> LOCATION: (11)...(11)
<223> OTHER INFORMATION: Xaa = isoleucine or leucine
<220> FEATURE:
<221> NAME/KEY: SITE
<222> LOCATION: (12)...(12)
<223> OTHER INFORMATION: Xaa = glutamic acid or lysine
<220> FEATURE:
<221> NAME/KEY: SITE
<222> LOCATION: (13)...(13)
<223> OTHER INFORMATION: Xaa = threonine or alanine
<220> FEATURE:
<221> NAME/KEY: SITE
<222> LOCATION: (16)...(16)
<223> OTHER INFORMATION: Xaa = lysine or threonine
<220> FEATURE:
<221> NAME/KEY: SITE
<222> LOCATION: 17, 20, 22
<223> OTHER INFORMATION: Xaa = any a polar amino acid
<220> FEATURE:
<221> NAME/KEY: SITE
<222> LOCATION: 18
<223> OTHER INFORMATION: Xaa= any basic amino acid
<220> FEATURE:
<221> NAME/KEY: SITE
<222> LOCATION: 19
<223> OTHER INFORMATION: Xaa = any cysteine-like amino acid
<220> FEATURE:
<221> NAME/KEY: SITE
<222> LOCATION: 21
<223> OTHER INFORMATION: Xaa = any polar or aliphatic amino acid
<220> FEATURE:
<221> NAME/KEY: SITE
<222> LOCATION: 23
<223> OTHER INFORMATION: Xaa = any acidic amino acid
<220> FEATURE:
<221> NAME/KEY: SITE
<222> LOCATION: (24)...(24)
<223> OTHER INFORMATION: Xaa = any aliphatic or polar amino acid
<220> FEATURE:
<221> NAME/KEY: SITE
<222> LOCATION: (25)...(25)
<223> OTHER INFORMATION: Xaa = any aliphatic, apolar or basic amino acid
<220> FEATURE:
<221> NAME/KEY: SITE
<222> LOCATION: (26)...(26)
<223> OTHER INFORMATION: Xaa = any polar, acidic, basic or apolar amino
      acid
<220> FEATURE:
<221> NAME/KEY: SITE
<222> LOCATION: (27)...(27)
```

```
-continued

<223> OTHER INFORMATION: Xaa = any polar or aromatic amino acid
<220> FEATURE:
<221> NAME/KEY: SITE
<222> LOCATION: (28)...(28)
<223> OTHER INFORMATION: Xaa = any polar, basic, aliphatic or apolar
      amino acid
<220> FEATURE:
<221> NAME/KEY: SITE
<222> LOCATION: (29)...(29)
<223> OTHER INFORMATION: Xaa = any aromatic, aliphatic, polar or acid
      amino acid
<220> FEATURE:
<221> NAME/KEY: SITE
<222> LOCATION: (30)...(30)
<223> OTHER INFORMATION: Xaa = any aromatic, apolar or polar amino acid
<220> FEATURE:
<221> NAME/KEY: SITE
<222> LOCATION: (31)...(31)
<223> OTHER INFORMATION: Xaa = any apolar or acidic amino acid
<220> FEATURE:
<221> NAME/KEY: SITE
<222> LOCATION: (32)...(32)
<223> OTHER INFORMATION: Xaa = any basic, polar, or apolar amino acid
<220> FEATURE:
<221> NAME/KEY: SITE
<222> LOCATION: (33)...(33)
<223> OTHER INFORMATION: Xaa = any basic, polar, aliphatic, apolar or
      acidic amino acid
<220> FEATURE:
<221> NAME/KEY: SITE
<222> LOCATION: (34)...(34)
<223> OTHER INFORMATION: Xaa = any apolar or aliphatic amino acid
<220> FEATURE:
<221> NAME/KEY: SITE
<222> LOCATION: (35)...(35)
<223> OTHER INFORMATION: Xaa = any basic or aliphatic amino acid

<400> SEQUENCE: 21

Pro Xaa Thr Gly Xaa Leu Asp Xaa Xaa Thr Xaa Xaa Xaa Met Arg Xaa
 1               5                  10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa
        35
```